United States Patent
Kuehnert et al.

(10) Patent No.: US 7,893,069 B2
(45) Date of Patent: Feb. 22, 2011

(54) SUBSTITUTED IMIDAZO[2,1-B]THIAZOLE COMPOUNDS AND USES THEREOF

(75) Inventors: Sven Kuehnert, Dueren (DE); Saskia Zemolka, Aachen (DE); Michael Haurand, Aachen (DE); Klaus Schiene, Duesseldorf (DE)

(73) Assignee: Gruenenthal GmbH, Aachen (DE)

( * ) Notice: Subject to any disclaimer, the term of this patent is extended or adjusted under 35 U.S.C. 154(b) by 205 days.

(21) Appl. No.: 12/207,307

(22) Filed: Sep. 9, 2008

(65) Prior Publication Data

US 2009/0005399 A1    Jan. 1, 2009

Related U.S. Application Data

(63) Continuation of application No. PCT/EP2007/002067, filed on Mar. 9, 2007.

(30) Foreign Application Priority Data

Mar. 10, 2006    (DE) .................... 10 2006 011 574

(51) Int. Cl.
  *A61K 31/506* (2006.01)
  *A61K 31/429* (2006.01)
  *A61K 31/4402* (2006.01)
  *A61K 31/4409* (2006.01)
  *A61K 31/4439* (2006.01)
  *C07D 513/04* (2006.01)
  *C07D 417/14* (2006.01)
  *C07D 401/14* (2006.01)

(52) U.S. Cl. .................. 514/256; 514/338; 514/368; 544/333; 546/270.1; 548/154

(58) Field of Classification Search ............... 548/154; 546/270.1; 514/338, 256, 368; 544/333
See application file for complete search history.

(56) References Cited

U.S. PATENT DOCUMENTS

| 2002/0183320 | A1 | 12/2002 | Gerlach et al. |
| 2007/0155965 | A1 | 7/2007 | Kuhnert et al. |

FOREIGN PATENT DOCUMENTS

| DE | 10 2004 044 884 A1 | 5/2006 |
| WO | WO 01/27118 A2 | 4/2001 |
| WO | WO 01//27119 A2 | 4/2001 |
| WO | WO 02/46166 A1 | 6/2002 |
| WO | WO 2004/080998 A1 | 9/2004 |
| WO | WO 2004/108701 A1 | 12/2004 |
| WO | WO 2004/111040 A1 | 12/2004 |
| WO | WO 2005/118568 A1 | 12/2005 |

OTHER PUBLICATIONS

Written Opinion of the International Search Authority dated Mar. 9, 2007 (ten (10) pages).
Gary J. Bennett, et al., "A peripheral mononeuropathy in rat that produces disorders of pain sensation like those seen in man", Neurobiology and Anesthesiology Branch, National Institute of Dental Research, National Institutes of Health, 1988, pp. 87-107, Elsevier Science Publishers B.V.
Sandy Hogg, "A Review of the Validity and Variability of the Elevated Pius-Maze as an Animal Model of Anxiety", Pharmacology Biochemistry and Behavior, 1996, pp. 21-30, vol. 54, No. 1, Elsevier Science Inc.
R. J. Rodgers, et al., "The Elevated Plus-maze: Pharmacology, Methodology and Ethology", Ethology and Psychopharmacology, pp. 9-44, 1994.
Jasuyoshi et al., "Iso:Synthesis and Structure-Activity Relationships of 3 . . . " In: Journal of Medicinal Chemistry 2006, 49(3), S. 1080-1100; zitiert als Chem. Abstr., AN: 2006: 20956, recherchiert in STN (HCAPLUS) am 1.12.06, Abstr.
Alagille et al., "Functionalization at position 3 of the phenyl ring of the potent . . . ", In: Bioorganic & Medicinal Chemistry Letters, 2005,15(4), S.945-949; zitiert als Chem. Abstr., AN:2005:86385, recherchiert In STN (HCAPLUS) am 1.12.06, Abstr.
German Search Report dated Dec. 14, 2006 w/English translation of pertinent portion (nine (9) pages).
International Search Report dated Sep. 5, 2007 w/English translation of pertinent portion (nine (9) pages).

*Primary Examiner*—Rebecca L Anderson
(74) *Attorney, Agent, or Firm*—Crowell & Moring LLP

(57) ABSTRACT

Substituted imidazo[2,1-b]thiazole compounds corresponding to formula I,

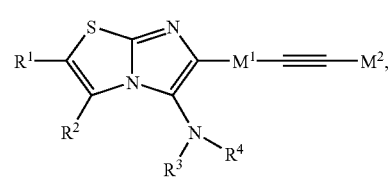

a method for producing them, pharmaceutical compositions containing them, and the use thereof for regulating mGluR5 receptors, or for treating or inhibiting disorders or disease states at least partially mediated by mGluR5 receptor such as pain, anxiety attacks, drug or alcohol dependency, and others.

30 Claims, No Drawings

SUBSTITUTED IMIDAZO[2,1-B]THIAZOLE COMPOUNDS AND USES THEREOF

CROSS REFERENCE TO RELATED APPLICATIONS

This application is a continuation of international patent application no. PCT/EP2007/002067, filed Mar. 9, 2007, designating the United States of America and published in German on Sep. 20, 2007 as WO 2007/104485, the entire disclosure of which is incorporated herein by reference. Priority is claimed based on Federal Republic of Germany patent application no. DE 10 2006 011 574.0, filed Mar. 10, 2006.

BACKGROUND OF THE INVENTION

The present invention relates to substituted imidazo[2,1-b]thiazole compounds, methods for producing them, drugs containing said compounds and their use for producing drugs.

Pain is one of the basic symptoms in clinics. There is a worldwide need for effective pain treatments. The urgency of the requirement for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Traditional opioids, such as morphine, are effective in the treatment of severe to very severe pain, but often lead to undesired side effects such as respiratory depression, vomiting, sedation, constipation or development of tolerance. Moreover, they are often not sufficiently effective in the case of neuropathic pain, from which tumour patients in particular suffer.

SUMMARY OF THE INVENTION

One object of the present invention was therefore to provide new compounds which are particularly suitable as active pharmaceutical substances in drugs, preferably in drugs for the treatment of pain.

It has surprisingly been found that the substituted imidazo[2,1-b]thiazole compounds of the general formula I indicated below are suitable for mGluR5 receptor regulation (mGluR5=metabotropic glutamate receptor 5) and can therefore be used as active pharmaceutical substances in drugs for the prevention and/or treatment of disorders or illnesses connected to these receptors or processes.

The present invention therefore relates to substituted imidazo[2,1-b]thiazole compounds of the general formula I:

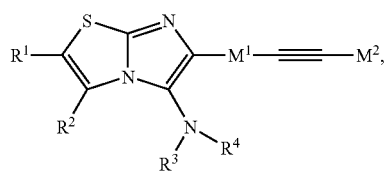

in which
$R^1$ and $R^2$ each independently denote hydrogen; a halogen residue; $-NO_2$; $-CN$; $-NH_2$; $-NHR^5$; $-NR^6R^7$; $-NH-C(=O)-R^8$; $-C(=O)-R^9$, $-C(=O)-NH_2$; $-C(=O)-NHR^{10}$; $-C(=O)-NR^{11}R^{12}$; $-C(=O)-OR^{13}$; $-(CH_2)_m-C(=O)-OR^{14}$ with m=1, 2, 3, 4 or 5; $-O-C(=O)-R^{15}$; $-(CH_2)_n-O-C(=O)-R^{16}$ with n=1, 2, 3, 4 or 5; $-OR^{17}$; $-(CH_2)_o-O-R^{18}$ with o=1, 2, 3; 4 or 5; $-SR^{19}$; $-(CH_2)_p-S(=O)_t-R^2$ with p=1, 2, 3, 4 or 5 and t=0, 1 or 2; $-NH-S(=O)_2-NR^{27}R^{28}$; $-S(=O)_2-NR^{29}R^{30}$; $-SF_5$; $-(CH_2)_u-O-S(=O)_2-R^{31}$ with u=1, 2, 3, 4 or 5; $-(CH_2)_v-O-S(=O)_2-O-R^{32}$ with v=1, 2, 3, 4 or 5; $-(CH_2)_w-O-P(=O)(OR^{33})(OR^{34})$ with w=1, 2, 3, 4 or 5; a linear or branched, saturated or unsaturated, unsubstituted or at least monosubstituted aliphatic residue; a saturated or unsaturated, unsubstituted or at least monosubstituted cycloaliphatic residue optionally having at least one heteroatom as a ring member, which cycloaliphatic residue is bound via a linear or branched, unsubstituted or at least monosubstituted alkylene group and/or can be condensed with an unsubstituted or at least monosubstituted mono- or polycyclic ring system; or an unsubstituted or at least monosubstituted aryl or heteroaryl residue, which can be bound via a linear or branched, unsubstituted or at least monosubstituted alkylene group and/or can be condensed with an unsubstituted or at least monosubstituted mono- or polycyclic ring system;

$R^3$ and $R^4$ each independently denote hydrogen; $-C(=O)-R^{21}$; $-(CH_2)_q-C(=O)-R^{22}$ with q=1, 2, 3, 4 or 5; $-C(=O)-O-R^{23}$; $-(CH_2)_r-C(=O)-O-R^{24}$ with r=1, 2, 3, 4 or 5; $-C(=O)-NHR^{25}$; $-(CH_2)_s-C(=O)-NHR^{26}$ with s=1, 2, 3, 4 or 5; a linear or branched, saturated or unsaturated, unsubstituted or at least monosubstituted aliphatic residue; a saturated or unsaturated, unsubstituted or at least monosubstituted cycloaliphatic residue optionally having at least one heteroatom as a ring member, which cycloaliphatic residue can be bound via a linear or branched, unsubstituted or at least monosubstituted alkylene group and/or can be condensed with an unsubstituted or at least monosubstituted mono- or polycyclic ring system; or an unsubstituted or at least monosubstituted aryl or heteroaryl residue, which can be bound via a linear or branched, unsubstituted or at least monosubstituted alkylene group and/or can be condensed with an unsubstituted or at least monosubstituted mono- or polycyclic ring system, or $R^3$ and $R^4$ together with the nitrogen atom connecting them together as a ring member form a saturated or unsaturated, unsubstituted or at least monosubstituted heterocycloaliphatic residue optionally having at least one further heteroatom as a ring member, which heterocycloaliphatic residue can be condensed with an unsubstituted or at least monosubstituted mono- or polycyclic ring system;

$R^5$, $R^6$, $R^7$, $R^8$, $R^{10}$, $R^{11}$, $R^{12}$, $R^{15}$ and $R^{16}$ each independently denote a linear or branched, saturated or unsaturated, unsubstituted or at least monosubstituted aliphatic residue or an unsubstituted or at least monosubstituted aryl or heteroaryl residue, which can be bound via a linear or branched, unsubstituted or at least monosubstituted alkylene group and/or can be condensed with an unsubstituted or at least monosubstituted mono- or polycyclic ring system;

$R^9$, $R^{13}$, $R^{14}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ each independently denote hydrogen; a linear or branched, saturated or unsaturated, unsubstituted or at least monosubstituted aliphatic residue or an unsubstituted or at least monosubstituted aryl or heteroaryl residue, which can be bound via a linear or branched, unsubstituted or at least monosubstituted alkylene group and/or can be condensed with an unsubstituted or at least monosubstituted mono- or polycyclic ring system;

$M^1$ denotes an aryl or heteroaryl residue, which can be substituted with at least one further substituent and/or can be condensed with an unsubstituted or at least monosubstituted mono- or polycyclic ring system; and $M^2$ denotes an aryl or heteroaryl residue, which can be unsubstituted or at least monosubstituted and can be condensed with an unsubstituted or at least monosubstituted mono- or polycyclic ring system;

in each case in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

If one or more of the above-mentioned substituents denotes a saturated or unsaturated aliphatic residue, i.e. an alkyl, alkenyl or alkynyl residue, which is monosubstituted or multiply substituted, this can preferably be substituted with optionally 1, 2, 3, 4 or 5, particularly preferably with 1, 2 or 3 substituents mutually independently selected from the group consisting of F, Cl, Br, I, —$NO_2$, —CN, —OH, —C(=O)—OH, —C(=O)—O—($C_{1-5}$-alkyl), —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=S)—$C_{1-5}$-alkyl, —C(=S)-phenyl and —$SO_3H$, whereby the above-mentioned $C_{1-5}$-alkyl residues can in each case be linear or branched and the above-mentioned phenyl residues can preferably be substituted with 1, 2, 3, 4 or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, —C(=O)—OH, —C(=O)—O—$CH_3$, —C(=O)—O—$C_2H_5$, methyl, ethyl, n-propyl, isopropyl, n-butyl, 2-butyl, isobutyl and tert-butyl.

An aliphatic residue, i.e. an alkyl, alkenyl or alkynyl residue, can particularly preferably be substituted with 1, 2 or 3 substituents mutually independently selected from the group consisting of F, Cl, Br, I, —$NO_2$, —CN, —OH, —C(=O)—OH, —C(=O)—O—$CH_3$, —SH, —$NH_2$, —N($CH_3$)$_2$, —N($C_2H_5$)$_2$ and —N($CH_3$)($C_2H_5$).

Alkenyl residues have at least one, preferably 1, 2, 3 or 4 C—C double-bonds and alkynyl residues have at least one, preferably 1, 2, 3 or 4 C—C-triple-bonds.

Examples of suitable $C_{1-10}$-alkyl residues, which can be unsubstituted or monosubstituted or multiply substituted include methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, 2-hexyl, 3-hexyl, n-heptyl, n-octyl, (2,4,4)-trimethylpent-2-yl, —C(H)($C_2H_5$)$_2$, —C(H)(n-$C_3H_7$)$_2$ and —$CH_2$—$CH_2$—C(H)($CH_3$)—($CH_2$)$_3$—$CH_3$.

Multiply substituted alkyl residues should be understood as such alkyl residues which are multiply substituted either at different or at the same C-atoms, preferably twice or three times, for example, three times at the same C-atom as in the case of —$CF_3$ or at various points as in the case of —(CHCl)—($CH_2F$). Multiple substitution can be performed with the same or with different substituents. —$CF_3$, —$CF_2H$, —$CFH_2$, —($CH_2$)—OH, —($CH_2$)—$NH_2$, —($CH_2$)—CN, —($CH_2$)—($CF_3$), —($CH_2$)—($CHF_2$), —($CH_2$)—($CH_2F$), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CH_2$)—($CF_3$) and —($CH_2$)—($CH_2$)—($CH_2$)—OH are cited as examples of suitable substituted alkyl residues.

Examples of suitable $C_{2-6}$-alkenyl residues include ethenyl, 1-propenyl, 2-propenyl, 1-butenyl, 2-butenyl, 3-butenyl, 1-pentenyl, 2-pentenyl, 3-pentenyl, 4-pentenyl, hexenyl, —CH=CH—CH=CH—$CH_3$ and —$CH_2$—$CH_2$—CH=$CH_2$.

Multiply substituted alkenyl residues should be understood as such alkenyl residues which are multiply substituted either at different or at the same C-atoms, preferably twice, for example, twice at the same C-atom as in the case of —CH=$CCl_2$ or at different points as in the case of —CCl=CH—($CH_2$)—$NH_2$. Multiple substitution can be performed with the same or with different substituents. —CH=CH—($CH_2$)—OH, —CH=CH—($CH_2$)—$NH_2$ and —CH=CH—CN are cited as examples of suitable substituted alkenyl residues.

Examples of suitable $C_{2-6}$-alkynyl residues include ethynyl, 1-propynyl, 2-propynyl, 1-butynyl, 2-butynyl, 3-butynyl, 1-pentynyl, 2-pentynyl, 3-pentynyl, 4-pentynyl and hexynyl.

Multiply substituted alkynyl residues should be understood as such alkynyl residues which are multiply substituted either at different C-atoms, for example, twice at different C-atoms as in the case of —CHCl—C≡CCl. —C≡C—F, —C≡C—Cl and —C≡C—I are cited as examples of suitable substituted alkynyl residues.

If one or more of the above-mentioned substituents denotes a cycloaliphatic residue or has a cycloaliphatic residue which is monosubstituted or multiply substituted, this can preferably be substituted with optionally 1, 2, 3, 4 or 5, particularly preferably with optionally 1, 2 or 3 substituents, which can be mutually independently selected from the group consisting of F, Cl, Br, I, —CN, —$NO_2$, —OH, —SH, —$SF_5$, —$NH_2$, oxo (=O), thioxo (=S), —C(=O)—OH, $C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —($CH_2$)—O—$C_{1-5}$-alkyl, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, N($C_{1-5}$alkyl)($C_{1-5}$-alkyl), —C(=O)—O—$C_{1-5}$-alkyl, —C(=O)—H, —C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, pyrazolyl, phenyl, furyl (furanyl), thiadiazolyl, thiophenyl (thienyl) and benzyl, whereby the above-mentioned $C_{1-5}$-alkyl residues can in each case be linear or branched and the cyclic substituents or the cyclic residues of these substituents themselves can in each case be substituted with optionally 1, 2, 3, 4 or 5, preferably with optionally 1, 2, 3 or 4 substituents mutually independently selected from the group consisting of F, Cl, Br, I, —CN, —$CF_3$, —OH, —$NH_2$, —O—$CF_3$, —SH, —O—$C_{1-5}$-alkyl, —O-phenyl, —O—$CH_2$-phenyl, —($CH_2$)—O—$C_{1-5}$-alkyl, —S—$C_{1-5}$-alkyl, —S-phenyl, —S—$CH_2$-phenyl, —$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —C(=O)—O—$C_{1-5}$-alkyl and —C(=O)—$CF_3$.

The substituents can particularly preferably be, in each case independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si($CH_3$)$_3$, —C≡C—Si($C_2H_5$)$_3$, —C≡C—Si($CH_3$)$_3$, —C≡C—Si($C_2H_5$)$_3$, —$CH_2$—O—$CH_3$, —$CH_2$—O—$C_2H_5$, —OH, —SH, —$SF_5$, —$NH_2$, oxo (=O), thioxo (=S), —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl, whereby the cyclic substituents or the cyclic residues of these substituents themselves can be substituted with optionally 1, 2, 3, 4 or 5, preferably with optionally 1, 2, 3 or 4 substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —C(=O)—O—C$_{1-5}$-alkyl and —C(=O)—CF$_3$.

If the cycloaliphatic residues have one or more heteroatoms as ring members, these can preferably have optionally 1, 2, 3, 4 or 5, particularly preferably 1, 2 or 3 heteroatom(s) as (the) ring member(s), which can in each case mutually independently be selected from the group consisting of nitrogen, oxygen and sulfur.

Examples of cycloaliphatic residues which optionally may be monosubstituted or multiply substituted include cyclopropyl, cyclobutyl, cyclopentyl, cyclohexyl, cycloheptyl, cyclooctyl, cyclononyl, cyclodecyl, cycloundecyl, cyclododecyl, cycloheptyl, cyclopentenyl, cyclohexenyl, cycloheptenyl, cyclooctenyl, oxiranyl, aziridinyl, tetrahydrofuranyl, tetrahydrothienyl, pyrrolidinyl, isoxazolidinyl, isothioazolidinyl, pyrazolidinyl, oxazolidinyl, thiazolidinyl, imidazolidinyl, (1,2,4)-oxadiazolidinyl, (1,2,4)-thiadiazolidinyl, (1,2,4)-triazolidin-3-yl, (1,3,4)-thiadiazolidinyl, (1,3,4)-triazolidin-1-yl, (1,3,4)-triazolidin-2-yl, (2,3)-dihydrofuryl, (2,5)-dihydrofuryl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, morpholinyl, piperidinyl, piperazinyl, azocanyl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,2,4)-tetrahydrotriazin-3-yl, (1,3)-dihydrooxazinyl, (1,3)-dithian-2-yl, tetrahydropyranyl, (1,3)-dioxolan-2-yl, (3,4,5,6)-tetrahydropyridin-2-yl, (1,2,5,6)-tetrahydropyridin-1-yl, (1,2,3,4)-tetrahydropyridin-1-yl, (1,2)-dihydropyridin-1-yl, (1,4)-dihydropyridin-1-yl, 4H-1,3-thiazinyl, (1,3)-dihydrooxazin-2-yl, azepanyl, (1,4)-diazepanyl, thiomorpholinyl and dithiolanyl.

Particularly preferred cycloaliphatic residues which optionally may be monosubstituted or multiply substituted are cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl.

If the cycloaliphatic residue is condensed with an unsubstituted or at least monosubstituted, saturated, unsaturated or aromatic mono- or polycyclic ring system, suitable unsubstituted or at least monosubstituted residues can be selected from the group consisting of 2,3-dihydro-benzo[1,4]dioxinyl; 3,4-dihydro-2H-benzo[1,4]oxazinyl; benzo[1,3]dioxolyl; (1,2,3,4)-tetrahydroquinazolinyl; indanyl; (1,2,3,4)-tetrahydronaphthyl; 1H-indenyl; (1,2,3,4)-tetrahydroquinolinyl; (1,2,3,4)-tetrahydroisoquinolinyl; (2,3)-dihydro-1H-indolyl, (2,3)-dihydro-1H-isoindolyl and decahydroisoquinolinyl.

If two of the above-mentioned substituents together with the nitrogen atom connecting them together as a ring member form a saturated or unsaturated heterocycloaliphatic residue which is monosubstituted or multiply substituted, this can preferably be substituted with optionally 1, 2, 3, 4 or 5, particularly preferably with optionally 1, 2 or 3 substituents mutually independently selected from the group consisting of F, Cl, Br, I, —CN, —CF$_3$, —OH, —NH$_2$, —O—CF$_3$, —SH, —SF$_5$, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo (=O), thioxo (=S), —N(C$_{1-5}$-alkyl)$_2$, —N(H)(C$_{1-5}$-alkyl), —NO$_2$, —S—CF$_3$, —C(=O)—OH, —NH—S(=O)$_2$—C$_{1-5}$-alkyl, —NH—C(=O)—C$_{1-5}$-alkyl, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl) and phenyl, whereby the above-mentioned C$_{1-5}$-alkyl residues can in each case be linear or branched and the phenyl residues can in each case be unsubstituted or substituted with 1, 2, 3, 4 or 5, preferably with 1, 2, 3 or 4 substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$.

The substituents are particularly preferably each independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —OH, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —SF$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH—S(=O)$_2$—CH$_3$, —C(=O)—OH, —C(=O)—H; —C(=O)—CH$_3$, —C(=O)—C$_2$H$_5$, —C(=O)—N(CH$_3$)$_2$, —C(=O)—NH—CH$_3$, —C(=O)—NH$_2$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl, whereby the phenyl residue optionally may be substituted with 1, 2, 3, 4 or 5, preferably 1, 2 or 3 substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —C(=O)—O—C$_{1-5}$-alkyl and —C(=O)—CF$_3$.

If the heterocycloaliphatic residues have one or more further heteroatoms as ring members, these can preferably have optionally 1, 2, 3, 4 or 5, particularly preferably optionally 1, 2 or 3, further heteroatom(s) as (the) ring member(s), which can in each case mutually independently be selected from the group consisting of nitrogen, oxygen and sulfur.

Examples of suitable heterocycloaliphatic residues which optionally may be monosubstituted or multiply substituted include imidazolidinyl, piperidinyl, piperazinyl, morpholinyl, pyrrolidinyl, thiomorpholinyl, azepanyl, diazepanyl and azocanyl.

If the heterocycloaliphatic residue is condensed with an unsubstituted or at least monosubstituted, saturated, unsaturated or aromatic mono- or polycyclic ring system, suitable unsubstituted or at least monosubstituted residues can be selected from the group consisting of (3,4)-dihydro-2H-benzo[1,4]oxazinyl; (1,2,3,4)-tetrahydroquinazolinyl; (1,2,3,4)-tetrahydroquinolinyl; (1,2,3,4)-tetrahydroisoquinolinyl, (2,3)-dihydro-1H-indolyl, (2,3)-dihydro-1H-isoindolyl and decahydroisoquinolinyl.

If one or more of the above-mentioned substituents denotes an aryl or heteroaryl residue or has an aryl or heteroaryl residue, which is monosubstituted or multiply substituted, this can preferably be substituted with optionally 1, 2, 3, 4 or 5, particularly preferably with optionally 1, 2 or 3 substituents mutually independently selected from the group consisting of F, Cl, Br, I, —CN, —CH$_2$—CN, —NO$_2$, —OH, —SH, —SF$_5$, —NH$_2$, —CH$_2$—NH$_2$, —C(=O)—OH, —C$_{1-5}$-alkyl, —(CH$_2$)—O—C$_{1-5}$-alkyl, —CH$_2$—OH, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$alkyl)$_2$, —C(=O)—O—C$_{1-5}$-alkyl, —C(=O)—H; —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —NH—C(=NH)—NH$_2$, —NH—S(=O)$_2$—OH, —C(=O)—NH$_2$, —C(=O)—NH—C$_{1-5}$-alkyl, —C(=O)—N(C$_{1-5}$-alkyl)$_2$, —Si(phenyl)$_2$[C$_{1-5}$-alkyl], —S(=O)$_2$—NH$_2$, —S(=O)$_2$—NH—C$_{1-5}$-alkyl, —S(=O)$_2$—N(C$_{1-5}$-alkyl)$_2$, cyclopropyl, cyclobutyl, cyclopentyl, cyclohexyl, (1,3)-dioxolanyl, pyrazolyl, pyrrolyl, phenyl, furyl (furanyl), thiazolyl, thiadiazolyl, thiophenyl (thienyl), benzyl and phenethyl, whereby the above-mentioned C$_{1-5}$-alkyl residues can in each case be linear or branched and the cyclic substituents or the cyclic residues of these substituents themselves can be substituted with optionally 1, 2, 3, 4 or 5, preferably with optionally 1, 2, 3 or 4 substituents mutually independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

The substituents can particularly preferably each be independently selected from the group consisting of F, Cl, Br, I, —CN, —CH$_2$—CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —CH$_2$—NH$_2$, —CH$_2$—OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —NH—S(=O)$_2$—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], —S(=O)$_2$—NH$_2$, —S(=O)$_2$—NH—CH$_3$, —S(=O)$_2$—N(CH$_3$)$_2$, —NH—C(=NH)—NH$_2$, —NH—S(=O)$_2$—OH, (1,3)-dioxolanyl, pyrrolyl, cyclopropyl, cyclobutyl, cyclopentyl, cyclohexyl, phenyl, furyl (furanyl), thiadiazolyl, thiophenyl (thienyl) and benzyl, whereby the cyclic substituents or the cyclic residues of these substituents themselves can be substituted in each case with optionally 1, 2, 3, 4, or 5, preferably with optionally 1, 2, 3 or 4 substituents mutually independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

A substituted aryl residue can very particularly preferably be selected from the group consisting of 2-methyl-phenyl, 3-methyl-phenyl, 4-methyl-phenyl, 2-fluoro-phenyl, 3-fluoro-phenyl, 4-fluoro-phenyl, 2-cyano-phenyl, 3-cyano-phenyl, 4-cyano-phenyl, 2-hydroxy-phenyl, 3-hydroxy-phenyl, 4-hydroxy-phenyl, 2-amino-phenyl, 3-amino-phenyl, 4-amino-phenyl, 2-dimethylamino-phenyl, 3-dimethylamino-phenyl, 4-dimethylamino-phenyl, 2-methylamino-phenyl, 3-methylamino-phenyl, 4-methylamino-phenyl, 2-acetyl-phenyl, 3-acetyl-phenyl, 4-acetyl-phenyl, 2-methylsulfinyl-phenyl, 3-methylsulfinyl-phenyl, 4-methylsulfinyl-phenyl, 2-methylsulfonyl-phenyl, 3-methylsulfonyl-phenyl, 4-methylsulfonyl-phenyl, 2-methoxy-phenyl, 3-methoxy-phenyl, 4-methoxy-phenyl, 2-chloro-phenyl, 3-chloro-phenyl, 4-chloro-phenyl, 2-ethoxy-phenyl, 3-ethoxy-phenyl, 4-ethoxyphenyl, 2-trifluoromethyl-phenyl, 3-trifluoromethyl-phenyl, 4-trifluoromethyl-phenyl, 2-difluoromethyl-phenyl, 3-difluoromethyl-phenyl, 4-difluoromethyl-phenyl, 2-fluoromethyl-phenyl, 3-fluoromethyl-phenyl, 4-fluoromethyl-phenyl, 2-nitro-phenyl, 3-nitro-phenyl, 4-nitro-phenyl, 2-ethyl-phenyl, 3-ethyl-phenyl, 4-ethyl-phenyl, 2-propyl-phenyl, 3-propyl-phenyl, 4-propyl-phenyl, 2-isopropyl-phenyl, 3-isopropyl-phenyl, 4-isopropyl-phenyl, 2-tert-butyl-phenyl, 3-tert-butyl-phenyl, 4-tert-butyl-phenyl, 2-carboxyphenyl, 3-carboxy-phenyl, 4-carboxyphenyl, 2-ethenyl-phenyl, 3-ethenyl-phenyl, 4-ethenyl-phenyl, 2-ethynyl-phenyl, 3-ethynyl-phenyl, 4-ethynyl-phenyl, 2-allyl-phenyl, 3-allyl-phenyl, 4-allyl-phenyl, 2-trimethylsilanylethinyl-phenyl, 3-trimethylsilanylethinyl-phenyl, 4-trimethylsilanylethinyl-phenyl, 2-formyl-phenyl, 3-formyl-phenyl, 4-formyl-phenyl, 2-acetamino-phenyl, 3-acetamino-phenyl, 4-acetamino-phenyl, 2-dimethylaminocarbonyl-phenyl, 3-dimethylaminocarbonyl-phenyl, 4-dimethylaminocarbonyl-phenyl, 2-methoxymethyl-phenyl, 3-methoxymethyl-phenyl, 4-methoxymethyl-phenyl, 2-ethoxymethyl-phenyl, 3-ethoxymethyl-phenyl, 4-ethoxymethyl-phenyl, 2-aminocarbonyl-phenyl, 3-aminocarbonyl-phenyl, 4-aminocarbonyl-phenyl, 2-methylaminocarbonyl-phenyl, 3-methylaminocarbonyl-phenyl, 4-methylaminocarbonyl-phenyl, 2-carboxymethylester-phenyl, 3-carboxymethylester-phenyl, 4-carboxymethylester-phenyl, 2-carboxyethylester-phenyl, 3-carboxyethylester-phenyl, 4-carboxyethylester-phenyl, 2-carboxy-tert-butylester-phenyl, 3-carboxy-tert-butylester-phenyl, 4-carboxy-tert-butylester-phenyl, 2-methylmercapto-phenyl, 3-methylmercapto-phenyl, 4-methylmercapto-phenyl, 2-ethylmercapto-phenyl, 3-ethylmercapto-phenyl, 4-ethylmercaptophenyl, 2-biphenyl, 3-biphenyl, 4-biphenyl, 2-bromophenyl, 3-bromophenyl, 4-bromophenyl, 2-iodo-phenyl, 3-iodophenyl, 4-iodophenyl, 2-trifluoromethoxy-phenyl, 3-trifluoromethoxy-phenyl, 4-trifluoromethoxy-phenyl, 2-fluoro-3-trifluoromethylphenyl, 2-fluoro-4-methyl-phenyl, (2,3)-difluorophenyl, (2,3)-dimethyl-phenyl, (2,3)-dichlorophenyl, 3-fluoro-2-trifluoromethylphenyl, (2,4)-dichlorophenyl, (2,4)-difluorophenyl, 4-fluoro-2-trifluoromethyl-phenyl, (2,4)-dimethoxyphenyl, 2-chloro-4-fluoro-phenyl, 2-chloro-4-nitro-phenyl, 2-chloro-4-methyl-phenyl, 2-chloro-5-trifluoromethyl-phenyl, 2-chloro-5-methoxy-phenyl, 2-bromo-5-trifluoromethyl-phenyl, 2-bromo-5-methoxy-phenyl, (2,4)-dibromo-phenyl, (2,4)-dimethyl-phenyl, 2-fluoro-4-trifluoromethyl-phenyl, (2,5)-difluoro-phenyl, 2-fluoro-5-trifluoromethyl-phenyl, 5-fluoro-2-trifluoromethyl-phenyl, 5-chloro-2-trifluoromethyl-phenyl, 5-bromo-2-trifluoromethyl-phenyl, (2,5)-dimethoxy-phenyl, (2,5)-bis-trifluoromethyl-phenyl, (2,5)-dichloro-phenyl, (2,5)-dibromo-phenyl, 2-methoxy-5-nitro-phenyl, 2-fluoro-6-trifluoromethyl-phenyl, (2,6)-dimethoxy-phenyl, (2,6)-dimethyl-phenyl, (2,6)-dichloro-phenyl, 2-chloro-6-fluoro-phenyl, 2-bromo-6-chloro-phenyl, 2-bromo-6-fluor-phenyl, (2,6)-difluoro-phenyl, (2,6)-difluoro-3-methyl-phenyl, (2,6)-dibromo-phenyl, (2,6)-dichlorophenyl, 3-chloro-2-fluoro-phenyl, 3-chloro-5-methyl-phenyl, (3,4)-dichlorophenyl, (3,4)-dimethyl-phenyl, 3-methyl-4-methoxy-phenyl, 4-chloro-3-nitro-phenyl, (3,4)-dimethoxy-phenyl, 4-fluoro-3-trifluoromethylphenyl, 3-fluoro-4-trifluoromethyl-phenyl, (3,4)-difluoro-phenyl, 3-cyano-4-fluoro-phenyl, 3-cyano-4-methyl-phenyl, 3-cyano-4-methoxy-phenyl, 3-bromo-4-fluoro-phenyl, 3-bromo-4-methyl-phenyl, 3-bromo-4-methoxy-phenyl, 4-chloro-2-fluoro-phenyl, 4-chloro-3-trifluoromethyl, 4-bromo-3-methyl-phenyl, 4-bromo-5-methyl-phenyl, 3-chloro-4-fluoro-phenyl, 4-fluoro-3-nitro-phenyl, 4-bromo-3-nitro-phenyl, (3,4)-dibromo-phenyl, 4-chloro-3-methyl-phenyl, 4-bromo-3-methyl-phenyl, 4-fluoro-3-methyl-phenyl, 3-fluoro-4-methyl-phenyl, 3-fluoro-5-methyl-phenyl, 2-fluoro-3-methyl-phenyl, 4-methyl-3-nitro-phenyl, (3,5)-dimethoxy-phenyl, (3,5)-dimethyl-phenyl, (3,5)-bis-trifluoromethyl-phenyl, (3,5)-difluoro-phenyl, (3,5)-dinitro-phenyl, (3,5)-dichloro-phenyl, 3-fluoro-5-trifluoromethyl-phenyl, 5-fluoro-3-trifluoromethyl-phenyl, (3,5)-dibromo-phenyl, 5-chloro-4-fluoro-phenyl, 5-chloro-4-fluoro-phenyl, 5-bromo-4-methyl-phenyl, (2,3,4)-trifluorophenyl, (2,3,4)-trichlorophenyl, (2,3,6)-trifluoro-phenyl, 5-chloro-2-methoxy-phenyl, (2,3)-difluoro-4-methyl, (2,4,5)-trifluoro-phenyl, (2,4,5)-trichloro-phenyl, (2,4)-dichloro-5-fluoro-phenyl, (2,4,6)-trichloro-phenyl, (2,4,6)-trimethylphenyl, (2,4,6)-trifluoro-phenyl, (2,4,6)-trimethoxy-phenyl, (3,4,5)-trimethoxy-phenyl, (2,3,4,5)-tetrafluoro-phenyl, 4-methoxy-(2,3,6)-trimethyl-phenyl, 4-methoxy-(2,3,6)-trimethyl-phenyl, 4-chloro-2,5-dimethyl-phenyl, 2-chloro-6-fluoro-3-methyl-phenyl, 6-chloro-2-fluoro-3-methyl, (2,4,6)-trimethylphenyl and (2,3,4,5,6)-pentafluoro-phenyl.

A substituted heteroaryl residue can very particularly preferably be selected from the group consisting of 3-methyl-pyrid-2-yl, 4-methyl-pyrid-2-yl, 5-methyl-pyrid-2-yl, 6-methyl-pyrid-2-yl, 2-methyl-pyrid-3-yl, 4-methyl-pyrid-3-yl, 5-methyl-pyrid-3-yl, 6-methyl-pyrid-3-yl, 2-methyl-pyrid-4-yl, 3-methyl-pyrid-4-yl, 3-fluoro-pyrid-2-yl, 4-fluoro-pyrid-2-yl, 5-fluoro-pyrid-2-yl, 6-fluoro-pyrid-2-yl, 3-chloro-pyrid-2-yl, 4-chloro-pyrid-2-yl, 5-chloro-pyrid-2-yl, 6-chloro-pyrid-2-yl, 3-trifluoromethyl-pyrid-2-yl, 4-trifluoromethyl-pyrid-2-yl, 5-trifluoromethyl-pyrid-2-yl, 6-trifluoromethyl-pyrid-2-yl, 3-methoxy-pyrid-2-yl, 4-methoxy-pyrid-2-yl, 5-methoxy-pyrid-2-yl, 6-methoxy-pyrid-2-yl, 4-methyl-thiazole-2-yl, 5-methyl-thiazole-2-yl, 4-trifluoromethyl-thiazole-2-yl, 5-trifluoromethyl-thiazole-2-yl, 4-chloro-thiazole-2-yl, 5-chloro-thiazole-2-yl, 4-bromo-thiazole-2-yl, 5-bromo-thiazole-2-yl, 4-fluoro-thiazole-2-yl, 5-fluoro-thiazole-2-yl, 4-cyano-thiazole-2-yl, 5-cyano-thiazole-2-yl, 4-methoxy-thiazole-2-yl, 5-methoxy-thiazole-2-yl, 4-methyl-oxazole-2-yl, 5-methyl-oxazole-2-yl, 4-trifluoromethyl-oxazole-2-yl, 5-trifluoromethyl-oxazole-2-yl, 4-chloro-oxazole-2-yl, 5-chloro-oxazole-2-yl, 4-bromo-oxazole-2-yl, 5-bromo-oxazole-2-yl, 4-fluoro-oxazole-2-yl, 5-fluoro-oxazole-2-yl, 4-cyano-oxazole-2-yl, 5-cyano-oxazole-2-yl, 4-methoxy-oxazole-2-yl, 5-methoxy-oxazole-2-yl, 2-methyl-(1,2,4)-thiadiazole-5-yl, 2-trifluoromethyl-(1,2,4)-thiadiazole-5-yl, 2-chloro-(1,2,4)-thiadiazole-5-yl, 2-fluoro-(1,2,4)-thiadiazole-5-yl, 2-methoxy-(1,2,4)-thiadiazole-5-yl, 2-cyano-(1,2,4)-thiadiazole-5-yl, 2-methyl-(1,2,4)-oxadiazole-5-yl, 2-trifluoromethyl-(1,2,4)-oxadiazole-5-yl, 2-chloro-(1,2,4)-oxadiazole-5-yl, 2-fluoro-(1,2,4)-oxadiazole-5-yl, 2-methoxy-(1,2,4)-oxadiazole-5-yl and 2-cyano-(1,2,4)-oxadiazole-5-yl.

Examples of suitable aryl residues include phenyl, 1-naphthyl, 2-naphthyl and anthracenyl. A suitable 6-membered aryl residue is a phenyl residue.

If one or more of the above-mentioned substituents denotes a heteroaryl residue or contains a heteroaryl residue, the heteroatom(s) thereof can, in each case mutually independently, preferably be selected from the group consisting of oxygen, sulfur and nitrogen. A heteroaryl residue can preferably have optionally 1, 2, 3, 4 or 5, particularly preferably 1, 2 or 3 heteroatoms.

Examples of suitable 5- or 6-membered heteroaryl residues include furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl and pentazolyl.

Examples of suitable 9- or 10-membered heteroaryl residues include indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl.

Aryl or heteroaryl residues within the scope of the present invention optionally may be condensed (annelated) with a mono- or bicyclic ring system. If a 5- or 6-membered heteroaryl residue is condensed with an unsubstituted or at least monosubstituted aromatic mono- or polycyclic ring system, suitable unsubstituted or at least monosubstituted residues can be selected from the group consisting of indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl.

Examples of 6-membered aryl residues condensed with an unsubstituted or at least monosubstituted saturated mono- or polycyclic ring system include (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, benzo[1.3]dioxolyl and (3,4)-dihydro-2H-benzo[1.4]oxazinyl groups.

In the context of the present invention a mono- or polycyclic ring system should be understood as referring to mono- or polycyclic hydrocarbon residues which can be saturated, unsaturated or aromatic and can optionally contain one or more heteroatoms as ring members. Such a mono- or polycyclic ring system can, for example, be condensed (annelated) with a cycloaliphatic residue, a heterocycloaliphatic residue, an aryl residue or a heteroaryl residue.

If a polycyclic ring system such as, for example, a bicyclic ring system is present, the various rings, in each case mutually independently, can have a different degree of saturation, i.e. be saturated, unsaturated or aromatic. The heteroatoms of each ring can, in each case mutually independently, be preferably selected from the group consisting of oxygen, nitrogen and sulfur. A ring preferably contains 0, 1, 2 or 3 heteroatoms. The respective rings of the mono- or polycyclic ring system are preferably 5-, 6- or 7-membered, particularly preferably 5- or 6-membered.

If one or more of the above-mentioned substituents contains a saturated, unsaturated or aromatic monocyclic or polycyclic ring system which is monosubstituted or multiply substituted, this can preferably be substituted with optionally 1, 2, 3, 4 or 5, particularly preferably with optionally 1, 2 or 3 substituents independently selected from the group consisting of oxo (=O), thioxo (=S), F, Cl, Br, I, —CN, —NO$_2$, —OH, —CH$_2$—OH, —SH, —SF$_5$, —NH$_2$, —CH$_2$—NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$alkyl)$_2$, —C(=O)—O—C$_{1-5}$-alkyl, —C(=O)—H; —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —NH—C(=NH)—NH$_2$, —NH—S(=O)$_2$—OH, —C(=O)—NH$_2$, —C(=O)—NH—C$_{1-5}$-alkyl, —C(=O)—N(C$_{1-5}$-alkyl)$_2$, —Si(phenyl)$_2$[C$_{1-5}$-alkyl], —S(=O)$_2$—NH$_2$, —S(=O)$_2$—NH—C$_{1-5}$-alkyl, —S(=O)$_2$—N(C$_{1-5}$-alkyl)$_2$, cyclopropyl, cyclobutyl, cyclopentyl, cyclohexyl, (1,3)-dioxolanyl, pyrazolyl, pyrrolyl, phenyl, furyl (furanyl), thiazolyl, thiadiazolyl, thiophenyl (thienyl), benzyl and phenethyl, whereby the above-mentioned C$_{1-5}$-alkyl residues can in each case be linear or branched and the cyclic substituents or the cyclic residues of these substituents themselves can be substituted with optionally 1, 2, 3, 4 or 5, preferably with optionally 1, 2, 3 or 4 substituents mutually independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

The substituents can particularly preferably, in each case mutually independently, be selected from the group consisting of oxo (=O), thioxo (=S), F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —CH$_2$—NH$_2$, —CH$_2$—OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —NH—S(=O)$_2$—C$_2$H$_5$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], —S(=O)$_2$—NH$_2$, —S(=O)$_2$—NH—CH$_3$, —S(=O)$_2$—N(CH$_3$)$_2$, —NH—C(=NH)—NH$_2$, —NH—S(=O)$_2$—OH, (1,3)-dioxolanyl, pyrrolyl, cyclopropyl, cyclobutyl, cyclopentyl, cyclohexyl, phenyl, furyl (furanyl), thiadiazolyl, thiophenyl (thienyl) and benzyl, whereby the cyclic substituents or the cyclic residues of these substituents themselves can in each case be substituted with optionally 1, 2, 3, 4, or 5, preferably with optionally 1, 2, 3 or 4 substituents mutually independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

If one of the above-mentioned substituents contains a linear or branched alkylene group, the alkylene group can preferably be selected from the group consisting of —(CH$_2$)—, —(CH$_2$)$_2$—, —C(H)(CH$_3$)—, —(CH$_2$)$_3$—, —(CH$_2$)$_4$—, —(CH$_2$)$_5$— and —C(C$_2$H$_5$)(H)—. An alkylene group can particularly preferably be substituted with 1, 2 or 3 substituents independently selected from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Persons skilled in the art will understand that some of the substituted imidazo[2,1-b]thiazole compounds corresponding to formula I according to the invention may be present in the form of tautomers which are also included within the scope of the present invention and in each case may also be present as active ingredients in the pharmaceutical compositions described below.

Substituted imidazo[2,1-b]thiazole compounds corresponding to formula I indicated above are preferred, in which $R^1$ and $R^2$ each independently denote hydrogen; a halogen residue; —NO$_2$; —CN; —NH$_2$; —NHR$^5$; —NR$^6$R$^7$; —NH—C(=O)—R$^8$; —C(=O)—R$^9$, —C(=O)—NH$_2$; —C(=O)—NHR$^{10}$; —C(=O)—NR$^{11}$R$^{12}$; —C(=O)—OR$^{13}$; —(CH$_2$)$_m$—C(=O)—OR$^{14}$ with m=1, 2, 3, 4 or 5; —O—C(=O)—R$^{15}$; —(CH$_2$)$_n$—O—C(=O)—R$^{16}$ with n=1, 2, 3, 4 or 5; —OR$^{17}$; —(CH$_2$)$_o$—O—R$^{18}$ with o=1, 2, 3; 4 or 5; —SR$^{19}$; —(CH$_2$)$_p$—S(=O)$_t$—R$^{21}$ with p=1, 2, 3, 4 or 5 and t=0, 1 or 2; —NH—S(=O)$_2$—NR$^{27}$R$^{28}$; —S(=O)$_2$—NR$^{29}$R$^{31}$; —SF$_5$; —(CH$_2$)$_u$—O—S(=O)$_2$—R$^{31}$ with u=1, 2, 3, 4 or 5; —(CH$_2$)$_v$—O—S(=O)$_2$—O—R$^{32}$ with v=1, 2, 3, 4 or 5; —(CH$_2$)$_w$—O—P(=O)(OR$^{33}$)(OR$^{34}$) with w=1, 2, 3, 4 or 5; a linear or branched, unsubstituted or at least monosubstituted C$_{1-10}$-alkyl residue, C$_{2-6}$-alkenyl residue or C$_{2-6}$-alkynyl residue; a saturated or unsaturated, unsubstituted or at least monosubstituted cycloaliphatic C$_{3-8}$ residue optionally having at least one heteroatom as a ring member, which residue can be bound via a linear or branched, unsubstituted or at least monosubstituted C$_{1-5}$-alkylene group; or an unsubstituted or at least monosubstituted 5- or 6-membered aryl or heteroaryl residue, which can be bound via a linear or branched, unsubstituted or at least monosubstituted $C_{1-5}$-alkylene group and/or can be condensed with an unsubstituted or at least monosubstituted mono- or polycyclic ring system, whereby the rings of the ring system are in each case 5-, 6- or 7-membered;

$R^3$ and $R^4$ each independently denote hydrogen; —C(=O)—$R^{21}$; —(CH$_2$)$_q$—C(=O)—$R^{22}$ with q=1, 2, 3, 4 or 5; —C(=O)—O—$R^{23}$; —(CH$_2$)$_r$—C(=O)—O—$R^{24}$ with r=1, 2, 3, 4 or 5; —C(=O)—NHR$^{25}$; —(CH$_2$)$_s$—C(=O)—NHR$^{26}$ with s=1, 2, 3, 4 or 5; a linear or branched, unsubstituted or at least monosubstituted $C_{1-10}$-alkyl residue, $C_{2-6}$-alkenyl residue or $C_{2-6}$-alkynyl residue; a saturated or unsaturated, unsubstituted or at least monosubstituted cycloaliphatic $C_{3-8}$ residue optionally having at least one heteroatom as a ring member, which residue can be bound via a linear or branched, unsubstituted or at least monosubstituted $C_{1-5}$-alkylene group; or an unsubstituted or at least monosubstituted 5- or 6-membered aryl or heteroaryl residue, which can be bound via a linear or branched, unsubstituted or at least monosubstituted $C_{1-5}$-alkylene group and/or can be condensed with an unsubstituted or at least monosubstituted mono- or polycyclic ring system, whereby the rings of the ring system are in each case 5-, 6- or 7-membered, or $R^3$ and $R^4$ together with the nitrogen atom connecting them together as a ring member form a saturated or unsaturated, unsubstituted or at least monosubstituted heterocycloaliphatic $C_{4-10}$ residue optionally having at least one further heteroatom as a ring member which can be condensed with an unsubstituted or at least monosubstituted mono- or polycyclic ring system, whereby the rings of the ring system are in each case 5-, 6- or 7-membered;

$R^5$, $R^6$, $R^7$, $R^8$, $R^{10}$, $R^{11}$, $R^{12}$, $R^{15}$ and $R^{16}$ each independently denote a linear or branched, unsubstituted or at least monosubstituted $C_{1-10}$-alkyl residue, $C_{2-6}$-alkenyl residue or $C_{2-6}$-alkynyl residue; or an unsubstituted or at least monosubstituted 5- to 14-membered aryl or heteroaryl residue, which optionally may be bound via a linear or branched, unsubstituted or at least monosubstituted $C_{1-5}$-alkylene group and/or can be condensed with an unsubstituted or at least monosubstituted mono- or polycyclic ring system, whereby the rings of the ring system are in each case 5-, 6- or 7-membered;

$R^9$, $R^{13}$, $R^{14}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ each independently denote hydrogen; a linear or branched, unsubstituted or at least monosubstituted $C_{1-10}$-alkyl residue, $C_{2-6}$-alkenyl residue or $C_{2-6}$-alkynyl residue; or an unsubstituted or at least monosubstituted 5- to 14-membered aryl or heteroaryl residue, which can be bound via a linear or branched, unsubstituted or at least monosubstituted $C_{1-5}$-alkylene group and/or can be condensed with an unsubstituted or at least monosubstituted mono- or polycyclic ring system, whereby the rings of the ring system are in each case 5-, 6- or 7-membered;

$M^1$ denotes a 5- or 6-membered aryl or heteroaryl residue, which can be substituted with at least one further substituent and can be condensed with an unsubstituted or at least monosubstituted mono- or bicyclic ring system, whereby the rings of the ring system are in each case 5-, 6- or 7-membered, and $M^2$ denotes a 5- or 6-membered aryl or heteroaryl residue, which can be unsubstituted or at least monosubstituted and can be condensed with an unsubstituted or at least monosubstituted mono- or bicyclic ring system, whereby the rings of the ring system are in each case 5-, 6- or 7-membered;

wherein the above-mentioned cycloaliphatic residues optionally may contain 1, 2, 3, 4 or 5 heteroatom(s) as (the) ring member(s) which can in each case mutually independently be selected from the group consisting of nitrogen, oxygen and sulfur, the above-mentioned heterocycloaliphatic residues optionally may contain further 1, 2, 3, 4 or 5 heteroatom(s) as (the) ring member(s) which can in each case mutually independently be selected from the group consisting of nitrogen, oxygen and sulfur, the rings of the mono- or polycyclic ring system have in each case optionally 0, 1, 2 or 3 heteroatom(s) as (the) ring member(s) which are mutually independently selected from the group consisting of oxygen, nitrogen and sulfur; and the above-mentioned heteroaryl residues optionally may contain 1, 2, 3, 4 or 5 heteroatom(s) as (the) ring member(s) which can in each case mutually independently be selected from the group consisting of oxygen, sulfur and nitrogen.

Substituted imidazo[2,1-b]thiazole compounds corresponding to the foregoing formula I are furthermore preferred, in which:

$R^1$ and $R^2$ each independently denote hydrogen; a halogen residue; —NO$_2$; —CN; —NH$_2$; —NHR$^5$; —NR$^6$R$^7$; —NH—C(=O)—R$^8$; —C(=O)—R$^9$, —C(=O)—NH$_2$; —C(=O)—NHR$^{10}$; —C(=O)—NR$^{11}$R$^{12}$; —C(=O)—OR$^{13}$; —(CH$_2$)$_m$—C(=O)—OR$^{14}$ with m=1, 2 or 3; —O—C(=O)—R$^{15}$; —(CH$_2$)$_n$—O—C(=O)—R$^{16}$ with n=1, 2 or 3; —OR$^{17}$; —(CH$_2$)$_o$—O—R$^{18}$ with o=1, 2 or 3; —SR$^{19}$; —(CH$_2$)$_p$—S(=O)$_t$—R$^{20}$ with p=1, 2 or 3 and t=0, 1 or 2; —NH—S(=O)$_2$—NR$^{27}$R$^{28}$; —S(=O)$_2$—NR$^{29}$R$^{30}$; —SF$_5$; —(CH$_2$)$_u$—O—S(=O)$_2$—R$^{31}$ with u=1, 2 or 3; —(CH$_2$)$_v$—O—S(=O)$_2$—O—R$^{32}$ with v=1, 2 or 3; —(CH$_2$)$_w$—O—P(=O)(OR$^{33}$)(OR$^{34}$) with w=1, 2 or 3; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$) and —(CH$_2$)—(CH$_2$)—(CH$_2$)—OH; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl, which in each case can be unsubstituted or substituted with optionally 1, 2, 3 or 4 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, oxo (=O), thioxo (=S), —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C (CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl; or a residue selected from the group consisting of phenyl, benzyl, phenethyl, (3-phenyl)-prop-1-yl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which can in each case be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], (1,3)-dioxolanyl, cyclopropyl, cyclobutyl, cyclopentyl, cyclohexyl, phenyl, furyl (furanyl), thiadiazolyl, thiophenyl (thienyl) and benzyl;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are likewise preferred, in which:

R$^3$ and R$^4$ each independently denote hydrogen; —C(=O)—R$^{21}$; —(CH$_2$)$_q$—C(=O)—R$^{22}$ with q=1, 2 or 3; —C(=O)—O—R$^{23}$; —(CH$_2$)$_r$—C(=O)—O—R$^{24}$ with r=1, 2 or 3; —C(=O)—NHR$^{25}$; —(CH$_2$)$_s$—C(=O)—NHR$^{26}$ with s=1, 2 or 3; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$) and —(CH$_2$)—(CH$_2$)—(CH$_2$)—OH; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl, which in each case can be unsubstituted or substituted with optionally 1, 2, 3 or 4 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, oxo (=O), thioxo (=S), —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl and/or can be bound via a linear or branched C$_{1-3}$-alkylene group; or a residue selected from the group consisting of phenyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡c—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], (1,3)-dioxolanyl, cyclopropyl, cyclobutyl, cyclopentyl, cyclohexyl, phenyl, furyl (furanyl), thiadiazolyl, thiophenyl (thienyl) and benzyl and/or can be bound via a linear or branched $C_{1-3}$-alkylene group; or $R^3$ and $R^4$ together with the nitrogen atom connecting them together as a ring member form a residue selected from the group consisting of imidazolidinyl, piperidinyl, piperazinyl, morpholinyl, pyrrolidinyl, thiomorpholinyl, azepanyl, diazepanyl and azocanyl, which in each case can be unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —OH, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —SF$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH—S(=O)$_2$—CH$_3$, —C(=O)—OH, —C(=O)—H, —C(=O)—CH$_3$, —C(=O)—C$_2$H$_5$, —C(=O)—N(CH$_3$)$_2$, —C(=O)—NH—CH$_3$, —C(=O)—NH$_2$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are likewise preferred, in which:

$R^5$, $R^6$, $R^7$, $R^8$, $R^{10}$, $R^{11}$, $R^{12}$, $R^{15}$ and $R^{16}$ each independently denote a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—NH—CH$_3$, —(CH$_2$)—N(CH$_3$)$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$), —(CH$_2$)—(CH$_2$)—(CH$_2$)—OH, —(CH$_2$)—C(=O)—OH, —(CH$_2$)—C(=O)—O—CH$_3$, —(CH$_2$)—C(=O)—O—C$_2$H$_5$, —(CH$_2$)—(CH$_2$)—C(=O)—OH, —(CH$_2$)—(CH$_2$)—C(=O)—O—CH$_3$ and —(CH$_2$)—(CH$_2$)—C(=O)—O—C$_2$H$_5$; or a residue selected from the group consisting of phenyl, benzyl, phenethyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which can in each case be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are furthermore preferred, in which:

$R^9$, $R^{13}$, $R^{14}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$ $R^{33}$ and $R^{34}$ each independently denote hydrogen; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—NH—CH$_3$, —(CH$_2$)—N(CH$_3$)$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$), —(CH$_2$)—(CH$_2$)—(CH$_2$)—OH, —(CH$_2$)—C(=O)—OH, —(CH$_2$)—C(=O)—O—CH$_3$, —(CH$_2$)—C(=O)—O—C$_2$H$_5$, —(CH$_2$)—(CH$_2$)—C(=O)—OH, —(CH$_2$)—(CH$_2$)—C(=O)—O—CH$_3$ and —(CH$_2$)—(CH$_2$)—C(=O)—O—C$_2$H$_5$; or a residue selected from the group consisting of phenyl, benzyl, phenethyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which can in each case be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are likewise preferred, in which:

M¹ denotes a residue selected from the group consisting of phenyl, furanyl, thiophenyl (thienyl), pyrazolyl, pyrazinyl, pyridazinyl, pyrimidinyl, pyridinyl, pyrrolyl, oxazolyl, isoxazolyl, thiazolyl, thiadiazolyl, imidazolyl, oxadiazolyl, triazolyl, diazinyl, triazinyl, tetrazinyl and tetrazolyl, which can in each case be unsubstituted or substituted with optionally 1, 2, 3 or 4 substituents mutually independently selected from the group consisting of F, Cl, Br, I, —CN, —CH₂—CN, —NO₂, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF₅, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂ and —S—CH₂F;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are furthermore preferred, in which:

M¹ denotes a residue selected from the group consisting of residues 1 to 38,

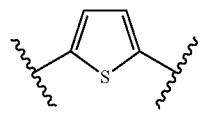
1

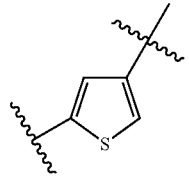
2

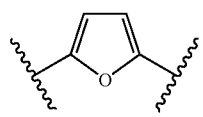
3

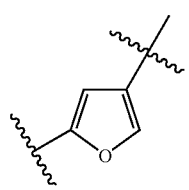
4

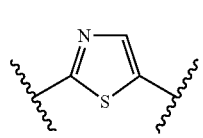
5

-continued

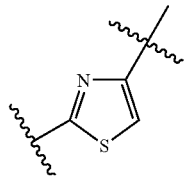
6

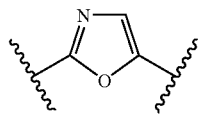
7

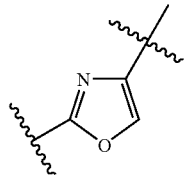
8

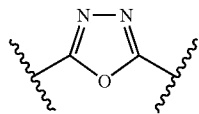
9

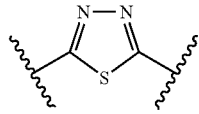
10

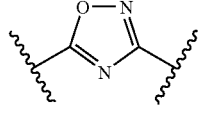
11

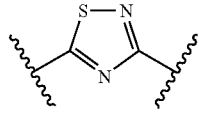
12

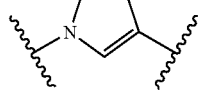
13

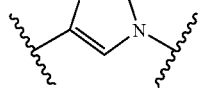
14

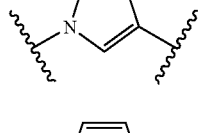
15

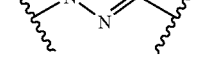
16

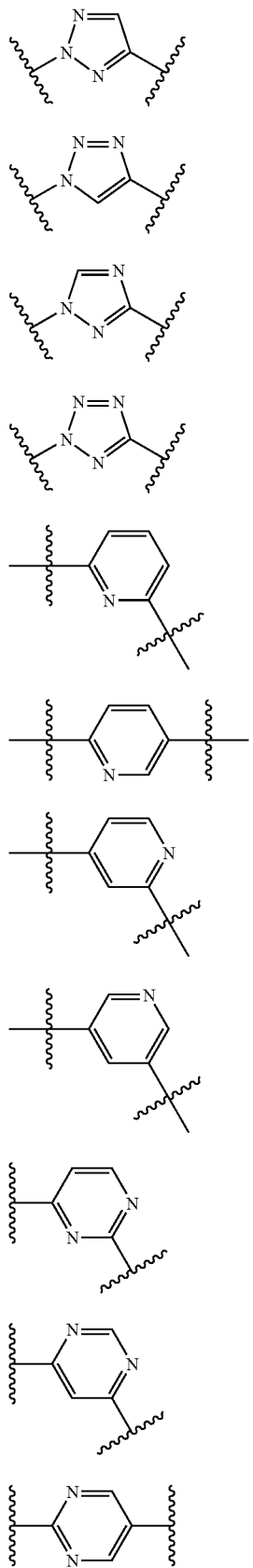
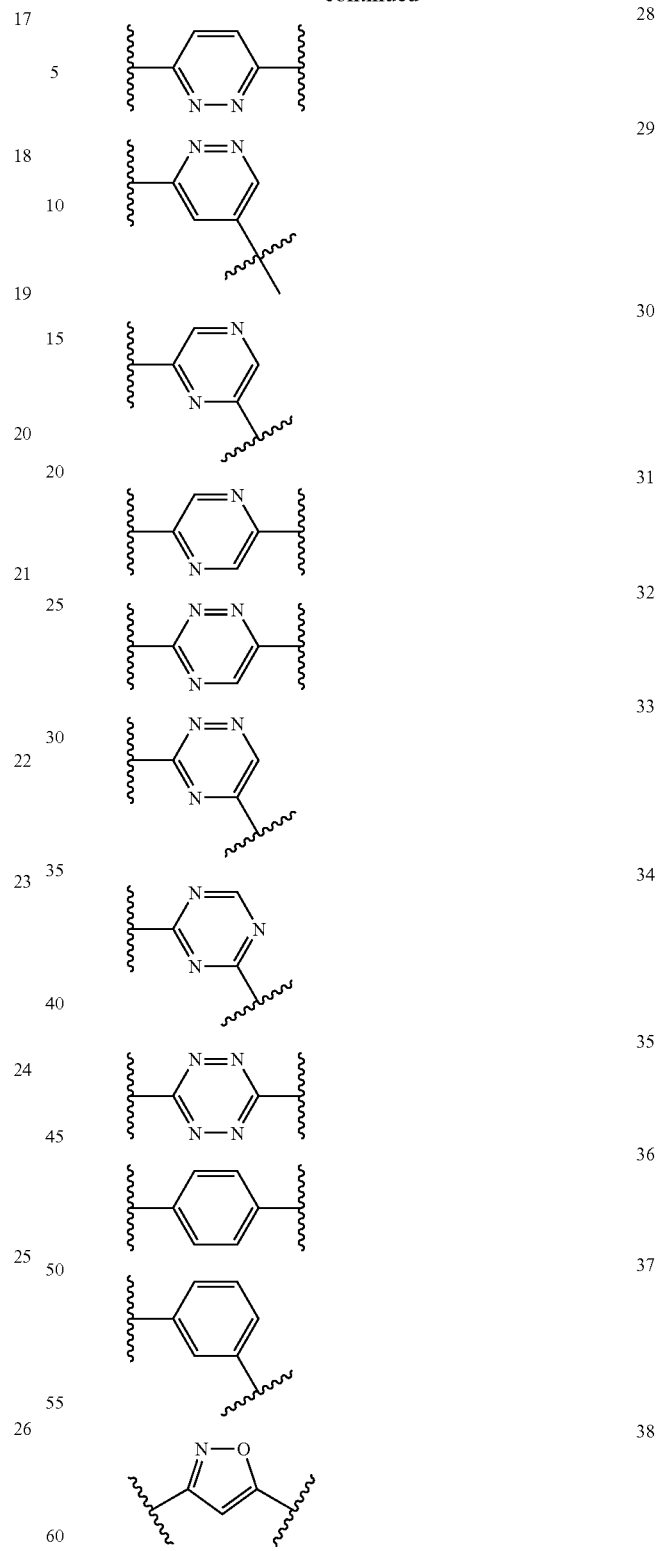
which in each case can be unsubstituted or substituted with optionally 1, 2, 3 or 4 substituents mutually independently selected from the group consisting of F, Cl, Br, I, —CN, —CH$_2$—CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F, and which in each case can be linked in any direction via the positions marked by a wavy line with the bicyclic ring system and the carbon atom of the triple bond;

and each of the remaining residues has the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are furthermore preferred, in which:

M$^2$ denotes a residue selected from the group consisting of phenyl, furanyl, thiophenyl (thienyl), pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—O—CH$_3$, —C(═O)—O—C$_2$H$_5$, —C(═O)—O—C(CH$_3$)$_3$, —C(═O)—H, —C(═O)—CH$_3$, —C(═O)—C$_2$H$_5$, —NH—C(═O)—CH$_3$, —NH—C(═O)—C$_2$H$_5$, —O—C(═O)-phenyl, —C(═O)—NH$_2$, —C(═O)—NH—CH$_3$, —C(═O)—N(CH$_3$)$_2$, —Si(phenyl)$_2$[C(CH$_3$)$_3$], —CH$_2$—NH$_2$, pyrrolyl, —NH—S(═O)$_2$—C$_2$H$_5$, —S(═O)$_2$—NH$_2$, —S(═O)$_2$—NH—CH$_3$, —CH$_2$—OH, —NH—C(═NH)—NH$_2$, —NH—S(═O)$_2$—OH, —S(═O)$_2$—N(CH$_3$)$_2$, (1,3)-dioxolanyl, cyclopropyl, cyclobutyl, cyclopentyl, cyclohexyl, phenyl, furyl (furanyl), thiadiazolyl, thiophenyl (thienyl) and benzyl;

and in each case the remaining residues have the abovementioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are likewise preferred, in which:

M$^2$ denotes a residue selected from the group consisting of residues 1 to 36,

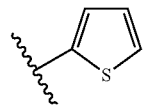

1

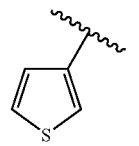

2

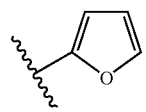

3

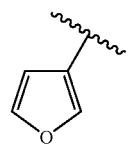

4

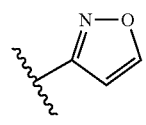

5

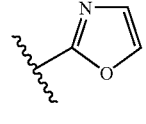

6

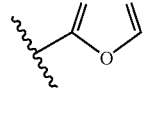

7

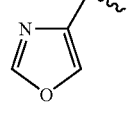

8

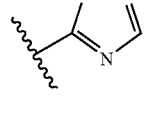

9

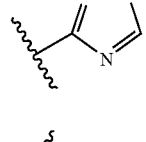

10

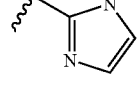

11

-continued
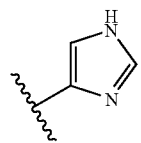
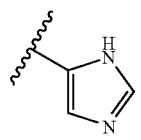
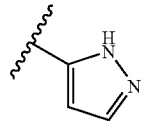
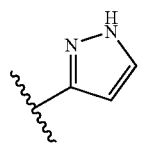
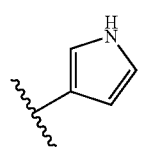
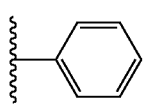
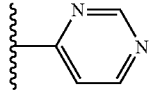
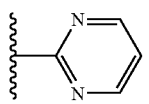
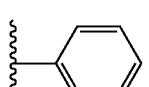
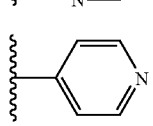
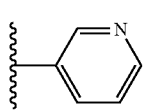
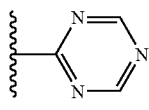
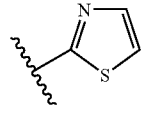
-continued
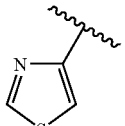
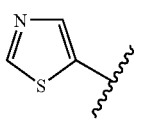
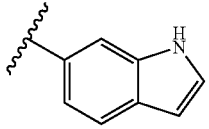
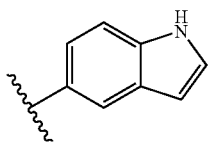
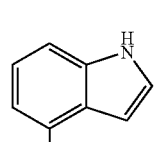
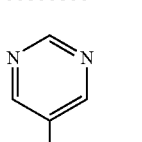
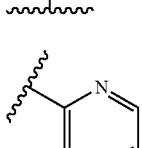
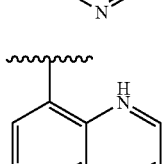
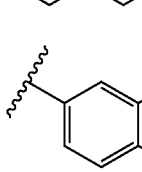

-continued

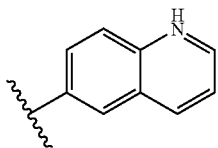

35

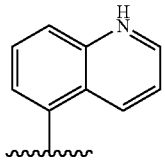

36 which in each case can be linked via the position marked by a wavy line with the carbon atom of the triple bond and can be unsubstituted or substituted with optionally 1, 2, 3, 4 or 5 substituents mutually independently selected from the group consisting of F, Cl, Br, —CN, —$CF_3$, —$SF_5$, —S—$CH_3$, —S—$C_2H_5$, methyl, ethyl, n-propyl, iso-propyl, n-butyl, sec-butyl, iso-butyl, tert-butyl, ethenyl, propenyl, —OH, —O—$CH_3$, —O—$C_2H_5$, —O—$C_3H_7$, —$NH_2$, —$N(CH_3)_2$, —NH—$CH_3$, —$CH_2$—$NH_2$, —$N(C_2H_5)_2$, —$NO_2$, —O—$CF_3$, —S—$CF_3$, —SH, —C(=O)—H, —C(=O)—O—$CH_3$, —C(=O)—O—$C_2H_5$, phenyl, pyrrolyl, (1,3)-dioxolanyl, —Si(phenyl)$_2$[C($CH_3$)$_3$], —C(=O)—$CH_3$, —C(=O)—$C_2H_5$, NH—S(=O)$_2$—$CH_3$, —NH—S(=O)$_2$—$C_2H_5$, —S(=O)$_2$—$NH_2$, —S(=O)$_2$—NH—$CH_3$, —$CH_2$—OH, —C(=O)—OH, —$CH_2$—O—$CH_3$, —C(=O)—$NH_2$, —C(=O)—NH—$CH_3$, —NH—C(=O)—$CH_3$, —NH—C(=NH)—$NH_2$, —NH—S(=O)$_2$—OH and —S(=O)$_2$—N($CH_3$)$_2$;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are particularly preferred, in which:

$R^1$ and $R^2$ each independently denote hydrogen; —F; —Cl; —Br; —I; —$NO_2$; —CN; —$NH_2$; —$NHR^5$; —$NR^6R^7$; —C(=O)—$R^9$, —C(=O)—$NH_2$; —C(=O)—$NHR^{10}$; —C(=O)—$NR^{11}R^{12}$; —C(=O)—$OR^{13}$; —$(CH_2)_m$—C(=O)—$OR^{14}$ with m=1, 2 or 3; —O—C(=O)—$R^{15}$; —$OR^{17}$; —$(CH_2)_o$—O—$R^{18}$ with o=1, 2 or 3; —S(=O)$_2$—$NH_2$; —$SF_5$; —$(CH_2)_u$—O—S(=O)$_2$—$R^{31}$ with u=1, 2 or 3; —$(CH_2)_v$—O—S(=O)$_2$—O—$R^{32}$ with v=1, 2 or 3; —$(CH_2)_w$—O—P(=O)($OR^{33}$)($OR^{34}$) with w=1, 2 or 3; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —$CF_3$, —$CF_2H$, —$CFH_2$, —($CH_2$)—($CF_3$), —($CH_2$)—($CHF_2$), —($CH_2$)—($CH_2F$) and —($CF_2$)—($CF_3$); a residue selected from the group consisting of cyclopropyl, cyclobutyl, cyclopentyl, cyclohexyl, cycloheptyl and cyclooctyl, which in each case can be unsubstituted or substituted with optionally 1, 2, 3 or 4 substituents mutually independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, —OH, oxo (=O), thioxo (=S), —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$ and —O—$CH_2F$; or a residue selected from the group consisting of phenyl, benzyl, phenethyl, (3-phenyl)-prop-1-yl, furyl (furanyl), thienyl (thiophenyl), pyrazolyl, imidazolyl, thiazolyl, thiadiazolyl, pyridinyl, pyridazinyl, pyrimidinyl and pyrazinyl, which in each case can be unsubstituted or substituted with optionally 1, 2, 3, 4 or 5 substituents mutually independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —$SF_5$, —$NH_2$, —C(=O)—OH, —S—$CH_3$, —S—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —C(=O)—O—$CH_3$, —C(=O)—O—$C_2H_5$, —C(=O)—O—C($CH_3$)$_3$, cyclopropyl, cyclobutyl, cyclopentyl, cyclohexyl and phenyl;

$R^3$ and $R^4$ each independently denote hydrogen; —C(=O)—$R^{21}$; —$(CH_2)_q$—C(=O)—$R^{22}$ with q=1, 2 or 3; —C(=O)—O—$R^{23}$; —$(CH_2)_r$—C(=O)—O—$R^{24}$ with r=1, 2 or 3; —C(=O)—$NHR^{25}$; —$(CH_2)_6$—C(=O)—$NHR^{26}$ with s=1, 2 or 3; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; a residue selected from the group consisting of cyclopropyl, cyclobutyl, cyclopentyl, cyclohexyl, cycloheptyl and cyclooctyl, which in each case can be unsubstituted or substituted with optionally 1, 2, 3 or 4 substituents mutually independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, —OH, oxo (=O), thioxo (=S), —O—$CH_3$, —O—$C_2H_5$, —O—$C_3H_7$ and —O—C($CH_3$)$_3$ and/or can be bound via a linear or branched $C_{1-3}$-alkylene group; or a residue selected from the group consisting of phenyl, furyl (furanyl), thienyl (thiophenyl), pyrazolyl, imidazolyl, thiazolyl, thiadiazolyl, pyridinyl, pyridazinyl, pyrimidinyl and pyrazinyl, which in each case can be unsubstituted or substituted with optionally 1, 2, 3, 4 or 5 substituents mutually independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, ethenyl, allyl, —OH, —SH, —$SF_5$, —$NH_2$, —C(=O)—OH, —S—$CH_3$, —S—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —$N(CH_3)_2$, —$N(C_2H_5)_2$, —NH—$CH_3$, —NH—$C_2H_5$, cyclopropyl, cyclobutyl and cyclopentyl and/or can be bound via a linear or branched $C_{1-3}$-alkylene group; or $R^3$ and $R^4$ together with the nitrogen atom connecting them together as a ring member form a residue selected from the group consisting of imidazolidinyl, piperidinyl, piperazinyl, morpholinyl, pyrrolidinyl, thiomorpholinyl, azepanyl, diazepanyl and azocanyl, which in each case can be unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—$CH_3$, —O—$C_2H_5$, —O—$C_3H_7$, —NH₂, —N(CH₃)₂, —N(C₂H₅)₂, —NH—CH₃, —NH—C₂H₅, —NO₂, —CF₃, —O—CF₃, —S—CF₃, —SH, —SF₅, —S—CH₃, —S—C₂H₅, —S(=O)—CH₃, —S(=O)₂—CH₃, —S(=O)—C₂H₅, —S(=O)₂—C₂H₅, —C(=O)—CH₃, —C(=O)—C₂H₅, —C(=O)—N(CH₃)₂, —C(=O)—NH—CH₃, —C(=O)—NH₂, —C(=O)—O—CH₃, —C(=O)—O—C₂H₅, —C(=O)—O—C(CH₃)₃ and phenyl;

$R^5$, $R^6$, $R^7$, $R^{10}$, $R^{11}$, $R^{12}$, $R^{15}$ and $R^{16}$ each independently denote a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF₃, —CF₂H, —CFH₂, —(CH₂)—(CHF₂), —(CH₂)—(CH₂F), —(CF₂)—(CF₃), —(CH₂)—(CH₂)—C(=O)—OH, —(CH₂)—(CH₂)—C(=O)—O—CH₃ and —(CH₂)—(CH₂)—C(=O)—O—C₂H₅; or denote a residue selected from the group consisting of phenyl, benzyl, phenethyl, furyl (furanyl), thienyl (thiophenyl), pyrazolyl, imidazolyl, thiazolyl, thiadiazolyl, pyridinyl, pyridazinyl, pyrimidinyl and pyrazinyl, which in each case can be unsubstituted or substituted with optionally 1, 2, 3, 4 or 5 substituents mutually independently selected from the group consisting of F, Cl, Br, I, —CN, —NO₂, methyl, ethyl, n-propyl, isopropyl, n-butyl, isobutyl, 2-butyl, tert-butyl, n-pentyl, neo-pentyl, —OH, —SH, —SF₅, —NH₂, —C(=O)—OH, —S—CH₃, —S—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F and —C(=O)—CF₃;

$R^9$, $R^{13}$, $R^{14}$, $R^{17}$, $R^{18}$, $R^{21}$, $R^{22}$, $R^{23}$, $R^{24}$, $R^{25}$, $R^{26}$, $R^{31}$, $R^{32}$, $R^{33}$ and $R^{34}$ each independently denote hydrogen; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF₃, —CF₂H, —CFH₂, —(CH₂)—(CF₃), —(CH₂)—(CHF₂), —(CH₂)—(CH₂F) and —(CF₂)—(CF₃); or a residue selected from the group consisting of phenyl, benzyl, phenethyl, furyl (furanyl), thienyl (thiophenyl), pyrazolyl, imidazolyl, thiazolyl, thiadiazolyl, pyridinyl, pyridazinyl, pyrimidinyl and pyrazinyl, which in each case can be unsubstituted or substituted with optionally 1, 2, 3, 4 or 5 substituents independently selected from the group consisting of F, Cl, Br, I, —CN, —NO₂, methyl, ethyl, n-propyl, isopropyl, n-butyl, isobutyl, 2-butyl, tert-butyl, n-pentyl, neo-pentyl, —OH, —SH, —SF₅, —NH₂, —C(=O)—OH, —S—CH₃, —S—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F and —C(=O)—CF₃;

$M^1$ denotes a residue selected from the group consisting of residues 1 to 9, 11, 21, 22 and 36 to 38, 1
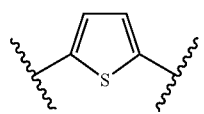

-continued

2
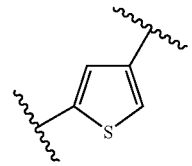

3
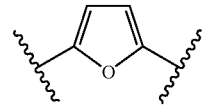

4
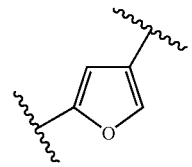

5
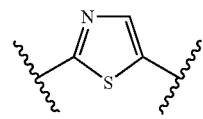

6

7
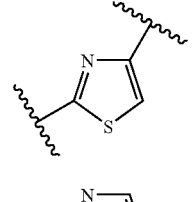

8
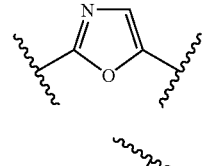

9
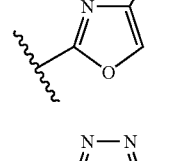

11
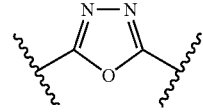

21
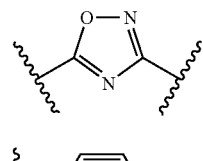

22
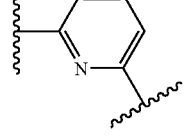

-continued

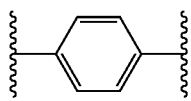
36

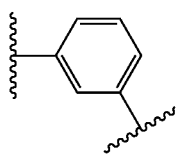
37

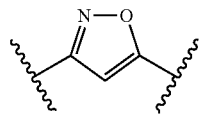
38 which in each case can be unsubstituted or substituted with optionally 1 or 2 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F, and which in each case can be linked in any direction via the positions marked by a wavy line with the bicyclic ring system and the carbon atom of the triple bond; and M$^2$ denotes a residue selected from the group consisting of residues 1 to 36,

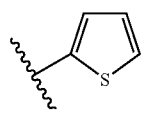
1

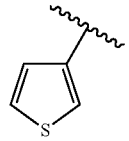
2

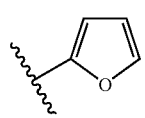
3

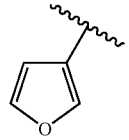
4

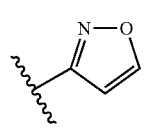
5

-continued

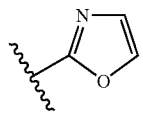
6

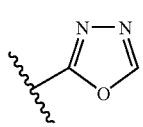
7

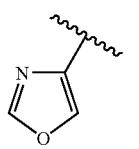
8

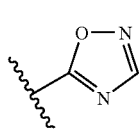
9

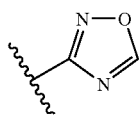
10

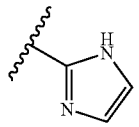
11

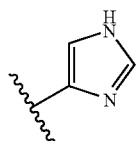
12

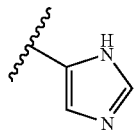
13

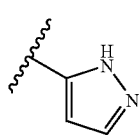
14

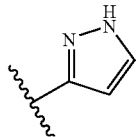
15

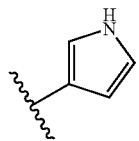
16

-continued

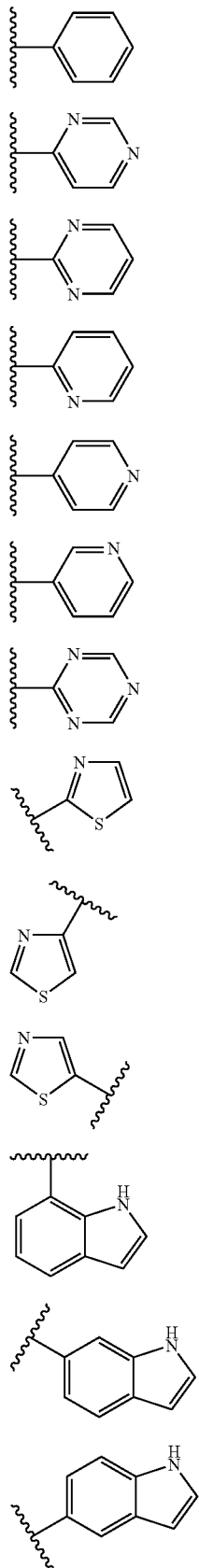

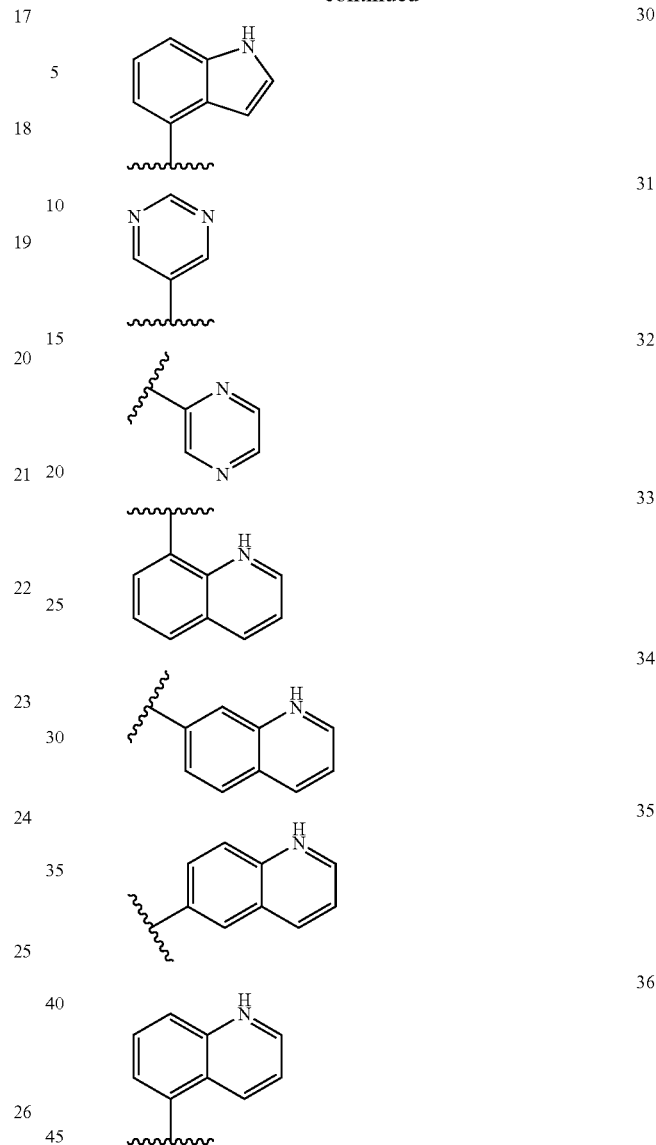

which in each case can be linked via the position marked by a wavy line with the carbon atom of the triple bond and can be unsubstituted or substituted with optionally 1, 2, 3, 4 or 5 substituents mutually independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-di-oxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted imidazo[2,1-b]thiazole compounds corresponding to the foregoing formula I are very particularly preferred, in which:

$R^1$ and $R^2$ each independently denote hydrogen; —F; —Cl; —Br; —I; —NO$_2$; —CN; —NHR$^5$; —NR$^6$R$^7$; —C(=O)—R$^9$, —C(=O)—OR$^{13}$; —(CH$_2$)—O—C(=O)—R$^{16}$; —OR$^{17}$; —(CH$_2$)—O—S(=O)$_2$—R$^{31}$; —(CH$_2$)—O—S(=O)$_2$—O—R$^{32}$; —(CH$_2$)—O—P(=O)(OR$^{33}$)(OR$^{34}$); —SF$_5$; a residue selected from the group consisting of methyl, ethyl, n-propyl, isopropyl, n-butyl, isobutyl, 2-butyl, tert-butyl, n-pentyl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); a residue selected from the group consisting of cyclopropyl, cyclobutyl, cyclopentyl, cyclohexyl, cycloheptyl and cyclooctyl; or a residue selected from the group consisting of phenyl, benzyl, phenethyl and (3-phenyl)-prop-1-yl, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F;

$R^3$ and $R^4$ each independently denote hydrogen; —C(=O)—R$^{21}$; —(CH$_2$)$_q$—C(=O)—R$^{22}$ with q=1, 2 or 3; —(CH$_2$)$_r$—C(=O)—O—R$^2$ with r=1, 2 or 3; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; a residue selected from the group consisting of cyclopropyl, cyclobutyl, cyclopentyl, cyclohexyl, cycloheptyl and cyclooctyl, which can be bound via a —(CH$_2$)—, —(CH$_2$)$_2$—, —(CH(CH$_3$))— or —(CH$_2$)$_3$ group; or a residue selected from the group consisting of phenyl, furyl (furanyl), thienyl (thiophenyl), pyridinyl, pyridazinyl, pyrimidinyl and pyrazinyl, which in each case can be unsubstituted or substituted with optionally 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F and/or can be bound via a —(CH$_2$)—, —(CH$_2$)$_2$—, —(CH(CH$_3$))— or —(CH$_2$)$_3$ group; or $R^3$ and $R^4$ together with the nitrogen atom connecting them together as a ring member form a residue selected from the group consisting of piperidinyl, piperazinyl, morpholinyl and pyrrolidinyl, which in each case can be unsubstituted or substituted with optionally 1, 2, 3, 4 or 5 substituents mutually independently selected from the group consisting of methyl, ethyl, n-propyl, isopropyl, n-butyl, 2-butyl, isobutyl, tert-butyl, —S(=O)—CH$_3$, —S(=O)$_2$—CH$_3$, —S(=O)—C$_2$H$_5$, —S(=O)$_2$—C$_2$H$_5$, —C(=O)—CH$_3$, —C(=O)—C$_2$H$_5$, —C(=O)—N(CH$_3$)$_2$, —C(=O)—NH—CH$_3$, —C(=O)—NH$_2$, —C(=O)—O—CH$_3$, —C(=O)—O—C$_2$H$_5$ and —C(=O)—O—C(CH$_3$)$_3$;

$R^5$, $R^6$, $R^7$ and $R^{16}$ each independently denote a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CHF$_2$), —(CH$_2$)—(CH$_2$F), —(CF$_2$)—(CF$_3$), —(CH$_2$)—(CH$_2$)—C(=O)—OH; —(CH$_2$)—(CH$_2$)—C(=O)—O—CH$_3$ and —(CH$_2$)—(CH$_2$)—C(=O)—O—C$_2$H$_5$; or a residue selected from the group consisting of phenyl, benzyl and phenethyl, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$ and —O—C$_2$H$_5$;

$R^9$, $R^{13}$, $R^{17}$, $R^{21}$, $R^{22}$, $R^{24}$, $R^{31}$, $R^{32}$, $R^{33}$ and $R^{34}$ each independently denote hydrogen; a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); or a residue selected from the group consisting of phenyl, benzyl and phenethyl, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$ and —O—C$_2$H$_5$;

$M^1$ denotes a residue selected from the group consisting of residues 1 to 6, 21, 22, 36 and 37,

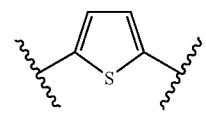

1

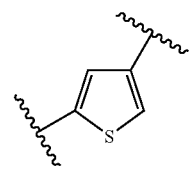

2

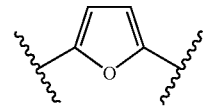

3

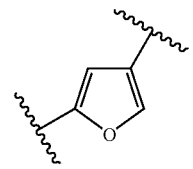

4

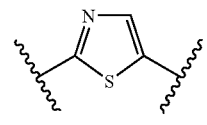

5

-continued

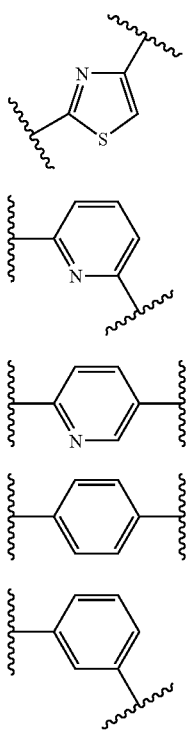

which in each case can be unsubstituted or substituted with optionally 1 or 2 substituents mutually independently selected from the group consisting of F, Cl, Br, I, —CN, —CH₂—CN, —NO₂, methyl, ethyl, n-propyl, isopropyl, n-butyl, isobutyl, 2-butyl, tert-butyl, n-pentyl, neo-pentyl, —SF₅, —O—CH₃, —O—C₂H₅, —O—C₃H₇, —O—C(CH₃)₃, —CF₃, —CHF₂, —CH₂F, —O—CF₃, —O—CHF₂ and —O—CH₂F, and which in each case can be linked in any direction via the positions marked by a wavy line with the bicyclic ring system and the carbon atom of the triple bond; and M² denotes a residue selected from the group consisting of phenyl, 2-pyridinyl, 3-pyridinyl, 4-pyridinyl, 2-thiazolyl, 4-thiazolyl, 5-thiazolyl, 4-indolyl, 5-indolyl, 6-indolyl, 7-indolyl, 2-thiophenyl (2-thienyl), 3-thiophenyl (3-thienyl), 2-imidazolyl, 4-imidazolyl, 5-imidazolyl, 2-pyrimidinyl, 4-pyrimidinyl, 5-pyrimidinyl, 2-pyrazinyl, 5-quinolinyl, 6-quinolinyl, 7-quinolinyl and 8-quinolinyl, which in each case can be unsubstituted or substituted with optionally 1, 2, 3, 4 or 5 substituents mutually independently selected from the group consisting of F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred are substituted imidazo[2,1-b]thiazole compounds corresponding to formula Ia

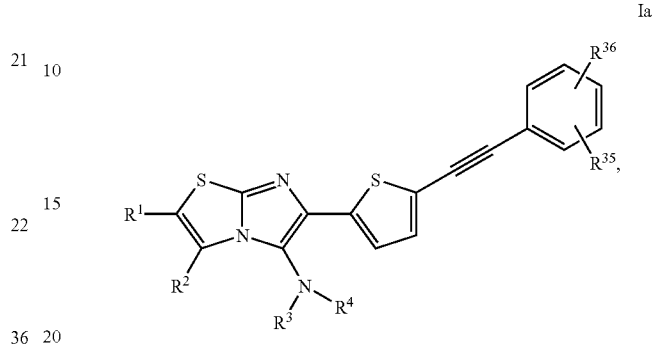

in which

R¹, R², R³ and R⁴ have the above-mentioned meanings, and R³⁵ and R³⁶ each independently denote a residue selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂;

in each case optionally in the form of corresponding salts, or in each case optionally in the form of corresponding solvates.

Likewise very particularly preferred are substituted imidazo[2,1-b]thiazole compounds corresponding to formula Ib

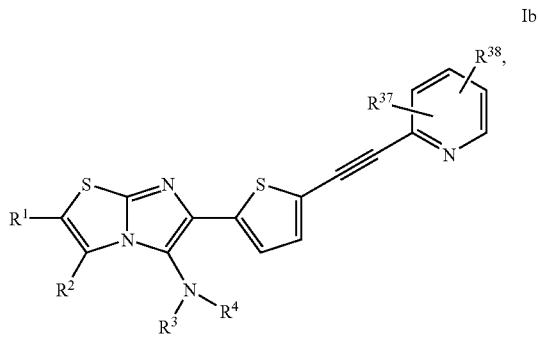

in which

R¹, R², R³ and R⁴ have the above-mentioned meanings, and R³⁷ and R³⁸ each independently denote a residue selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—

$C_2H_5$, phenyl, pyrrolyl, (1,3)-dioxolanyl, —Si(phenyl)$_2$[C(CH$_3$)$_3$], —C(═O)—CH$_3$, —C(═O)—C$_2$H$_5$, NH—S(═O)$_2$—CH$_3$, —NH—S(═O)$_2$—C$_2$H$_5$, —S(═O)$_2$—NH$_2$, —S(═O)$_2$—NH—CH$_3$, —CH$_2$—OH, —C(═O)—OH, —CH$_2$—O—CH$_3$, —C(═O)—NH$_2$, —C(═O)—NH—CH$_3$, —NH—C(═O)—CH$_3$, —NH—C(═NH)—NH$_2$, —NH—S(═O)$_2$—OH and —S(═O)$_2$—N(CH$_3$)$_2$;

in each case optionally in the form of corresponding salts, or in each case optionally in the form of corresponding solvates.

Likewise very particularly preferred are substituted imidazo[2,1-b]thiazole compounds corresponding to formula Ic Ic

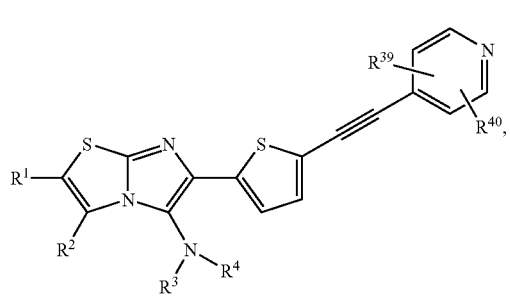

in which $R^1$, $R^2$, $R^3$ and $R^4$ have the above-mentioned meanings, and $R^{39}$ and $R^{40}$ each independently denote a residue selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(═O)—H, —C(═O)—O—CH$_3$, —C(═O)—O—C$_2$H$_5$, phenyl, pyrrolyl, (1,3)-dioxolanyl, —Si(phenyl)$_2$[C(CH$_3$)$_3$], —C(═O)—CH$_3$, —C(═O)—C$_2$H$_5$, NH—S(═O)$_2$—CH$_3$, —NH—S(═O)$_2$—C$_2$H$_5$, —S(═O)$_2$—NH$_2$, —S(═O)$_2$—NH—CH$_3$, —CH$_2$—OH, —C(═O)—OH, —CH$_2$—O—CH$_3$, —C(═O)—NH$_2$, —C(═O)—NH—CH$_3$, —NH—C(═O)—CH$_3$, —NH—C(═NH)—NH$_2$, —NH—S(═O)$_2$—OH and —S(═O)$_2$—N(CH$_3$)$_2$;

in each case optionally in the form of corresponding salts, or in each case optionally in the form of corresponding solvates.

Likewise very particularly preferred are substituted imidazo[2,1-b]thiazole compounds corresponding to formula Id Id

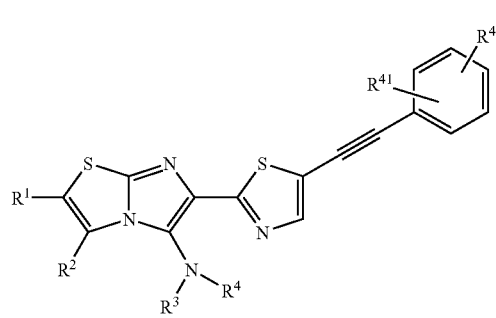

in which $R^1$, $R^2$, $R^3$ and $R^4$ have the above-mentioned meanings, and $R^{41}$ and $R^{42}$ each independently denote a residue selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(═O)—H, —C(═O)—O—CH$_3$, —C(═O)—O—C$_2$H$_5$, phenyl, pyrrolyl, (1,3)-dioxolanyl, —Si(phenyl)$_2$[C(CH$_3$)$_3$], —C(═O)—CH$_3$, —C(═O)—C$_2$H$_5$, NH—S(═O)$_2$—CH$_3$, —NH—S(═O)$_2$—C$_2$H$_5$, —S(═O)$_2$—NH$_2$, —S(═O)$_2$—NH—CH$_3$, —CH$_2$—OH, —C(═O)—OH, —CH$_2$—O—CH$_3$, —C(═O)—NH$_2$, —C(═O)—NH—CH$_3$, —NH—C(═O)—CH$_3$, —NH—C(═NH)—NH$_2$, —NH—S(═O)$_2$—OH and —S(═O)$_2$—N(CH$_3$)$_2$;

in each case optionally in the form of corresponding salts, or in each case optionally in the form of corresponding solvates.

Likewise very particularly preferred are substituted imidazo[2,1-b]thiazole compounds corresponding to formula Ie Ie

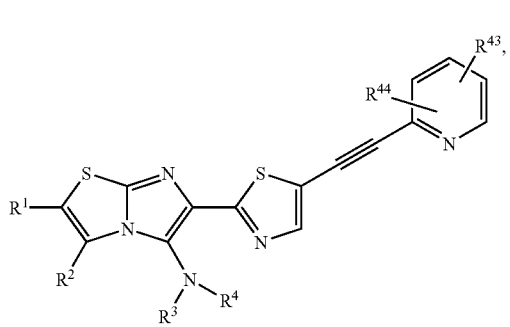

in which $R^1$, $R^2$, $R^3$ and $R^4$ have the above-mentioned meanings, and $R^{43}$ and $R^{44}$ each independently denote a residue selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(═O)—H, —C(═O)—O—CH$_3$, —C(═O)—O—C$_2$H$_5$, phenyl, pyrrolyl, (1,3)-dioxolanyl, —Si(phenyl)$_2$[C(CH$_3$)$_3$], —C(═O)—CH$_3$, —C(═O)—C$_2$H$_5$, NH—S(═O)$_2$—CH$_3$, —NH—S(═O)$_2$—C$_2$H$_5$, —S(═O)$_2$—NH$_2$, —S(═O)$_2$—NH—CH$_3$, —CH$_2$—OH, —C(═O)—OH, —CH$_2$—O—CH$_3$, —C(═O)—NH$_2$, —C(═O)—NH—CH$_3$, —NH—C(═O)—CH$_3$, —NH—C(═NH)—NH$_2$, —NH—S(═O)$_2$—OH and —S(═O)$_2$—N(CH$_3$)$_2$;

in each case optionally in the form of corresponding salts, or in each case optionally in the form of corresponding solvates.

Likewise very particularly preferred are substituted imidazo[2,1-b]thiazole compounds corresponding to formula If If

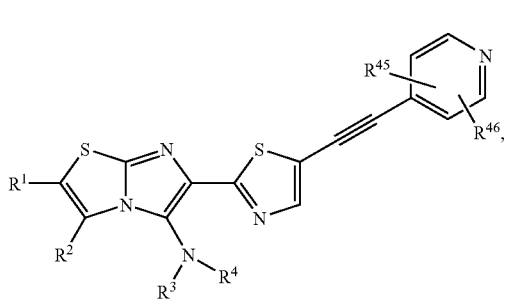

in which
R¹, R², R³ and R⁴ have the above-mentioned meanings, and R⁴⁵ and R⁴⁶ each independently denote a residue selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂;

in each case optionally in the form of corresponding salts, or in each case optionally in the form of corresponding solvates.

Likewise very particularly preferred are substituted imidazo[2,1-b]thiazole compounds corresponding to formula Ig Ig

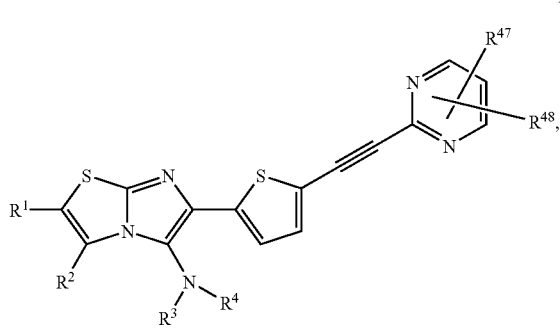

in which
R¹, R², R³ and R⁴ have the above-mentioned meanings, and R⁴⁷ and R⁴⁸ each independently denote a residue selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂;

in each case optionally in the form of corresponding salts, or in each case optionally in the form of corresponding solvates.

Likewise very particularly preferred are substituted imidazo[2,1-b]thiazole compounds corresponding to formula Ih Ih

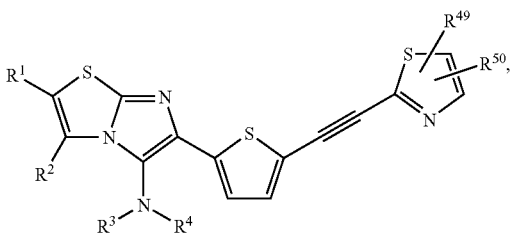

in which
R¹, R², R³ and R⁴ have the above-mentioned meanings, and R⁴⁹ and R⁵⁰ each independently denote a residue selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂;

in each case optionally in the form of corresponding salts, or in each case optionally in the form of corresponding solvates.

Even further preferred are substituted imidazo[2,1-b]thiazole compounds corresponding to the foregoing formulas Ia, Ib, Ic, Id, Ie, If, Ig and Ih, in which
R¹ denotes hydrogen; —F; —Cl; —Br; —CN; —C(=O)—OR¹³; or a residue selected from the group consisting of methyl, ethyl, n-propyl, isopropyl, n-butyl, isobutyl, 2-butyl, tert-butyl and n-pentyl;
R² denotes hydrogen; —F; —Cl; —Br; —CN; —C(=O)—OR¹³; or a residue selected from the group consisting of methyl, ethyl, n-propyl, isopropyl, n-butyl, isobutyl, 2-butyl, tert-butyl and n-pentyl;
R³ denotes hydrogen;
R⁴ denotes hydrogen; —C(=O)—R²¹ or a residue selected from the group consisting of methyl, ethyl, n-propyl, isopropyl, n-butyl, isobutyl, 2-butyl, tert-butyl, n-pentyl and (2,4,4)-trimethyl-pent-2-yl;
R¹³ denotes a residue selected from the group consisting of methyl, ethyl, n-propyl, isopropyl, n-butyl, isobutyl, 2-butyl, tert-butyl, n-pentyl, 2-pentyl, 3-pentyl and (2,4,4)-trimethyl-pent-2-yl;
R²¹ denotes a residue selected from the group consisting of methyl, ethyl, n-propyl, isopropyl, n-butyl, isobutyl, 2-butyl, tert-butyl, n-pentyl and (2,4,4)-trimethyl-pent-2-yl or a phenyl residue which is in each case unsubstituted; and $R^{35}, R^{36}, R^{37}, R^{38}, R^{39}, R^{40}, R^{41}, R^{42}, R^{43}, R^{44}, R^{45}, R^{46}, R^{47}, R^{48}, R^{49}$ and $R^{50}$ each independently denote a residue selected from the group consisting of F, Cl, Br, —CN, —OH, —CF$_3$, methyl, ethyl, n-propyl, iso-propyl, n-butyl, sec-butyl, iso-butyl and tert-butyl;

in each case optionally in the form of corresponding salts, or in each case optionally in the form of corresponding solvates.

Substituted imidazo[2,1-b]thiazole compounds corresponding to the foregoing formula I are likewise very particularly preferred, in which $R^1$ denotes hydrogen; —F; —Cl; —Br; —CN; —O—CH$_3$; —C(=O)—R$^9$, —C(=O)—OR$^{13}$; —(CH$_2$)—O—C(=O)—R$^{16}$; —(CH$_2$)—O—S(=O)$_2$—R$^{31}$; —(CH$_2$)—O—S(=O)$_2$—O—R$^{32}$; —(CH$_2$)—O—P(=O)(OR$^{33}$)(OR$^{34}$); or a residue selected from the group consisting of methyl, ethyl, n-propyl, isopropyl, n-butyl, isobutyl, 2-butyl, tert-butyl, n-pentyl, —CF$_3$, —CF$_2$H, —CFH$_2$, —(CH$_2$)—(CF$_3$), —(CH$_2$)—(CHF$_2$), —(CH$_2$)—(CH$_2$F), and —(CF$_2$)—(CF$_3$);

$R^2$ denotes hydrogen; —F; —Cl; —Br; —CN; —O—CH$_3$; —C(=O)—R$^9$, —C(=O)—OR$^{13}$; —(CH$_2$)—O—C(=O)—R$^{16}$; —(CH$_2$)—O—S(=O)$_2$—R$^{31}$; —(CH$_2$)—O—S(=O)$_2$—O—R$^{32}$; —(CH$_2$)—O—P(=O)(OR$^{33}$)(OR$^{34}$); or a residue selected from the group consisting of methyl, ethyl, n-propyl, isopropyl, n-butyl, isobutyl, 2-butyl, tert-butyl, n-pentyl, —CF$_3$, —CF$_2$H, —CFH$_2$, —(CH$_2$)—(CF$_3$), —(CH$_2$)—(CHF$_2$), —(CH$_2$)—(CH$_2$F), and —(CF$_2$)—(CF$_3$);

$R^3$ denotes hydrogen or a residue selected from the group consisting of methyl, ethyl and isopropyl;

$R^4$ denotes hydrogen; —C(=O)—R$^{21}$ or a residue selected from the group consisting of methyl, ethyl, n-propyl, iso-propyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; or $R^3$ and $R^4$ together with the nitrogen atom connecting them together as a ring member form a residue selected from the group consisting of pyrrolidinyl, piperidinyl and morpholinyl;

$R^{16}$ denotes a residue selected from the group consisting of —(CH$_2$)—(CH$_2$)—C(=O)—OH; —(CH$_2$)—(CH$_2$)—C(=O)—O—CH$_3$ and —(CH$_2$)—(CH$_2$)—C(=O)—O—C$_2$H$_5$;

$R^9$, $R^{13}$, $R^{31}$, $R^{32}$, $R^{33}$ and $R^{34}$ each independently denote hydrogen; or a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$);

$R^{21}$ denotes a residue selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$) or a phenyl residue, which in each case can be unsubstituted or substituted with optionally 1, 2, 3, 4 or 5 substituents mutually independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$ and —O—C$_2$H$_5$;

$M^1$ denotes a residue selected from the group consisting of residues 1, 3, 5, 36 and 37,

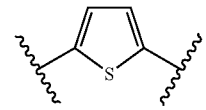

1

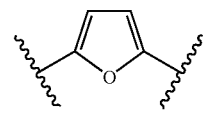

3

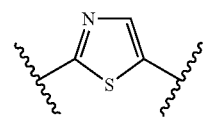

5

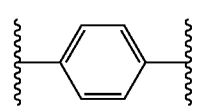

36

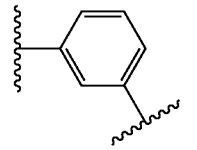

37 which in each case is unsubstituted, and which in each case can be linked in any direction via the positions marked by a wavy line with the bicyclic ring system and the carbon atom of the triple bond;

$M^2$ denotes a residue selected from the group consisting of phenyl, 2-pyrimidinyl, 5-pyrimidinyl, 2-thiophenyl (2-thienyl), 3-thiophenyl (3-thienyl), 2-pyridinyl, 3-pyridinyl, 4-pyridinyl, 2-thiazolyl and 4-thiazolyl, which in each case can be unsubstituted or substituted with optionally 1, 2, 3, 4 or 5 substituents mutually independently selected from the group consisting of F, Cl, Br, —CN, —O—CH$_3$, —OH, —CF$_3$, methyl, ethyl, n-propyl, iso-propyl, n-butyl, sec-butyl, iso-butyl and tert-butyl;

in each case optionally in the form of corresponding salts, or in each case optionally in the form of corresponding solvates.

Substituted imidazo[2,1-b]thiazole compounds corresponding to the foregoing formula I are likewise very particularly preferred, in which $R^1$ denotes hydrogen; —F; —Cl; —Br; —CN; —C(=O)—OR$^{13}$; or a residue selected from the group consisting of methyl, ethyl, n-propyl, isopropyl, n-butyl, isobutyl, 2-butyl, tert-butyl and n-pentyl;

$R^2$ denotes hydrogen; —F; —Cl; —Br; —CN; —C(=O)—OR$^{13}$; or a residue selected from the group consisting of methyl, ethyl, n-propyl, isopropyl, n-butyl, isobutyl, 2-butyl, tert-butyl and n-pentyl;

$R^3$ denotes hydrogen;

$R^4$ denotes hydrogen; —C(=O)—R$^{21}$ or a residue selected from the group consisting of methyl, ethyl, n-propyl, iso-propyl, n-butyl, isobutyl, 2-butyl, tert-butyl, n-pentyl and (2,4,4)-trimethyl-pent-2-yl;

$R^{13}$ denotes a residue selected from the group consisting of methyl, ethyl, n-propyl, isopropyl, n-butyl, isobutyl, 2-butyl, tert-butyl, n-pentyl, 2-pentyl, 3-pentyl and (2,4,4)-trimethyl-pent-2-yl;

$R^{21}$ denotes a residue selected from the group consisting of methyl, ethyl, n-propyl, isopropyl, n-butyl, isobutyl, 2-butyl, tert-butyl, n-pentyl and (2,4,4)-trimethyl-pent-2-yl or a phenyl residue which in each case is unsubstituted;

$M^1$ denotes a residue selected from the group consisting of residues 1, 3, 5 and 22,

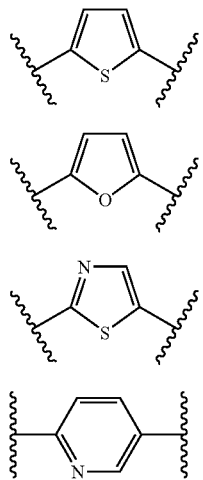

which in each case is unsubstituted, and which in each case can be linked in any direction via the positions marked by a wavy line with the bicyclic ring system and the carbon atom of the triple bond; and $M^2$ denotes a residue selected from the group consisting of phenyl, 2-pyrimidinyl, 5-pyrimidinyl, 2-thiophenyl (2-thienyl), 3-thiophenyl (3-thienyl), 2-pyridinyl, 3-pyridinyl, 4-pyridinyl, 2-thiazolyl and 4-thiazolyl, which in each case can be unsubstituted or substituted with optionally 1, 2, 3, 4 or 5 substituents mutually independently selected from the group consisting of F, Cl, Br, —CN, —O—CH$_3$, —OH, —CF$_3$, methyl, ethyl, n-propyl, iso-propyl, n-butyl, sec-butyl, iso-butyl and tert-butyl;

in each case optionally in the form of corresponding salts, or in each case in the form of corresponding solvates.

Substituted imidazo[2,1-b]thiazole compounds corresponding to the foregoing formula I are still further preferably selected from the group consisting of:

[1] 6-(5-(phenylethynyl)thiophene-2-yl)-N-(2,4,4-trimethyl-pentane-2-yl)-imidazo[2,1-b]thiazole-5-amine,
[2] N-tert-butyl-6-(5-(pyridine-2-ylethynyl)thiophene-2-yl)-imidazo[2,1-b]thiazole-5-amine,
[3] N-tert-butyl-3-methyl-6-(5-(pyridine-2-ylethynyl)thiophene-2-yl)-imidazo[2,1-b]thiazole-5-amine hydrochloride,
[4] N-tert-butyl-2-methyl-6-(5-(pyridine-2-ylethynyl)thiophene-2-yl)-imidazo[2,1-b]thiazole-5-amine,
[5] N-tert-butyl-2,3-dimethyl-6-(5-(pyridine-2-ylethynyl)thiophene-2-yl)-imidazo[2,1-b]thiazole-5-amine hydrochloride,
[6] N-tert-butyl-2-chloro-6-(5-(pyridine-2-ylethynyl)thiophene-2-yl)-imidazo[2,1-b]thiazole-5-amine hydrochloride,
[7] N-tert-butyl-6-(5-(pyridine-4-ylethynyl)thiophene-2-yl)imidazo[2,1-b]thiazole-5-amine,
[8] 5-(tert-butylamino)-6-(5-(pyridine-2-ylethynyl)thiophene-2-yl)-imidazo[2,1-b]thiazole-2-carboxylic acid methylester hydrochloride and
[9] N-tert-butyl-6-(5-(pyridine-2-ylethynyl)thiazole-2-yl)imidazo[2,1-b]thiazole-5-amine;
[10] 6-(5-pyridine-2-ylethynyl)thiophene-2-yl)-N-(2,4,4-trimethylpentane-2-yl)imidazo[2,1-b]thiazole-5-amine,
[11] N-tert-butyl-2-methyl-6-(4-(pyridine-2-ylethynyl)phenyl)imidazo[2,1-b]thiazole-5-amine,
[12] N-tert-butyl-6-(5-(pyridine-2-ylethynyl)furan-2-yl)imidazo[2,1-b]thiazole-5-amine,
[13] N-tert-butyl-3-methyl-6-(5-(phenylethynyl)thiophene-2-yl)imidazo[2,1-b]thiazole-5-amine,
[14] 6-(5-(pyridine-2-ylethynyl)thiophene-2-yl)imidazo[2,1-b]thiazole-5-amine,
[15] N-tert-butyl-6-(5-(pyrimidine-2-ylethynyl)thiophene-2-yl)imidazo[2,1-b]thiazole-5-amine,
[16] N-tert-butyl-6-(5-((3-fluoropyridine-2-yl)ethynyl)thiophene-2-yl)imidazo[2,1-b]thiazole-5-amine,
[17] N-tert-butyl-6-(5-((2-fluoropyridine-4-yl)ethynyl)thiophene-2-yl)imidazo[2,1-b]thiazole-5-amine,
[18] N-tert-butyl-6-(5-(thiophene-2-ylethynyl)thiophene-2-yl)imidazo[2,1-b]thiazole-5-amine,
[19] N-tert-butyl-6-(5-(thiazole-2-ylethynyl)thiophene-2-yl)imidazo[2,1-b]thiazole-5-amine,
[20] 3-((5-(5-(tert-butylamino)imidazo[2,1-b]thiazole-6-yl)thiophene-2-yl)ethynyl)phenol,
[21] 3-((5-(5-(tert-butylamino)imidazo[2,1-b]thiazole-6-yl)thiophene-2-yl)ethynyl)benzonitrile,
[22] N-ethyl-6-(6-(phenylethynyl)pyridine-3-yl)imidazo[2,1-b]thiazole-5-amine,
[23] N-tert-butyl-6-(5-((3-methylpyridine-2-yl)ethynyl)thiophene-2-yl)imidazo[2,1-b]thiazole-5-amine,
[24] N-(6-(5-(pyridine-2-ylethynyl)thiophene-2-yl)imidazo[2,1-b]thiazole-5-yl)acetamide, and
[25] N-(6-(5-(pyridine-2-ylethynyl)thiophene-2-yl)imidazo[2,1-b]thiazole-5-yl)benzamide;

in each case optionally in the form of corresponding salts, or in each case in the form of corresponding solvates.

Substituted imidazo[2,1-b]thiazole compounds corresponding to the foregoing formula I are likewise particularly preferred, which, after 60 minutes of incubation in 450 μg protein from pig brain homogenate at a temperature between 20° C. and 25° C. in a concentration of less than 2500 nM, preferably less than 1000 nM, particularly preferably less than 700 nM, very particularly preferably less than 100 nM, even more preferably less than 70 nM, bring about a 50-percent displacement of [$^3$H]-2-methyl-6-(3-methoxyphenyl)-ethynylpyridine which is present in a concentration of 5 nM. The determination of the displacement of [$^3$H]-2-methyl-6-(3-methoxyphenyl)-ethynyl-pyridine is performed as described hereinafter in the section Pharmacological Methods, I. Method for determining the inhibition of [$^3$H]-MPEP-bonding in the mGluR5 receptor bonding assay.

The invention further relates to method for producing compounds corresponding to the foregoing formula I, comprising: reacting a compound corresponding to formula II

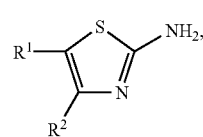

wherein $R^1$ and $R^2$ have the meanings indicated above, in a reaction medium, optionally in the presence of at least one organic or inorganic acid or at least one transition metal salt, with an isocyanide corresponding to formula III

III in which $R^3$ has the meaning indicated above, and with an aldehyde corresponding to formula IV

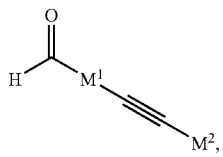
IV in which $M^1$ and $M^2$ have the meanings indicated above, to yield a compound corresponding to formula V,

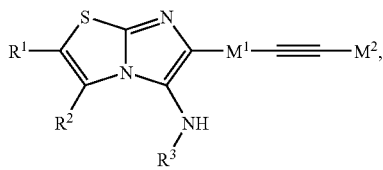
V in which $R^1$, $R^2$, $R^3$, $M^1$ and $M^2$ have the above-mentioned meanings, and optionally purifying and/or isolating the compound of formula V, and optionally transforming the compound into a corresponding salt and optionally purifying and/or isolating the salt, or reacting a compound corresponding to formula II

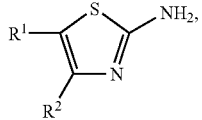
II in which $R^1$ and $R^2$ have the meanings indicated above, in a reaction medium, optionally in the presence of at least one organic or inorganic acid or at least one transition metal salt, with an isocyanide corresponding to formula III

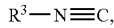
III in which $R^3$ has the meaning indicated above, and with an aldehyde of the general formula VI,

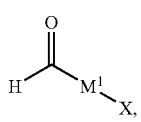
VI in which $M^1$ has the meaning indicated above and X denotes a leaving group, preferably a halogen residue or a sulfonic acid ester, particularly preferably chlorine, bromine or trifluoromethanesulfonate, to yield a compound corresponding to formula VIII,

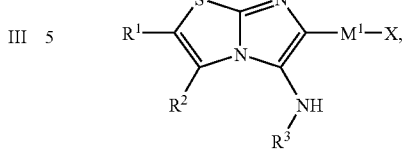
VII in which $R^1$, $R^2$, $R^3$, $M^1$ and X have the above-mentioned meanings, and optionally purifying and/or isolating the compound, and optionally transforming the compound into a corresponding salt and optionally purifying and/or isolating the salt;

and reacting the compound of formula VII or salt thereof with an acetylene compound corresponding to formula XI,

XI in which each R independently denotes a linear or branched alkyl residue or an unsubstituted phenyl residue, in a reaction medium, optionally in the presence of at least one suitable catalyst, optionally in the presence of at least one copper(I)salt, preferably in the presence of copper-(I)-iodide, and optionally in the presence of at least one inorganic and/or organic base to yield a correspondingly substituted compound corresponding to formula XII

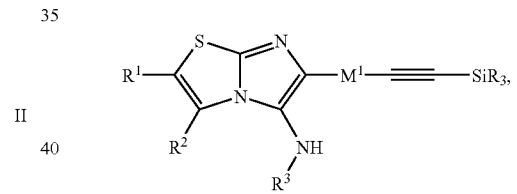
XII in which $R^1$, $R^2$, $R^3$ and $M^1$ have the above-mentioned meaning and each R independently denotes a linear or branched alkyl residue or an unsubstituted phenyl residue, and optionally purifying and/or isolating the compound, and optionally transforming the compound into a corresponding salt and optionally purifying and/or isolating the salt, and transforming a compound corresponding to formula XIII or salt thereof, in a reaction medium, optionally in the presence of at least one inorganic and/or organic base, optionally in the presence of at least one inorganic salt, and optionally in the presence of at least one ammonium salt, into a correspondingly substituted compound corresponding to formula XIII

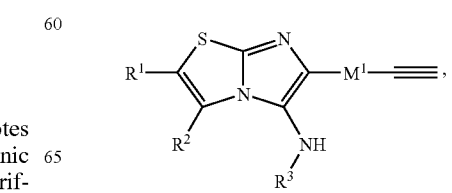
XIII in which $R^1$, $R^2$, $R^3$ and $M^1$ have the above-mentioned meanings, and optionally purifying and/or isolating the compound, and optionally transforming the compound into a corresponding salt and optionally purifying and/or isolating the salt; and reacting a compound corresponding to formula XIII and/or a compound corresponding to formula XII with a compound corresponding to the formula $$M^2-X$$

in which $M^2$ has the above-mentioned meaning and X denotes a leaving group, preferably a halogen residue or a sulfonic acid ester, particularly preferably chlorine, bromine or trifluoromethanesulfonate, in a reaction medium, optionally in the presence of at least one suitable catalyst, optionally in the presence of at least one inorganic and/or organic base, optionally in the presence of at least one inorganic salt and optionally in the presence of at least one ammonium salt into a correspondingly substituted compound corresponding to formula V

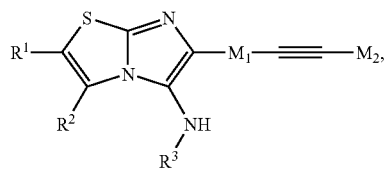

V in which $R^1$, $R^2$, $R^3$, $M^1$ and $M^2$ have the above-mentioned meanings, and optionally purifying and/or isolating the compound, and optionally transforming the compound into a corresponding salt and optionally purifying and/or isolating the salt, or reacting a compound corresponding to formula VII with an acetylene compound corresponding to formula VIII $$H\!\!-\!\!\!\equiv\!\!\!-\!\!M^2,$$
VIII in which $M^2$ has the meaning indicated above, in a reaction medium, optionally in the presence of a suitable catalyst, optionally in the presence of at least one copper(I) salt, preferably in the presence of copper-(I)-iodide and optionally in the presence of at least one inorganic and/or organic base, to yield a correspondingly substituted compound corresponding to formula V

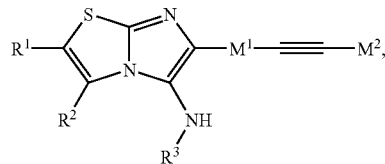

V in which $R^1$, $R^2$, $R^3$, $M^1$ and $M^2$ have the above-mentioned meanings, and optionally purifying and/or isolating the compound, and optionally transforming the compound into a corresponding salt and optionally purifying and/or isolating the salt, and optionally reacting the compound of formula V with a compound corresponding to the formula $$R^4-X$$

in which $R^4$ has the meaning indicated above and X denotes a leaving group, preferably a halogen residue or a sulfonic acid ester, particularly preferably chlorine, in a reaction medium, in the presence of at least one organic or inorganic base, preferably in the presence of at least one metal hydride salt, or with a compound corresponding to the formula $$R^{21}-C(=\!O)-OH$$

in which $R^{21}$ has the meaning indicated above, in a reaction medium, optionally in the presence of at least one organic or inorganic base and/or in the presence of at least one coupling agent, or with a compound corresponding to the formula $$R^{21}-C(=\!O)-X$$

in which $R^{21}$ has the meaning indicated above and X denotes a leaving group, preferably a halogen residue or a sulfonic acid ester, particularly preferably chlorine, bromine or trifluoromethanesulfonate, in a reaction medium, optionally in the presence of at least one organic or inorganic base, or with a compound corresponding to the formula $$R^{21}-C(=\!O)-H$$

in which $R^{21}$ has the meaning indicated above, in a reaction medium, optionally in the presence of at least one reducing agent, to yield a compound corresponding to formula I

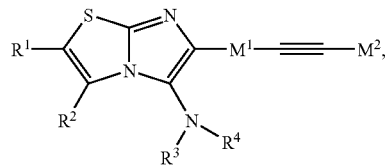

I in which $R^1$, $R^2$, $R^3$, $R^4$, $M^1$ and $M^2$ have the meanings indicated above, or a salt thereof, and optionally purifying and/or isolating the compound or salt thereof.

The present invention also relates to a method for producing a compound corresponding to the foregoing formula I comprising reacting a compound corresponding to formula V

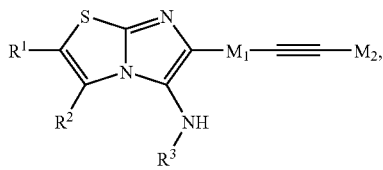

in which $R^1$, $R^2$, $R^3$, $M^1$ and $M^2$ have the above-mentioned meanings, optionally in a reaction medium in the presence of an organic or inorganic acid, to yield a compound corresponding to formula IX

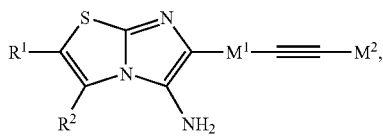

in which $R^1$, $R^2$, $M^1$ and $M^2$ have the above-mentioned meanings, and optionally purifying and/or isolating the compound, and optionally transforming the compound into a corresponding salt, and optionally purifying and/or isolating the salt, and reacting the compound or corresponding salt in a reaction medium, in the presence of an inorganic or organic base, preferably in the presence of at least one metal hydride salt, with a compound corresponding to the formula

in which $R^3$ has the meaning indicated above and X denotes a leaving group, preferably a halogen residue or a sulfonic acid ester, particularly preferably chlorine, or in a reaction medium, optionally in the presence of an organic or inorganic base and/or optionally in the presence of a coupling agent, with a compound corresponding to the formula

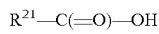

in which $R^{21}$ has the above-mentioned meaning, or in a reaction medium, optionally in the presence of an organic or inorganic base, with a compound corresponding to the formula

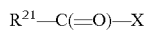

in which $R^{21}$ has the above-mentioned meaning and X denotes a leaving group, preferably a halogen residue or a sulfonic acid ester, particularly preferably chlorine, bromine or trifluoromethanesulfonate, or in a reaction medium, optionally in the presence of a reducing agent, with a compound corresponding to the formula

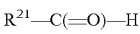

in which $R^{21}$ has the above-mentioned meaning, to yield a corresponding compound of formula X,

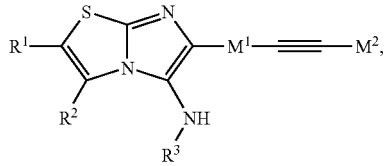

or salt thereof, in which $R^1$, $R^2$, $R^3$, $M^1$ and $M^2$ have the above-mentioned meanings, and optionally purifying and/or isolating the compound or salt thereof, and optionally reacting the compound of formula X with a compound corresponding to the formula

in which $R^4$ has the above-mentioned meaning and X denotes a leaving group, preferably a halogen residue or a sulfonic acid ester, particularly preferably chlorine, in a reaction medium, in the presence of at least one organic or inorganic base, preferably in the presence of at least one metal hydride salt, or with a compound corresponding to the formula

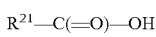

in which $R^{21}$ has the above-mentioned meaning, in a reaction medium, optionally in the presence of at least one organic or inorganic base and/or in the presence of at least one coupling agent, or with a compound corresponding to the formula

in which $R^{21}$ has the above-mentioned meaning and X denotes a leaving group, preferably a halogen residue or a sulfonic acid ester, particularly preferably chlorine, bromine or trifluoromethanesulfonate, in a reaction medium, optionally in the presence of at least one organic or inorganic base, or with a compound corresponding to the formula

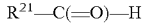

in which $R^{21}$ has the above-mentioned meaning, in a reaction medium, optionally in the presence of at least one reducing agent, to yield a compound corresponding to formula I

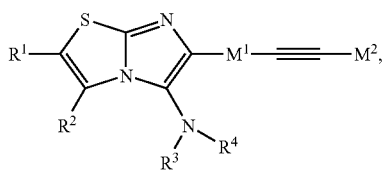

or salt thereof in which $R^1$, $R^2$, $R^3$, $R^4$, $M^1$ and $M^2$ have the above-mentioned meanings, and optionally purifying and/or isolating the compound or salt.

The methods according to the invention for producing substituted imidazo[2,1-b]thiazole compounds corresponding to the foregoing formula I are also illustrated in the following diagrams 1 through 4.

hydes of formula IV in a reaction medium, preferably selected from the group consisting of chloroform, dichloromethane, acetonitrile, methanol and ethanol, with the addition of at least one organic or inorganic acid, preferably trifluoroacetic acid or perchloric acid, or with the addition of at least one transition metal salt, preferably with the addition of at least one transition metal triflate (transition metal trifluoromethanesulfonate), particularly preferably with the addition of at least one transition metal triflate selected from the group consisting of scandium(III)trifluoromethanesulfonate, ytterbiumtrifluoromethanesulfonate and indium (III)trifluoromethanesulfonate, preferably at temperatures of 0° C. to 150° C., optionally in the presence of microwave radiation to yield a compound corresponding to formula the foregoing V.

A further method for producing substituted imidazo[2,1-b]thiazole compounds corresponding to the foregoing for-

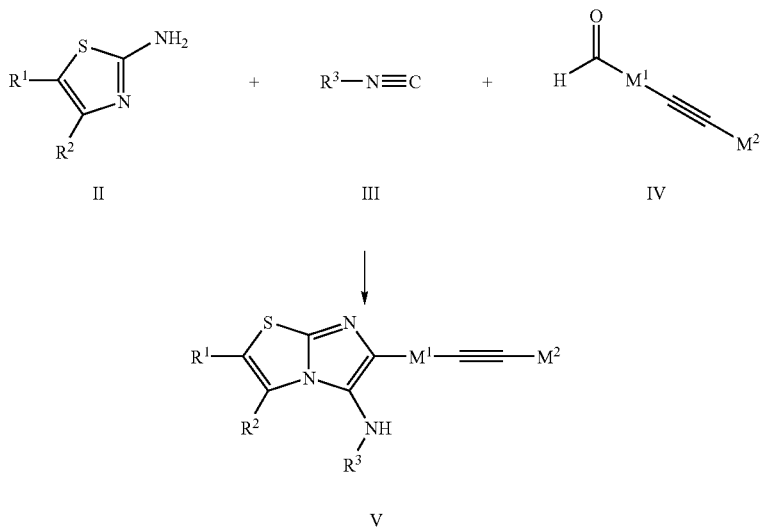

In a three-component-coupling reaction, amines of formula II are reacted with isocyanides of formula III and aldehydes of formula IV via compounds of the foregoing formula V is reproduced in Diagram 2.

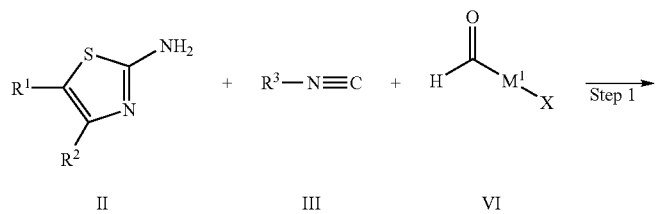

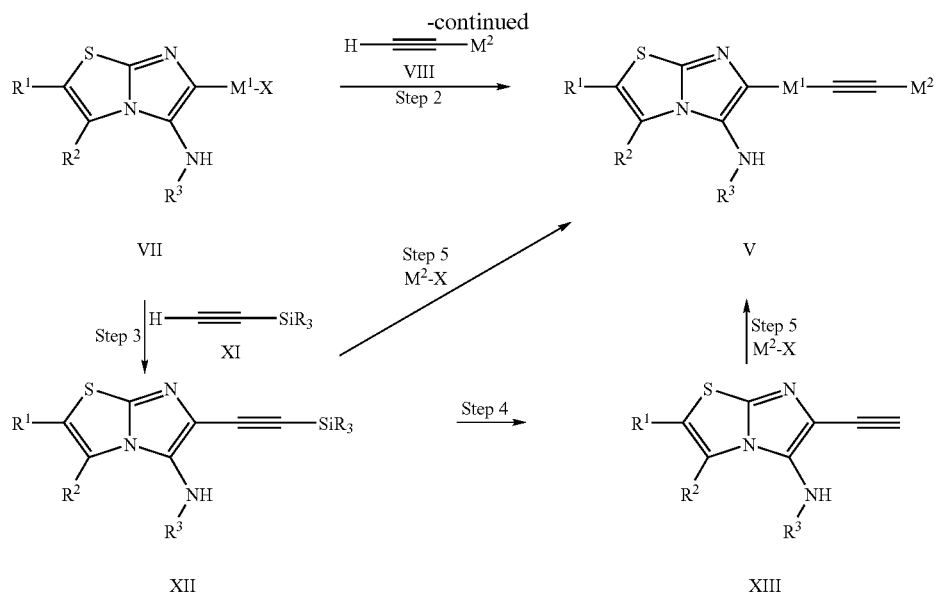

In step 1, amines of the general formula II are converted in a three-component-coupling reaction with isocyanides of the general formula III and aldehydes of the general formula VI, in which X denotes a leaving group, preferably a halogen residue or a sulfonic acid ester, particularly preferably chlorine, bromine or trifluoromethanesulfonate, in a reaction medium, preferably selected from the group consisting of chloroform, dichloromethane, acetonitrile, methanol and ethanol, with the addition of at least one organic or inorganic acid, preferably selected from the group consisting of trifluoroacetic acid or perchloric acid, or with the addition of at least one transition metal salt, preferably with the addition of at least one transition metal triflate (transition metal trifluoromethanesulfonate), particularly preferably with the addition of at least one transition metal trifluoromethanesulfonate selected from the group consisting of scandium(III)trifluoromethanesulfonate, ytterbiumtrifluoromethane-sulfonate and indium(III) trifluoromethanesulfonate, preferably at temperatures of 0° C. to 150° C., optionally in the presence of microwave radiation to yield a compound of formula VII, in which X denotes a leaving group, preferably a halogen residue or a sulfonic acid ester, particularly preferably chlorine, bromine or trifluoromethanesulfonate.

In step 2, compounds of the general formula VII indicated above, in which X denotes a halogen residue or a sulfonic acid ester, particularly preferably chlorine, bromine or trifluoromethanesulfonate, are converted with acetylenes of the general formula VIII in a reaction medium, preferably selected from the group consisting of methanol, ethyl acetate, ethanol, isopropanol, n-butanol, dioxane, chloroform, dichloromethane, pyridine, dimethylsulfoxide, toluene, tetrahydrofuran, dimethylformamide, acetonitrile, diethylether, water and corresponding mixtures, particularly preferably selected from the group consisting of dimethylformamide, ethyl acetate, tetrahydrofuran, water and corresponding mixtures, preferably with the addition of at least one palladium catalyst, preferably selected from the group consisting of palladium (II)-dichloride [PdCl$_2$], bis(triphenylphosphine)-palladium (II)-acetate [Pd(PPh$_3$)$_2$(OAc)$_2$], bis(triphenylphosphine)-palladium(II)-chloride [PdCl$_2$(PPh$_3$)$_2$], palladium(II)-acetate [Pd(OAc)$_2$; Ac=acetate], bis(acetonitrile)-palladium (II)-chloride [(CH$_3$CN)$_2$)PdCl$_2$], bis(benzonitrile)-palladium(II)-chloride [(PhCN)$_2$PdCl$_2$] and tetrakis (triphenylphosphine)palladium [(PPh$_3$)$_4$Pd], particularly preferably selected from the group consisting of Pd(PPh$_3$)$_2$ (OAc)$_2$, (PPh$_3$)$_4$Pd and PdCl$_2$(PPh$_3$)$_2$, optionally in the presence of at least one copper(I)salt, preferably in the presence of copper(I)-iodide, optionally in the presence of at least one phosphine, preferably a phosphine selected from the group consisting of triphenylphosphine, tri-(tert-butyl)-phosphine, triphenylarsine and tri-(ortho-toluoyl)-phosphine, particularly preferably in the presence of triphenylphosphine, optionally with the addition of at least one inorganic salt, preferably with the addition of lithium and/or zinc chloride, optionally with the addition of at least one organic base, preferably of an organic base selected from the group consisting of triethylamine, diisopropylamine, diisopropylethylamine and [1,4]-diazabicyclo-[2.2.2]octane and/or with the addition of at least one inorganic base, preferably selected from the group consisting of potassium carbonate, sodium hydrogen carbonate and caesium carbonate, whereby in particular the organic base can also be the reaction medium, at temperatures of preferably −70° C. to 300° C., particularly preferably of −70° C. to 150° C., optionally in the presence of microwave radiation to yield compounds of the general formula V.

In step 3, compounds of the general formula VII indicated above are converted with compounds of the general formula XI indicated above under the conditions cited in Diagram 2, Step 2 to yield compounds of the general formula XII.

In step 4, compounds of the general formula XII indicated above are converted in a reaction medium, preferably selected from the group consisting of methanol, ethyl acetate, ethanol, isopropanol, n-butanol, dioxane, chloroform, dichloromethane, pyridine, dimethylsulfoxide, toluene, tetrahydrofuran, dimethylformamide, acetonitrile, diethylether, water and corresponding mixtures, particularly preferably selected from the group consisting of dimethylformamide, ethyl acetate, tetrahydrofuran, water and corresponding mixtures, optionally in the presence of at least one inorganic base, preferably in the presence of at least one inorganic base selected from the group consisting of potassium carbonate, sodium hydroxide, potassium hydrogen carbonate, sodium hydrogen carbonate, potassium hydroxide and lithium hydroxide, optionally in the presence of at least one inorganic base, preferably of at least one inorganic base selected from the group consisting of triethylamine and pyridine, optionally in the presence of at least one inorganic salt, preferably in the presence of at least one ammonium salt or in the presence of potassium and/or sodium fluoride, particularly preferably in the presence of at least one ammonium salt selected from the group consisting of tetra-n-butylammonium fluoride, tetra-n-butyl-ammonium iodide and tetrabutylammonium bromide, at temperatures of preferably −70° C. to 300° C., particularly preferably of −70° C. to 150° C., optionally in the presence of microwave radiation to yield compounds of the general formula XII.

In step 5, compounds of the foregoing formulas XIII and XII are reacted with compounds corresponding to formula $M^2$-X, in which X denotes a halogen residue or a sulfonic acid ester, particularly preferably chlorine, bromine or trifluoromethanesulfonate, in a reaction medium, preferably selected from the group consisting of methanol, ethyl acetate, ethanol, isopropanol, n-butanol, dioxane, chloroform, dichloromethane, pyridine, dimethylsulfoxide, toluene, tetrahydrofuran, dimethylformamide, acetonitrile, diethylether, water and corresponding mixtures, particularly preferably selected from the group consisting of dimethylformamide, ethyl acetate, tetrahydrofuran, water and corresponding mixtures, preferably with the addition of at least one palladium catalyst, preferably selected from the group consisting of palladium (II)-dichloride [$PdCl_2$], bis(triphenylphosphine)-palladium (II)-acetate [$Pd(PPh_3)_2(OAc)_2$], bis(triphenylphosphine)-palladium(II)-chloride [$PdCl_2(PPh_3)_2$], palladium(II)-acetate [$Pd(OAc)_2$; Ac=acetate], bis(acetonitrile)-palladium (II)-chloride [$(CH_3CN)_2PdCl_2$], bis(benzonitrile)-palladium(II)-chloride [$(PhCN)_2PdCl_2$] and tetrakis (triphenylphosphine)palladium [$(PPh_3)_4Pd$], particularly preferably selected from the group consisting of $Pd(PPh_3)_2(OAc)_2$, $(PPh_3)_4Pd$ and $PdCl_2(PPh_3)_2$, optionally in the presence of at least one copper(I)salt, preferably in the presence of copper(I)-iodide, optionally in the presence of at least one phosphine, preferably a phosphine selected from the group consisting of triphenylphosphine, tri-(tert-butyl)-phosphine, triphenylarsine and tri-(ortho-toluoyl)-phosphine, particularly preferably in the presence of triphenylphosphine, optionally with the addition of at least one inorganic salt, preferably with the addition of lithium and/or zinc chloride, optionally in the presence of at least one ammonium salt or in the presence of potassium and/or sodium fluoride, preferably in the presence of at least one ammonium salt selected from the group consisting of tetra-n-butylammonium fluoride, tetra-n-butyl-ammonium iodide and tetrabutylammonium bromide, optionally with the addition of at least one organic base, preferably of an organic base selected from the group consisting of triethylamine, diisopropylamine, diisopropylethylamine and [1,4]-diazabicyclo-[2.2.2]octane and/or with the addition of at least one inorganic base, preferably selected from the group consisting of potassium carbonate, sodium hydrogen carbonate and caesium carbonate, whereby in particular the organic base can also be the reaction medium, at temperatures of preferably −70° C. to 300° C., particularly preferably of −70° C. to 150° C., optionally in the presence of microwave radiation to yield compounds of the general formula V.

The conversion of compounds of the general formula XII with compounds of the general formula $M^2$-X is preferably performed in the presence of at least one ammonium salt or in the presence of potassium and/or sodium fluoride.

The compounds of formula V can be converted as shown in Diagram 3 to yield compounds of formula X.

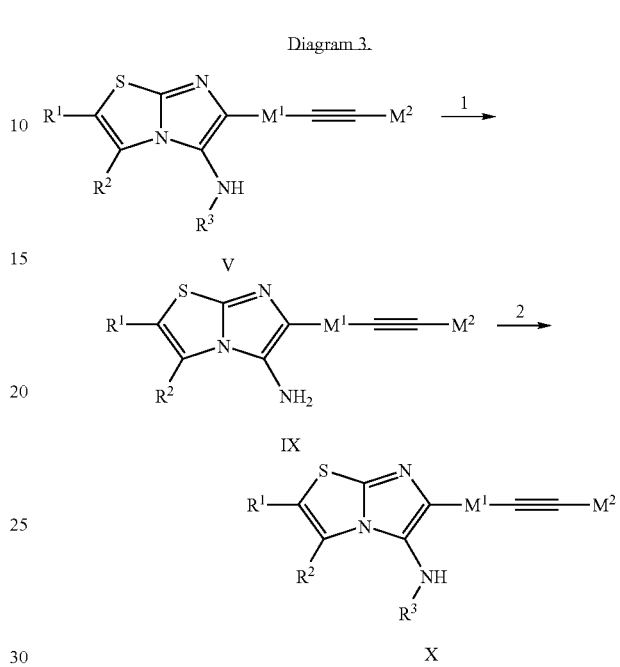

In step 1, compounds of the general formula V indicated above are converted in a reaction medium, preferably selected from the group consisting of ethanol, methanol and acetone, with the addition of at least one organic acid, preferably acetic acid or trifluoroacetic acid and/or with the addition of at least one inorganic acid, preferably hydrochloric acid or sulfuric acid, at temperatures of preferably 0° C. to 80° C., optionally in the presence of microwave radiation to yield compounds of the general formula IX.

In step 2, compounds of the general formula IX indicated above are converted with carboxylic acids of the general formula $R^{21}$—(C=O)—OH, in which $R^{21}$ has the above-mentioned meaning, in a reaction medium, preferably selected from the group consisting of diethylether, tetrahydrofuran, acetonitrile, methanol, ethanol, dimethylformamide and dichloromethane, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluroniom hexafluorophosphate (HBTU) and 1-hydroxy-7-azabenzotriazol (HOAt), optionally in the presence of at least one inorganic base, preferably selected from the group consisting of potassium carbonate and caesium carbonate, or of an organic base, preferably selected from the group consisting of triethylamine, pyridine, dimethylaminopyridine and diisopropylethylamine preferably at temperatures of −70° C. to 100° C., optionally in the presence of microwave radiation to yield compounds of the general formula X.

Alternatively, compounds of the general formula IX are converted with carboxylic acid derivatives or carbonic acid derivatives of the general formula $R^{21}$—(C=O)—X, whereby X denotes a halogen residue, preferably chlorine or bromine, in a reaction medium, preferably selected from the group consisting of diethylether, tetrahydrofuran, acetonitrile, methanol, ethanol, dimethylformamide and dichloromethane, with or without addition of at least one organic or inorganic base, for example, triethylamine, dimethylaminopyridine, pyridine or diisopropylamine, optionally in the presence of at least one organic base, preferably selected from the group consisting of triethylamine, dimethylaminopyridine, pyridine and diisopropylamine, or of an inorganic base at temperatures of preferably −70° C. to 10° C., optionally in the presence of microwave radiation to yield compounds of the general formula X.

As a further alternative, compounds of the general formula IX are converted with aldehydes of the general formula $R^{21}$—C(=O)—H in a reaction medium, preferably selected from the group consisting of diethylether, tetrahydrofuran, methanol, ethanol, dichloromethane and toluene, with the addition of at least one reducing agent, preferably selected from the group consisting of sodium borohydride, sodium acetoxyborohydride or sodium cyanoborohydride, at temperatures of preferably −70° C. to 100° C., optionally in the presence of microwave radiation to yield compounds of the general formula X.

Compounds of formula IX can also be converted with compounds of the formula $R^3$—X, in which X denotes a halogen residue, preferably chlorine, in a reaction medium, preferably selected from the group consisting of toluene, tetrahydrofuran and diethylether, with the addition of at least one metal hydride salt, preferably with the addition of at least one metal hydride salt selected from the group consisting of sodium hydride, potassium hydride and lithium hydride, at temperatures of preferably 0° C. to 40° C. to yield compounds of the general formula X.

Compounds of formulas X and V can furthermore be converted as indicated in Diagram 4 to yield compounds corresponding to formula I, whereby the same methods as described under Diagram 3, Step 2 can be used.

Diagram 4.

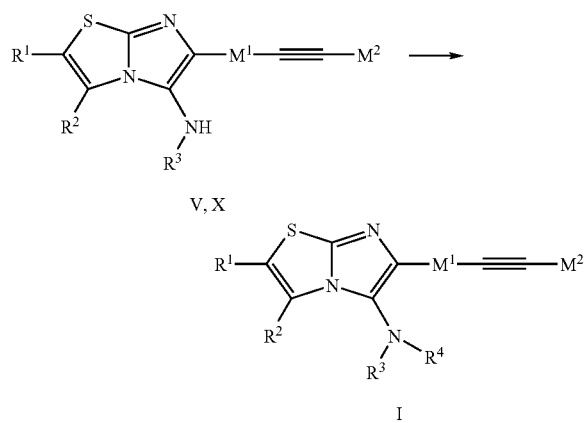

The compounds of the formulae II, III, IV, VI and VIII indicated above and of the general formulae $R^3$—X, $R^4$—X, $R^{21}$—C(=O)—OH, $R^{21}$—C(=O)—X and $R^{21}$—C(=O)—H indicated above are in each case available to purchase on the market and/or can be produced according to the normal methods known to the person skilled in the art.

The conversions described above can in each case be performed under normal conditions familiar to persons skilled in the art, for example, in terms of pressure or the sequence of the addition of components. The optimum performance of the method according to the respective conditions can optionally be determined by the person skilled in the art by simple preliminary tests.

The intermediate and end products obtained according to the conversions described above can in each case, if desired and/or necessary, be purified and/or isolated according to conventional methods known to the person skilled in the art. Suitable purification methods are, for example, extraction methods and chromatographic methods such as column chromatography or preparative chromatography.

All of the method steps described above and in each case also the purification and/or isolation of intermediate or end products can partially or entirely be performed under an inert gas atmosphere, preferably under a nitrogen atmosphere.

The substituted imidazo[2,1-b]thiazole compounds according to the invention corresponding to the foregoing formulas I, Ia, Ib, Ic, Id, Ie, If, Ig and Ih, referred to below only as compounds of the general formula I, and corresponding stereoisomers can be isolated both in the form of the free bases thereof, the free acids thereof as well as in the form of corresponding salts, in particular physiologically acceptable salts.

The free bases of the respective substituted imidazo[2,1-b]thiazole compounds according to the invention corresponding to the foregoing formula I and corresponding stereoisomers can, for example, be transformed into corresponding salts, preferably physiologically acceptable salts, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aparaginic acid.

The free bases of the respective substituted imidazo[2,1-b]thiazole compounds corresponding to the foregoing formula I and corresponding stereoisomers can likewise be transformed with the free acid or a salt of a sugar substitute such as e.g. saccharin, cyclamate or acesulfam into the corresponding physiologically acceptable salts.

The free acids of the substituted imidazo[2,1-b]thiazole compounds corresponding to the foregoing formula I and corresponding stereoisomers can correspondingly be transformed into corresponding physiologically acceptable salts by reaction with a suitable base. Examples of such salts include the alkali metal salts, alkaline earth metal salts or ammonium salts $[NH_xR_{4-x}]^+$, in which x=0, 1, 2, 3 or 4 and R denotes a linear or branched $C_{1-4}$-alkyl residue.

The substituted imidazo[2,1-b]thiazole compounds according to the invention corresponding to the foregoing formula I and corresponding stereoisomers, as well as the corresponding acids, bases or salts thereof, can optionally also be obtained according to standard methods known to persons skilled in the art in the form of solvates thereof, preferably in the form of hydrates.

Insofar as the substituted imidazo[2,1-b]thiazole compounds according to the invention corresponding to the foregoing formula I are obtained after their production in the form of a mixture of stereoisomers, for example in the form of a racemate or other mixture of various enantiomers and/or diastereomers thereof, these mixtures can be separated and optionally isolated using conventional techniques known to persons skilled in the art. Examples of such techniques include chromatographic separating methods, in particular liquid chromatography methods under normal pressure or under elevated pressure, preferably MPLC and HPLC methods, and fractional crystallization methods. In this way, in particular, individual enantiomers, e.g. diastereomeric salts formed by HPLC on the chiral stationary phase or by crystallization with chiral acids such as (+) tartaric acid, (−) tartaric acid or (+) 10-camphor sulfonic acid, can be separated from one another and isolated.

The substituted imidazo[2,1-b]thiazole compounds according to the invention corresponding to the foregoing formula I and corresponding stereoisomers and their respective corresponding acids, bases, salts and solvates are toxicologically safe and are therefore suitable for use as active pharmaceutical ingredients in pharmaceuticals. The invention therefore also relates to a pharmaceutical formulation containing at least one imidazo[2,1-b]thiazole compound according to the invention corresponding to the foregoing formula I, in each case optionally in the form of an isolated stereoisomer thereof, in particular an enantiomer or diastereomer, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The active compounds and pharmaceutical compositions according to the invention are useful for mGluR5 receptor regulation, in particular for inhibition of the mGluR5 receptor. Thus, the active compounds and pharmaceutical compositions according to the invention are useful for treating and/or inhibiting disorders and/or illnesses which are at least partially mediated by mGluR5 receptors.

The active compounds and pharmaceutical compositions according to the invention are therefore particularly suitable for the treatment and/or inhibition of pain, especially pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably Attention Deficit Disorder (ADD); psychiatric disorders, preferably selected from the group consisting of anxiety states and panic attacks; epilepsy; coughing; urinary incontinence; diarrhea; pruritus; schizophrenia; cerebral ischaemia; muscle spasms; cramps; lung illnesses, preferably selected from the group consisting of asthma and pseudocroup; regurgitation (vomiting); stroke; dyskinesia; retinopathy; listlessness; drowsiness; weariness; laryngitis; disorders of food intake, preferably selected from the group consisting of bulimia, cachexia, anorexia and obesity; dependency on alcohol; dependency on medicines; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications, preferably to natural or synthetic opioids; stomach-esophagus-reflux-syndrome; gastroesophagal reflux; irritable bowel syndrome; for diuresis; for antinatriuresis; for influencing the cardiovascular system; for increasing vigilance; for increasing libido; for modulating locomotor activity or for local anaesthesia.

The active compounds and pharmaceutical formulations according to the invention are particularly suitable for the treatment and/or inhibition of pain, especially pain selected from the group consisting of acute pain, chronic pain, neuropathic pain and visceral pain; psychiatric disorders, preferably selected from the group consisting of anxiety states and panic attacks; dependency on alcohol; dependency on medicines; disorders of food intake, preferably selected from the group consisting of bulimia, cachexia, anorexia and obesity; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications and/or drugs, in particular to natural or synthetic opioids; stomach-esophagus-reflux-syndrome; gastroesophagal reflux and irritable bowel syndrome.

The active compounds and pharmaceutical compositions according to the invention are even more preferably suitable for the treatment and/or inhibition of pain, especially pain selected from the group consisting of acute pain, chronic pain, neuropathic pain and visceral pain.

The active compounds and pharmaceutical compositions according to the invention are also even more preferably suitable for the treatment and/or inhibition of psychiatric disorders, preferably selected from the group consisting of anxiety states and panic attacks.

The active compounds and pharmaceutical compositions according to the invention are most preferably suitable for the treatment and/or inhibition of pain, especially of acute pain, chronic pain, neuropathic pain or visceral pain.

The invention further relates to the use of at least one substituted imidazo[2,1-b]thiazole compound according to the invention corresponding to the foregoing formula I, optionally in the form of an isolated stereoisomer thereof, in particular an enantiomer or diastereomer, the racemates thereof or in the form of a mixture of stereoisomers, in particular the enantiomers and/or diastereomers, in any desired mixing ratio, or in the form of a corresponding salt or solvate, and optionally one or more pharmaceutically acceptable auxiliary substances for the production of a pharmaceutical composition for mGluR5 receptor regulation, particularly for inhibition of the mGluR5 receptor.

It is particularly advantageous to use the substituted imidazo[2,1-b]thiazole compound according to the invention corresponding to the foregoing formula I, optionally in the form of an isolated stereoisomer, in particular enantiomer or diastereomer, the racemates thereof or in the form of a mixture of stereoisomers, in particular the enantiomers and/or diastereomers, in any desired mixing ratio, or in the form of a corresponding salt or solvate, and optionally one or more pharmaceutically acceptable auxiliary substances, to produce a pharmaceutical composition for the treatment and/or inhibition of disorders and/or illnesses which are at least partially mediated by mGluR5 receptors.

The use of at least one substituted imidazo[2,1-b]thiazole compound according to the invention corresponding to the foregoing formula I is particularly preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a drug for the prevention and/or treatment of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably Attention Deficit Disorder (ADD); psychiatric disorders, preferably selected from the group consisting of anxiety states and panic attacks; epilepsy; coughing; urinary incontinence; diarrhea; pruritus; schizophrenia; cerebral ischaemia; muscle spasms; cramps; lung illnesses, preferably selected from the group consisting of asthma and pseudo-croup; regurgitation (vomiting); stroke; dyskinesia; retinopathy; listlessness; drowsiness; weariness; laryngitis; disorders of food intake, preferably selected from the group consisting of bulimia, cachexia, anorexia and obesity; dependency on alcohol; dependency on medicines; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications, preferably to natural or synthetic opioids; stomach-esophagus-reflux-syndrome; gastroesophagal reflux; irritable bowel syndrome; for diuresis; for antinatriuresis; for influencing the cardiovascular system; for increasing vigilance; for increasing libido; for modulating locomotor activity or for local anaesthesia.

It is very particularly preferred to use at least one substituted imidazo[2,1-b]thiazole compound according to the invention corresponding to the foregoing formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt or solvate, and optionally one or more pharmaceutically acceptable auxiliary substances for the production of a pharmaceutical composition for the treatment and/or inhibition of pain, preferably of pain selected from the group consisting of acute pain, chronic pain, neuropathic pain and visceral pain; psychiatric disorders, preferably selected from the group consisting of anxiety states and panic attacks; dependency on alcohol; dependency on medicines; disorders of food intake, preferably selected from the group consisting of bulimia, cachexia, anorexia and obesity; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications and/or drugs, particularly to natural or synthetic opioids; stomach-esophagus-reflux-syndrome; gastroesophagal reflux and irritable bowel syndrome.

It is even further preferred to use at least one substituted imidazo[2,1-b]thiazole compound according to the invention corresponding to the foregoing formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt or in each case in the form of a corresponding solvate, and optionally one or more pharmaceutically acceptable auxiliary substances for the production of a pharmaceutical composition for the treatment and/or inhibition of pain, preferably of pain selected from the group consisting of acute pain, chronic pain, neuropathic pain and visceral pain.

The use of at least one substituted imidazo[2,1-b]thiazole compound according to the invention of the general formula I indicated above is even further preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt or in each case in the form of a corresponding solvate, and optionally one or more pharmaceutically acceptable auxiliary substances for the production of a drug for the prevention and/or treatment of psychiatric disorders, preferably selected from the group consisting of anxiety states and panic attacks.

The pharmaceutical composition according to the invention is suitable for administration to adults and/or to children, including infants.

The pharmaceutical composition according to the invention may be formulated as a liquid, semisolid or solid dosage form, for example, in the form of solutions for injection, drops, succi, syrups, sprays, suspensions, tablets, patches, capsules, dressings, suppositories, ointments, creams, lotions, gels, emulsions, aerosols or in multiparticulate form, for example, in the form of pellets or granules, optionally pressed into tablets, packaged in capsules or suspended in a liquid, and may also be administered as such.

In addition to at least one substituted imidazo[2,1-b]thiazole compound according to the invention of the general formula I indicated above, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the pharmaceutical composition according to the invention conventionally contains further physiologically acceptable pharmaceutical auxiliary substances, which can preferably be selected from the group consisting of matrix materials, fillers, solvents, diluents, surface-active substances, dyes, preservatives, disintegrants, slip agents, lubricants, aromas and binders. The selection of the physiologically acceptable auxiliary substances and the quantities thereof which are to be used depends upon whether the pharmaceutical composition is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. The substituted imidazo[2,1-b]thiazole compounds according to the invention used in the pharmaceutical composition according to the invention in a depot in dissolved form or in a dressing, optionally with the addition of skin penetration promoters, are suitable percutaneous administration preparations. Orally or percutaneously administrable formulations may also release the respective substituted imidazo[2,1-b]thiazole compound according to the invention in a delayed manner.

Pharmaceutical compositions according to the invention can be produced using conventional means, devices, methods and processes known from the prior art, such as are described for example in "Remington's Pharmaceutical Sciences", ed. A. R. Gennaro, 17th ed., Mack Publishing Company, Easton, Pa. (1985), in particular in part 8, chapters 76 to 93.

The quantity of the respective substituted imidazo[2,1-b]thiazole compounds according to the invention corresponding to the foregoing formula I to be administered to the patient may vary and depends, for example, on the weight or age of the patient and on the mode of administration, the indication and the severity of the complaint. Conventionally, 0.005 to 2000 mg/kg, preferably 0.05 to 500 mg/kg, particularly preferably 0.05 to 100 mg/kg of patient body weight of at least one such compound according to the invention are administered per day.

Pharmacological Methods

1. Method for Determining the Affinity to the mGluR5 Receptor

Pig brain homogenate is produced by homogenization (Polytron PT 3000, Kinematica AG, 10,000 rpm for 90 seconds) of pig brain halves without medulla, cerebellum and pons in buffer pH 8.0 (30 mM Hepes, Sigma, order no. H3375+1 tablet complete to 100 ml, Roche Diagnostics, order no. 1836145) in ratio 1:20 (brain weight/volume) and differential centrifugation at 900×g and 40,000×g. In each case, 450 µg protein from brain homogenate is incubated with 5 nM $^3$-[H]-MPEP (Tocris, order no. R1212) (MPEP=2-methyl-6-(3-methoxyphenyl)-ethynylpyridine) in 250 µl incubation batches in 96 well microtitration plates and the compounds to be tested (10 µM in the test) in buffer (as above) at room temperature for 60 min.

Thereafter, the batches are filtered with the help of a Brandel Cell Harvester (Brandel, TYP Robotic 9600) on unifilter plates with glass fibre filter mats (Perkin Elmer, order no. 6005177) and subsequently washed with buffer (as above) 3 times with in each case 250 µl per sample. The filter plates are subsequently dried for 60 min at 55° C. 30 µL Ultima Gold™ scintillator is subsequently added per well (Packard BioScience, order no. 6013159) and the samples are measured after 3 hours on the β-counter (Mikrobeta, Perkin Elmer). The unspecific bond is determined by addition of 10 µM MPEP (Tocris, order no. 1212).

2a. Formalin Test in Rats

The formalin test (Dubuisson, D. and Dennis, S. G., 1977, Pain, 4, 161-174) represents a model for acute and chronic pain. A biphasic nociceptive reaction, which is recorded by observation of three clearly differentiable behavioural patterns, is induced by a single formalin injection into the dorsal side of a rear paw in freely mobile test animals. The reaction has two phases: Phase 1=Immediate reaction (duration up to 10 min; paw shaking, licking), Phase 2=Late reaction (after a rest phase; likewise, paw shaking, licking; duration up to 60 min). The 1st phase reflects a direct stimulation of the peripheral nocisensors with high spinal nociceptive input or glutamate release (acute pain phase); the 2nd phase reflects a spinal and peripheral hypersensitisation (chronic pain phase). In the investigations presented here, the chronic pain component (phase 2) was evaluated.

Formalin with a volume of 50 µl and a concentration of 5% is administered subcutaneously into the dorsal side of the right rear paw of each animal. The substances to be tested are administered 30 min before the formalin injection orally (p.o), intravenously (i.v.) or intraperitoneally (i.p.). The specific changes in behavior such as lifting and shaking the paw, shifts in weight of the animal as well as biting and licking reactions are observed and registered in the period of observation from 21 to 27 min after formalin injection. The various forms of behavior are summarized in the so-called pain rate (PR), which, relative to the sub-intervals of 3 min, represents the calculation of an average nociception reaction. The calculation of PR is performed on the basis of a numerical weighting (=in each case factor 1, 2, 3) of the observed forms of behaviour (corresponding behavioural score 1, 2, 3) and is calculated with the following formula:

$$PR=[(T_0 \times 0)+(T_1 \times 1)+(T_2 \times 2)+(T_3 \times 3)]/180$$

whereby $T_0$, $T_1$, $T_2$, and $T_3$ each correspond to the time in seconds in which the animal demonstrates modes of behavior 0, 1, 2 or 3. The group size is 10 animals (n=10).

2b. Formalin Test in Mice

Formalin with a volume of 20 µl and a concentration of 1% is administered subcutaneously into the dorsal side of the right rear paw of each animal. The substances to be tested are administered 15 min before the formalin injection intraperitoneally (i.p.). The specific changes in behaviour such as lifting and shaking the paw (score 3, Dubuisson & Dennis, 1977) are observed and registered in the period of observation from 21 to 24 min after formalin injection. The group size is 10 animals (n=10).

3. Neuropathic Pain in Rats

Effectiveness against neuropathic pain was investigated using the Bennett model (chronic constriction injury; Bennett and Xie, 1988, Pain 33: 87-107).

Sprague-Dawley rats having a weight of 140-160 g are provided with four loose ligatures of the right nervus ischiaticus under nembutal narcosis. At the paw innervated by the damaged nerve the animals develop an oversensitivity which is quantified after a recuperation phase of a week over approximately four weeks by means of a 4° C. cold metal plate (cold allodynia). The animals are observed for a period of 2 min. on this plate and the number of retraction reactions of the damaged paw is measured. Relative to the previous value before substance administration, the substance effect is determined over a period of an hour at four points in time (15, 30, 45, 60 min. after administration) and the resultant area under the curve (AUC) and the inhibition of the cold allodynia are expressed at the individual measurement points in percent of effect to vehicle control (AUC) or to the initial value (individual measurement points). The group size is n=10. The significance of an anti-allodynic effect is determined using the AUC values via a paired T-test (*$0.05 \geq p > 0.01$; $0.01 \geq p > 0.001$; *$p \leq 0.001$; Armitage and Berry, 1987, Stat. Methods in Medical Research, London: Blackwell Scientific Publications).

4. "Elevated Plus Maze" Model

In the "elevated plus maze" (EPM) model, compounds are tested for possible anxiolytic effects. The tests are performed in male Sprague-Dawley rats (200-250 g) and 2 "elevated plus mazes" (Med Associates) with electronically controlled infrared light boxes are used to determine the location of the animals in the labyrinth. Each labyrinth has 2 open and 2 closed arms and a central platform. The edges of the open arms are delimited by narrow strips. The entire labyrinth is mounted on a metal stand.

At the start of a 5-min test, each animal is individually placed on the central platform with its head in the direction of a closed arm. The following parameters are determined or calculated and evaluated:

number and percentage of entries into the open and closed arms, and percentage of time in the open and closed arms and on the central platform.

The data is analyzed by means of a 1-factorial ANOVA (comparison of treatment groups versus vehicle group). The significance level is set at p<0.05. All the groups have a size of N=10. The test is also described in Hogg, S. (1996) "A review of the validity and variability of the elevated plus-maze as an animal model of anxiety," *Pharmacol. Biochem. Behav.* 54, 21-30, and in Rodgers, R. J., Cole, J. C. (1994) "The elevated plus-maze: pharmacology, methodology and ethology," in Cooper, S. J., Hendrie, C. A. (eds.) *Ethology and Psychopharmacology*. Wiley & Sons; pp. 9-44.

5. Description of the Functional $Ca^{2+}$ Influx Assay 20,000 CHO-hmGluR5 cells/well (Euroscreen, Gosselies, Belgium) are pipetted into 96 well plates (BD Biosciences, Heidelberg, Germany, Ref 356640, clear bottom, 96 well, Poly-D-Lysine) and incubated overnight in HBSS buffer (Gibco No. 14025-050) with the following additions: 10% FCS (GIBCO, 10270-106) and doxycycline (BD Biosciences Clontech 631311 600 ng/ml). For the functional investigation, the cells were loaded with 2 µM fluo-4 and 0.01 Vol % Pluronic F127 (Molecular Probes Europe BV, Leiden Netherlands) in HBSS buffer (Hank's buffered saline solution, Gibco Invitrogen GmbH, Karlsruhe, Germany) with probenicide (Sigma P8761, 0.69 mg/ml) for 30 min at 37° C. The cells are then washed 3 times with washing buffer (HBSS buffer, Gibco No. 14025-050, with probenicide (Sigma P8761, 0.69 mg/ml) and subsequently absorbed with the same buffer ad 100 µl. After 15 min., the plates are transferred into a Fluorometric Imaging Plate Reader (FLIPR, Molecular Devices, Sunnyvale, Calif.) for the determination of $Ca^{2+}$ measurements in the presence of DHPG ((S)-3,5-dihydroxyphenylglycine, Tocris Biotrend Chemikalien GmbH, Cologne, Germany, final DHPG concentration: 10 µM) and in the presence or absence of test substances.

After recording the fluorescence base line for 10 sec., 50 µl test substance solution (various test substance concentrations in HBSS buffer with 1% DMSO and 0.02% Tween 20, Sigma) is added and the fluorescence signal is measured for 6 min. 50 µl DHPG solution ((S)-3,5-dihydroxyphenylglycine, Tocris Biotrend Chemikalien GmbH, Cologne, Germany, final DHPG concentration: 10 µM) is subsequently added and the inflow of $Ca^{2+}$ is simultaneously measured for 60 sec. The final DMSO concentration is 0.25% and the final Tween 20 content is 0.005%. The data is analysed with Microsoft Excel and GraphPad Prism. The dose-effect curves are calculated with non-linear regression and $IC_{50}$ values determined. Each data point is determined 3 times and $IC_{50}$ values are averaged from a minimum of 2 independent measurements.

Ki values are calculated according to the following formula:

$$Ki=IC50/(1+AG_{Conc.}/EC50))$$

where $AG_{Conc.}=10$ µM, and EC50 corresponds to the DHPG concentration which is required for half the maximum inflow of $Ca^{2+}$.

General Instructions for Producing Example Substituted Imidazo[2,1-b]Thiazoles

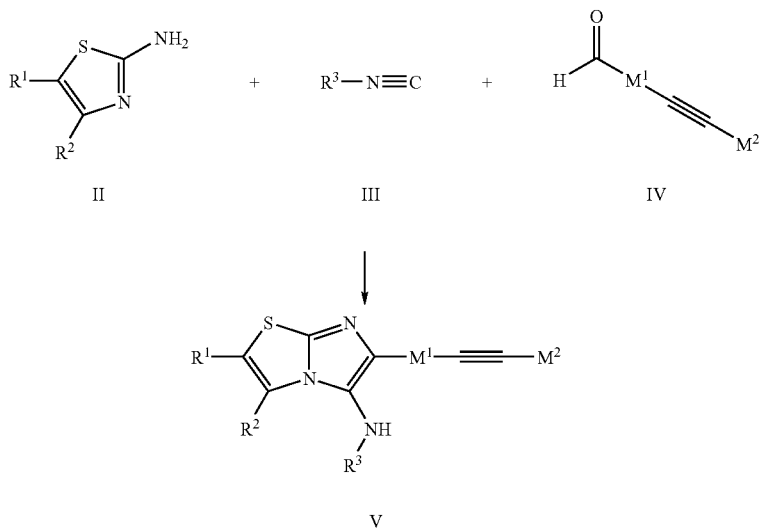

The reaction of amines of formula II with isocyanides of formula III and aldehydes of formula IV to yield compounds corresponding to formula V was carried out in organic solvents or solvent mixtures, for example, of chloroform, DCM, MeCN, MeOH or EtOH, with the addition of an organic or inorganic acid, for example, trifluoroacetic acid or perchloric acid, or with the addition of a transition metal triflate, for example, scandium(III) triflate, ytterbiumtriflate or indium (III)triflate, at temperatures of 0° C. to 150° C.

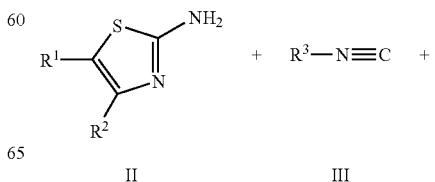

-continued

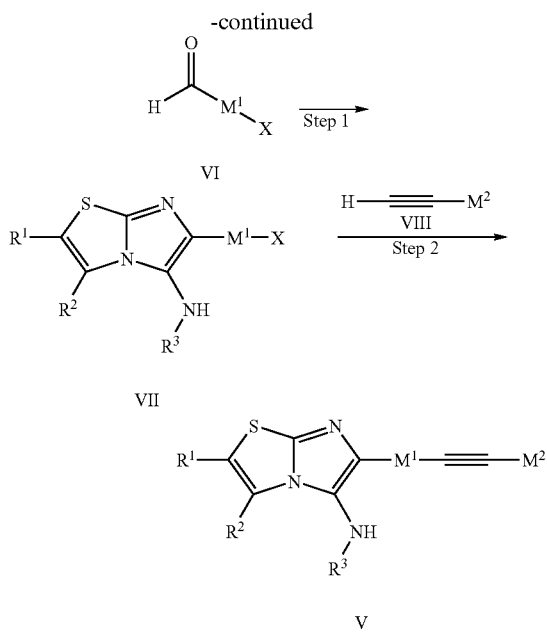

In step 1, the reaction of amines of formula II with isocyanides of formula III and aldehydes of formula VI, in which X denotes a halogen residue, to yield compounds of formula VII was carried out in organic solvents or solvent mixtures, for example, of chloroform, DCM, MeCN, MeOH or EtOH, with the addition of an organic or inorganic acid, for example, trifluoroacetic acid or perchloric acid, or with the addition of a transition metal triflate, for example, scandium(III)triflate, ytterbiumtriflate or indium(III)triflate, at temperatures of 0° C. to 150° C.

In step 2, the reaction of compounds of formula VII, in which X denotes a halogen residue, with acetylenes of formula VIII to yield compounds of formula V is carried out in a solvent or solvent mixture, for example, of toluene, THF, DMF, MeCN, ether, NEt$_3$ or diisopropylamine, with the addition of a palladium catalyst, for example, bis(triphenylphosphine)-palladium(II)-chloride, of copper(I)-iodide and an organic base, for example, NEt$_3$ or diisopropylamine, and/or inorganic base, for example, potassium carbonate or cesium carbonate, at temperatures of −70° C. to 150° C.

General synthesis diagram 3:

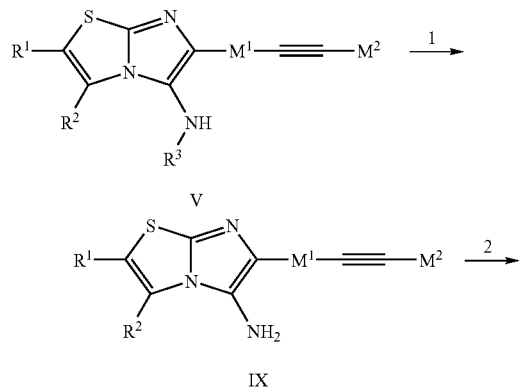

-continued

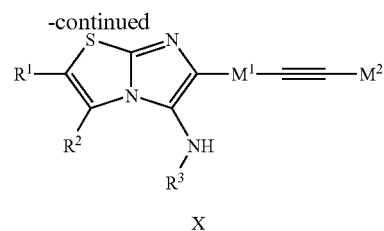

In step 1, compounds of formula V were reacted to yield amines of formula IX in a solvent or solvent mixture, for example, of EtOH, MeOH or acetone, with the addition of an organic or inorganic acid, for example, acetic acid, trifluoroacetic acis, hydrochloric acid or sulfuric acid, at temperatures of 0° C. to 80° C.

In step 2, compounds of formula IX (1 equivalent) were reacted with carboxylic acids (1 equivalent) of formula R$^{21}$—(C=O)—OH in a solvent or solvent mixture, for example, of ether, THF, MeCN, MeOH, EtOH, DMF or DCM, with or without the addition of a coupling reagent (1 equivalent), for example, DCC, BOP, HATU or EDCI and optionally in the presence of at least one inorganic or organic base, for example, NEt$_3$ or diisopropylethylamine, at temperatures of −70° C. to 100° C. to yield compounds of formula X.

Alternatively, compounds of formula IX (1 equivalent) were converted with carbonic acid halogenides (1 equivalent) or carbonic acid derivatives of formula R$^{21}$—(C=O)—X, wherein X denotes a halogen residue, in a solvent or solvent mixture, for example, ether, THF, MeCN, MeOH, EtOH, DMF or DCM, with or without the addition of an organic or inorganic base, for example, NEt$_3$, DMAP, pyridine or diisopropylamine, at temperatures of −70° C. to 100° C. to yield compounds of formula X.

As a further alternative, compounds of the general formula IX (1 equivalent) were converted with aldehydes (1 equivalent) of formula R$^{21}$—C(=O)—H in a solvent or solvent mixture, for example, of ether, THF, MeOH, EtOH, DCM or toluene, and subsequent addition of a reducing agent, for example, sodium borohydride, sodium acetoxyborohydride or sodium cyanoborohydride, at temperatures of −70° C. to 100° C. to yield compounds of the general formula X.

Compounds corresponding to formula IX (1 equivalent) were likewise converted with compounds of formula R$^4$—X (1.1 equivalents), in which X denotes a halogen residue, preferably chlorine, in a solvent or solvent mixture, for example, of toluene, THF, or ether, with the addition of a metal hydride salt (1.1 equivalents), preferably with the addition of sodium hydride, to yield compounds of the general formula X at temperatures of 0° C. to 40° C.

General synthesis diagram 4:

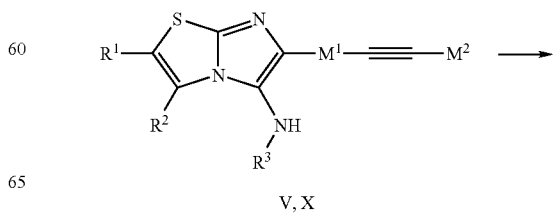

-continued

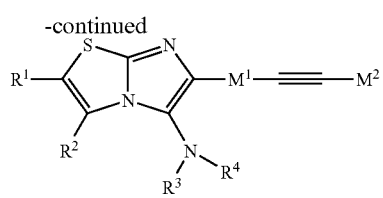

I

The compounds of formula V or X can be converted with the same methods as described in general synthesis diagram 3, step 2 to yield compounds of formula I.

General synthesis diagram 5:

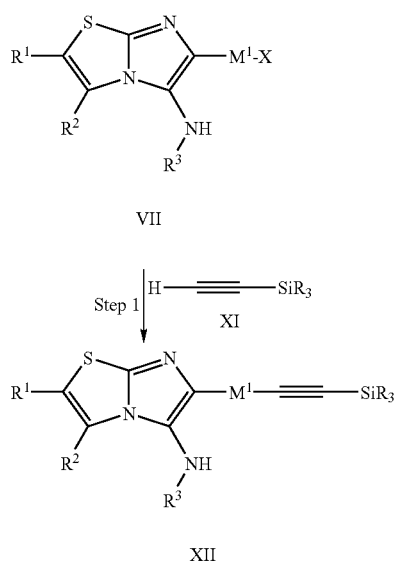

VII

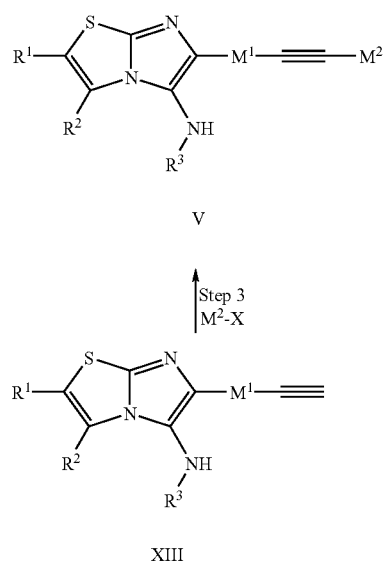

V

XII

XIII

In step 1, compounds of the general formula VII indicated above (1.0 equivalent), in which X denotes a halogen residue or a sulfonic acid ester, particularly preferably chlorine, bromine or trifluoromethanesulfonate, are converted with acetylenes of the general formula VIII (5.0 equivalents) in acetonitrile with the addition of tetrakis(triphenylphosphine) palladium [(PPh$_3$)$_4$Pd] (10 mol.-%) and with the addition of [1,4]-diazabicyclo-[2.2.2]octane (2.0 equivalents) under reflux to yield compounds of the general formula V.

In step 2, compounds of the general formula XII indicated above (1.0 equivalent) are converted in a reaction medium, preferably selected from the group consisting of methanol and dichloromethane and corresponding mixtures in the presence of potassium carbonate (10 mol-%) at temperatures of 20° C. to 30° C. to yield compounds of the general formula XIII.

In step 3, compounds of the general formula XIII indicated above (1.0 equivalent) are converted with compounds of the general formula M$^2$-X (1.25 equivalents), in which X denotes a halogen residue or a sulfonic acid ester, particularly preferably chlorine, bromine or trifluoromethanesulfonate, in ethylacetate, with the addition of bis(triphenylphosphine)-palladium(II)-chloride [PdCl$_2$(PPh$_3$)$_2$] (5 mol-%), in the presence of copper(I)-iodide (6 mol-%), with the addition of triethylamine (2.0 equivalents), at temperatures of 40° C. to 60° C., to yield compounds of the general formula V.

The instructions set forth above for producing substituted imidazo[2,1-b]thiazoles according to the present invention are illustrated in further detail below with reference to example compounds. The following examples are intended to illustrate the invention in greater detail but do not restrict the general concept of the invention.

EXAMPLES

Yields of the produced compounds are not optimized, and all temperatures are uncorrected.

Abbreviations:

| | |
|---|---|
| aq. | aqueous |
| d | days |
| Brine | saturated, aqueous NaCl solution |
| DCM | dichloromethane |
| DMF | N,N-dimethylformamide |
| AE | acetic acid ethylester |
| Ether | diethylether |
| sat. | saturated |
| NEt$_3$ | triethylamine |
| RT | room temperature |
| CC | column chromatography |
| TBME | tertiary butyl-methyl-ether |

The chemicals and solvents used were commercially acquired from the normal suppliers (Acros, Avocado, Aldrich, Bachem, Fluka, Lancaster, Maybridge, Merck, Sigma, TCI, etc.) or synthesized according to methods known to persons skilled in the art. Silica gel 60 (0.040-0.063 mm) from E. Merck, Darmstadt was used as the stationary phase for the column chromathography. The thin layer chromatographic tests were carried out with HPTLC ready plates, silica gel 60 F 254, from E. Merck, Darmstadt. The mixture ratios of solvents, mobile solvents or for chromatographic investigations are always indicated in volume/volume. Analysis of all the examples was performed by mass spectroscopy and NMR spectroscopy.

Example 1

Synthesis of 6-(5-(phenylethynyl)thiophene-2-yl)-N-(2,4,4-trimethylpentane-2-yl)imidazo[2,1-b]thiazole-5-amine A solution of 400 mg (4.0 mmol) 2-aminothiazole, 1018 mg (4.8 mmol) 5-phenylethynyl-thiophene-2-carbaldehyde, 557 mg (4.0 mmol) (2,4,4-trimethylpentane-2-yl)-isocyanide and 400 µl of a 20% aq. perchloric acid was stirred in DCM (8 ml) for 5 d at RT. A 1 molar aq. $Na_2CO_3$ sol. was subsequently added. The phases were separated and the aqueous phase was extracted with DCM. The collected organic phases were washed with brine and dried over $MgSO_4$. After filtering and removal of the solvent in a vacuum, a CC (AE/hexane 1:4) was performed with the residue, whereby 637 mg (1.47 mmol, 37%) 6-(5-(phenylethynyl)thiophene-2-yl)-N-(2,4,4-trimethylpentane-2-yl)imidazo[2,1-b]thiazole-5-amine was obtained.

Example 2

Synthesis of N-tert-butyl-6-(5-(pyridine-2-ylethynyl)thiophene-2-yl)imidazo[2,1-b]thiazole-5-amine A solution of 400 mg (4.0 mmol) 2-aminothiazole, 938 mg (4.4 mmol) 5-(pyridine-2-yl-ethynyl)-thiophene-2-carbaldehyde, 332 mg (4.0 mmol) tert.butyl-isocyanide and 400 µl of a 20% aq. perchloric acid in chloroform (10 ml) was stirred for 10 d at RT. A 1 molar aq. $Na_2CO_3$ sol. was subsequently added. The phases were separated and the aqueous phase was extracted with chloroform. The collected organic phases were washed with brine and dried over $MgSO_4$. After filtering and removal of the solvent in a vacuum, a CC (AE/DCM 15:85) was performed with the residue, whereby 223 mg impure raw product was obtained. 156 mg (0.41 mmol, 10%) N-tert-butyl-6-(5-(pyridine-2-ylethinyl)thiophene-2-yl)imidazo[2,1-b]thiazole-5-amine was obtained from this by crystallisation from AE.

Example 3

Synthesis of N-tert-butyl-3-methyl-6-(5-(pyridine-2-ylethynyl)thiophene-2-yl)imidazo[2,1-b]thiazole-5-amine hydrochloride A solution of 256 mg (2.25 mmol) 2-amino-4-methyl-thiazole, 527 mg (2.48 mmol) 5-(pyridine-2-yl-ethinyl)-thiophene-2-carbaldehyde, 205 mg (2.48 mmol) tert.butyl-isocyanide and 58 µl of a 70% aq. perchloric acid was stirred in chloroform (2 ml) for 16 h at RT. Dilution with DCM (20 ml) was subsequently performed and a 1 molar aq. $Na_2CO_3$ sol. (10 ml) added. After 10 min stirring at RT, the phases were separated. The aqueous phase was extracted with DCM. The collected organic phases were dried over $MgSO_4$. After filtering and removal of the solvent in a vacuum, a CC (AE/DCM 25:75) was performed with the residue, whereby 41 mg impure raw product was obtained. This was dissolved in acetone (1 ml) and 1 µl water and 11 µl trimethylchlorosilane were subsequently added. The resultant precipitate was sucked up and washed with ether. Thereby, 18 mg (0.04 mmol, 2%) N-tert-butyl-3-methyl-6-(5-(pyridine-2-ylethynyl)thiophene-2-yl)imidazo[2,1-b]thiazole-5-amine hydrochloride was obtained.

Example 4

Synthesis of N-tert-butyl-2-methyl-6-(5-(pyridine-2-ylethynyl)thiophene-2-yl)imidazo[2,1-b]thiazole-5-amine A solution of 256 mg (2.25 mmol) 2-amino-5-methyl-thiazole, 527 mg (2.48 mmol) 5-(pyridine-2-yl-ethynyl)-thiophene-2-carbaldehyde, 205 mg (2.48 mmol) tert.butyl-isocyanide and 58 µl of a 70% n aq. perchloric acid was stirred in chloroform (2 ml) for 16 h at RT. Dilution with DCM (20 ml) was subsequently performed and a 1 molar aq. $Na_2CO_3$ sol. (10 ml) added. After 10 min stirring at RT, the phases were separated. The aqueous phase was extracted with DCM. The collected organic phases were dried over $MgSO_4$. After filtering and removal of the solvent in a vacuum, a CC (AE/DCM 25:75) was performed with the residue, whereby 367 mg impure raw product was obtained. 48 mg (0.12 mmol, 5%) N-tert-butyl-2-methyl-6-(5-(pyridine-2-ylethinyl)thiophene-2-yl)imidazo[2,1-b]thiazole-5-amine was obtained from this by crystallisation from AE.

Example 5

Synthesis of N-tert-butyl-2,3-dimethyl-6-(5-(pyridine-2-ylethinyl)thiophene-2-yl)-imidazo[2,1-b]thiazole-5-amine hydrochloride

Example 6

Synthesis von N-tert-butyl-2-chloro-6-(5-(pyridine-2-ylethinyl)thiophene-2-yl)-imidazo[2,1-b]thiazole-5-amine hydrochloride The synthesis of Examples 5 and 6 was performed in accordance with the method described in Example 3.

Example 7

N-tert-butyl-6-(5-(pyridine-4-ylethynyl)thiophene-2-yl)imidazo[2,1-b]thiazole-5-amine

Example 8

5-(tert-butylamino)-6-(5-(pyridine-2-ylethinyl)thiophene-2-yl)-imidazo[2,1-b]thiazole-2-carbonic acid methylester hydrochloride The synthesis of Examples 7 and 8 was performed in accordance with the method described in Example 4.

Example 9

N-tert-butyl-6-(5-(pyridine-2-ylethynyl)thiazole-2-yl)imidazo[2,1-b]thiazole-5-amine a) Synthesis of 6-(5-bromothiazole-2-yl)-N-tert-butylimidazo[2,1-b]thiazole-5-amine 1 molar perchloric acid (10 µl) in ethanol (4 ml) was added to a solution of 100 mg (1.0 mmol) 2-amino-thiazole, 191 mg (1.0 mmol) 5-bromo-thiazole-2-carbaldehyde and 97 mg (1.17 mmol) tert.butylisonitrile and the mixture was heated for 5 min in the microwave (Biotage Initiator). The reaction solution was subsequently concentrated in a vacuum. A CC (TBME/hexane 1:1) was performed with the residue, whereby 71 mg (0.2 mmol, 20%) 6-(5-bromothiazole-2-yl)-N-tert-butylimidazo[2,1-b]thiazole-5-amine [MH+] 357.0 was obtained.

b) Synthesis of N-tert-butyl-6-(5-(pyridine-2-ylethynyl)thiazole-2-yl)imidazo[2,1-b]thiazole-5-amine A mixture of 235 mg (0.66 mmol) 6-(5-bromothiazole-2-yl)-N-tert-butylimidazo[2,1-b]thiazole-5-amine, 22 mg (0.033 mmol) bis(triphenylphosphine)-palladium-(II)-chloride, 12 mg (0.066 mmol) copper-(I)-iodide, 80 μl (0.79 mmol) 2-ethynylpyridine and 731 μl (5.28 mmol) NEt₃ in DMF (2 ml) was heated in the microwave (Biotage Initiator) for 10 min to 120° C. The reaction solution was diluted with water and extracted several times with AE. The collected organic phases were washed with brine and dried over MgSO₄. After filtering and removal of the solvent in a vacuum, a CC (1.TBME, 2.MeOH) was performed with the residue, whereby 43 mg (0.11 mmol, 17%) N-tert-butyl-6-(5-(pyridine-2-ylethynyl)thiazole-2-yl)imidazo[2,1-b]thiazole-5-amine was obtained.

Example 10

Synthesis of 6-(5-pyridine-2-ylethynyl)thiophene-2-yl)-N-(2,4,4-trimethylpentane-2-yl)imidazo[2,1-b]thiazole-5-amine A solution of 5.0 g (50.0 mmol) 2-amino-thiazole, 10.7 g (50.0 mmol) 5-(pyridine-2-yl-ethynyl)-thiophene-2-carbaldehyde, 7.0 g (50.0 mmol) (2,4,4-trimethylpentane-2-yl)-isocyanide and 1.0 ml of a 70% aq. perchloric acid in chloroform (25 ml) was heated to 50° C. while being stirred for 5 d. Dilution with DCM was subsequently performed and a 1 molar aq. Na₂CO₃ sol. was added. After 10 min of stirring at RT, the phases were separated. The aqueous phase was extracted with DCM. The collected organic phases were dried over Na₂SO₄, filtered and concentrated in a vacuum. 11.86 g (27.3 mmol, 55%) 6-(5-pyridine-2-ylethynyl)thiophene-2-yl)-N-(2,4,4-trimethylpentane-2-yl)imidazo[2,1-b]thiazole-5-amine was obtained by multiple crystallisation of the residue from AE.

Example 11

N-tert-butyl-2-methyl-6-(4-(pyridine-2-ylethynyl)phenyl)imidazo[2,1-b]thiazole-5-amine The synthesis of Example 11 was performed in accordance with the method described in Example 10.

Example 12

Synthesis of N-tert-butyl-6-(5-(pyridine-2-ylethynyl)furan-2-yl)imidazo[2,1-b]thiazole-5-amine A solution of 380 mg (3.8 mmol) 2-amino-thiazole, 749 mg (3.8 mmol) 5-(pyridine-2-yl-ethynyl)-furan-2-carbaldehyde, 378 mg (3.8 mmol) tert.butyl-isonitril and 73 μl of a 70% aq. perchloric acid in chloroform (2 ml) was heated to 45° C. while being stirred for 16 h. Dilution with DCM was subsequently performed and a 1 molar aq. Na₂CO₃ sol. was added. After 10 min of stirring at RT, the phases were separated. The aqueous phase was extracted with DCM. The collected organic phases were dried over Na₂SO₄, filtered and concentrated in a vacuum. 472 mg (1.3 mmol, 34%) N-tert-butyl-6-(5-(pyridine-2-ylethynyl)furan-2-yl)imidazo[2,1-b]thiazole-5-amine was obtained by CC (AE) with the residue.

Example 13

N-tert-butyl-3-methyl-6-(5-(phenylethynyl)thiophene-2-yl)imidazo[2,1-b]thiazole-5-amine The synthesis of Example 13 was performed in accordance with the method described in Example 12.

Example 14

Synthesis of 6-(5-(pyridine-2-ylethynyl)thiophene-2-yl)imidazo[2,1-b]thiazole-5-amine Trifluoroacetic acid (30 ml) was added to a solution of 2.5 g (5.75 mmol) 6-(5-pyridine-2-ylethynyl)thiophene-2-yl)-N-(2,4,4-trimethylpentane-2-yl)imidazo[2,1-b]thiazole-5-amine (Example 10) in DCM (30 ml) and the mixture was stirred for 25 min at RT. Basification (pH>12) was subsequently performed under cooling (ice bath) with a 12 molar aq. NaOH sol. The resultant residue was filtered off and dissolved in a mixture of AE (200 ml) and DCM (50 ml) and washed with water (15 ml) and dried over Na₂SO₄. After removal of the solvent in a vacuum, 773 mg (2.40 mmol, 42%) 6-(5-(pyridine-2-ylethynyl)thiophene-2-yl)imidazo[2,1-b]thiazole-5-amine was obtained.

Example 16

N-tert-butyl-6-(5-((3-fluoropyridine-2-yl)ethynyl)thiophene-2-yl)imidazo[2,1-b]thiazole-5-amine a) Synthesis of 6-(5-bromothiophene-2-yl)-N-tert-butylimidazo[2,1-b]thiazole-5-amine 22.9 g (119.9 mmol) 5-bromo-thiophene-2-carbaldehyde and 11.0 g (131.9 mmol) tert.-butyl-isonitrile were added to a solution of 12.0 g (119.9 mmol) 2-amino-thiazole in chloroform (60 ml). A 1 molar perchloric acid (2.3 ml) was added to the reaction solution and heated to 50° C. while being stirred for 5 d. After cooling to RT, dilution with DCM was performed and a 1 molar aq. Na₂CO₃ sol. added. After 10 min of stirring at RT, the phases were separated. The organic phase was dried over Na₂SO₄, filtered and concentrated in a vacuum. 6.6 g (18.5 mmol, 15%) 6-(5-bromothiophene-2-yl)-N-tert-butylimidazo[2,1-b]thiazole-5-amine ([MH+] 356.0) was obtained by crystallisation of the residue from AE.

b) Synthesis of N-tert-butyl-6-(5-((trimethylsilyl)ethynyl)thiophene-2-yl)imidazo[2.1-b]thiazole-5-amine 4.1 g (3.5 mmol) tetrakis(triphenyl)phosphine-palladium (0), 17.2 g (175.4 mmol) trimethyl-silylacetylene and 7.9 g (70.2 mmol) 1,4-diazabicyclo[2.2.2]octane were consecutively added to a suspension of 12.5 g (35.1 mmol) 6-(5-bromothiophene-2-yl)-N-tert-butylimidazo[2,1-b]thiazole-5-amine in acetonitrile (150 ml). The reaction solution was heated for 72 h under reflux and subsequently concentrated in a vacuum. 3.0 g (7.9 mmol, 23%) N-tert-butyl-6-(5-((trimethylsilyl)ethynyl)thiophene-2-yl)imidazo[2,1-b]thiazole-5-amine ([MH+] 374.1) was obtained by CC (DCM/AE 95:5).

c) Synthesis of N-tert-butyl-6-(5-ethynylthiophene-2-yl)imidazo[2,1-b]thiazole-5-amine A suspension of 3.0 g (7.9 mmol) N-tert-butyl-6-(5-((trimethylsilyl)-ethynyl)thiophene-2-yl)imidazo[2,1-b]thiazole-5-amine in a mixture of DCM (12 ml) and methanol (58 ml) was heated to 35° C. and 108 mg (0.79 mmol) potassium carbonate was added. After 100 min of stirring at RT, water and DCM were added. The phases were separated and the aqueous phase was extracted with DCM. The collected organic phases were washed with water, dried over $Na_2SO_4$, filtered and concentrated in a vacuum. The obtained 2.17 g (7.2 mmol, 91%) of raw product of N-tert-butyl-6-(5-ethynylthiophene-2-yl)imidazo[2,1-b]thiazole-5-amine ([MH+] 302.1) was converted in the next step without further purification.

d) Synthesis of N-tert-butyl-6-(5-((3-fluoropyridine-2-yl)ethynyl)thiophene-2-yl)imidazo[2,1-b]thiazole-5-amine A solution of 450 mg (1.49 mmol) N-tert-butyl-6-(5-ethynylthiophene-2-yl)imidazo[2,1-b]thiazole-5-amine, 333 mg (1.90 mmol) 3-fluoro-2-iodo-pyridine, 38 mg (0.06 mmol) bis(triphenylphosphine)-palladium-(II)-chloride, 19 mg (0.07 mmol) copper-(I)-iodide and 389 µl (2.80 mmol) $NEt_3$ in AE (21 ml) was heated to 50° C. while being stirred for 20 h. Concentration in a vacuum was subsequently performed and a CC (AE) carried out with the residue, whereby 456 mg (1.15 mmol, 77%) N-tert-butyl-6-(5-((3-fluoropyridine-2-yl)ethynyl)thiophene-2-yl)imidazo[2,1-b]thiazole-5-amine was obtained.

Example 15

N-tert-butyl-6-(5-(pyrimidine-2-ylethynyl)thiophene-2-yl)imidazo[2,1-b]thiazole-5-amine Example 17

N-tert-butyl-6-(5-((2-fluoropyridine-4-yl)ethynyl)thiophene-2-yl)imidazo[2,1-b]thiazole-5-amine Example 18

N-tert-butyl-6-(5-(thiophene-2-ylethynyl)thiophene-2-yl)imidazo[2,1-b]thiazole-5-amine Example 19

N-tert-butyl-6-(5-(thiazole-2-ylethynyl)thiophene-2-yl)imidazo[2,1-b]thiazole-5-amine Example 20

3-((5-(5-(tert-butylamino)imidazo[2,1-b]thiazole-6-yl)thiophene-2-yl)ethynyl)phenol Example 21

3-((5-(5-(tert-butylamino)imidazo[2,1-b]thiazole-6-yl)thiophene-2-yl)ethynyl)benzonitrile Example 23

N-tert-butyl-6-(5-((3-methylpyridine-2-yl)ethynyl)thiophene-2-yl)imidazo[2,1-b]thiazole-5-amine The synthesis of Examples 15, 17, 18, 19, 20, 21 and 23 was performed in accordance with the method described in Example 16.

Example 25

Synthesis of N-(6-(5-(pyridine-2-ylethynyl)thiophene-2-yl)imidazo[2,1-b]thiazole-5-yl)benzamide 59 µl (0.52 mmol) benzylchloride was dropped into a solution of 185 mg (0.57 mmol) 6-(5-(pyridine-2-ylethynyl)thiophene-2-yl)imidazo[2,1-b]thiazole-5-amine (Example 14) and 174 µl (1.26 mmol) $NEt_3$ in DCM (3 ml) under cooling (ice bath). After 16 h of stirring at RT, dilution with AE was performed. Washing was subsequently carried out consecutively with a saturated, aqueous sodium carbonate solution and with a saturated, aqueous sodium chloride solution. The organic phase was dried over $Na_2SO_4$, filtered and concentrated in a vacuum. A CC (AE) was performed with the residue, whereby 10 mg (0.02 mmol, 4%) N-(6-(5-(pyridine-2-ylethynyl)thiophene-2-yl)imidazo[2,1-b]thiazole-5-yl)benzamide was obtained.

Example 22

N-ethyl-6-(6-(phenylethynyl)pyridine-3-yl)imidazo[2,1-b]thiazole-5-amine

The synthesis of Example 22 was performed in accordance with the method described in Example 4.

Example 24

N-(6-(5-(pyridine-2-ylethynyl)thiophene-2-yl)imidazo[2,1-b]thiazole-5-yl)acetamide The synthesis of Example 24 was performed in accordance with the method described in Example 25.

Molecular weight values obtained by mass spectrometry are listed in the following table.

| Example | Mass [MH$^+$] |
| --- | --- |
| 1 | 434.2 |
| 2 | 379.1 |
| 3 | 393.1 |
| 4 | 393.1 |
| 5 | 407.1 |
| 6 | 413.1 |
| 7 | 379.1 |
| 8 | 437.1 |
| 9 | 380.1 |
| 10 | 435.2 |
| 11 | 387.2 |
| 12 | 363.1 |
| 13 | 392.1 |
| 14 | 323.0 |
| 15 | 380.1 |
| 16 | 397.1 |
| 17 | 397.1 |
| 18 | 384.1 |
| 19 | 385.1 |
| 20 | 394.1 |
| 21 | 403.1 |
| 22 | 345.1 |
| 23 | 393.1 |
| 24 | 365.0 |
| 25 | 427.1 |

Pharmacological Data:

1. The affinity of the substituted imidazo[2,1-b]thiazole compounds according to the invention of the general formula I to the mGluR5 receptor was determined as described above. The substituted imidazo[2,1-b]thiazole compounds according to the invention exhibit an outstanding affinity to the mGluR5 receptor. The pharmacological data for the substituted imidazo[2,1-b]thiazole compounds according to Examples 1 to 4 is reproduced in the following Table 1:

TABLE 1

| Ex. | $IC_{50}$ [$^3$H]-MPEP bond mGluR5 receptor (pig) [µM] | mGluR5 receptor (pig) (10 µM) inhibition (%) | $ED_{50}$ formalin test (rat) i.v. [mg/kg] |
|---|---|---|---|
| 1 | 2.1800 | | |
| 2 | 0.0063 | | 0.47 |
| 3 | 0.0120 | | |
| 4 | 0.0055 | | |
| 5 | 0.0170 | | |
| 6 | 0.0099 | | |
| 7 | 0.0030 | | |
| 8 | 0.1600 | | |
| 10 | 0.1000 | | |
| 11 | 0.0200 | | |
| 12 | 0.0870 | | |
| 13 | | 48 | |
| 14 | 0.1400 | | |
| 15 | 0.0100 | | |
| 16 | 0.0130 | | |
| 17 | 0.0180 | | |
| 18 | 0.0450 | | |
| 19 | 0.0240 | | |
| 20 | 0.1700 | | |
| 21 | 0.0260 | | |
| 22 | | 82 | |
| 23 | 0.2300 | | |

2. The substituted imidazo[2,1-b]thiazole compounds according to the invention also exhibit an outstanding effect in the formalin test on rats as is reproduced in the following table 2.

TABLE 2

| Ex. | $ED_{50}$ formalin test (rat) i.v. [mg/kg] | Formalin test (rat) p.o. Reduction in the nociceptive behavior over controls at 10 mg/kg [%] |
|---|---|---|
| 2 | 0.47 | 66 |
| 4 | | 62 |

3. The substituted imidazo[2,1-b]thiazole compounds according to the invention exhibit an outstanding affinity to the human mGluR5 receptor (Table 3).

TABLE 3

| Ex. | $K_i$ mGluR5 receptor (human) $Ca^{2+}$-influx [µM] |
|---|---|
| 4 | 0.00031 |
| 7 | 0.00026 |

The foregoing description and examples have been set forth merely to illustrate the invention and are not intended to be limiting. Since modifications of the described embodiments incorporating the sprit and substance of the invention may occur to persons skilled in the art, the invention should be construed broadly to include all variations within the scope of the appended claims and equivalents.

The invention claimed is:

1. A substituted imidazo[2,1-b]thiazole compound corresponding to formula I

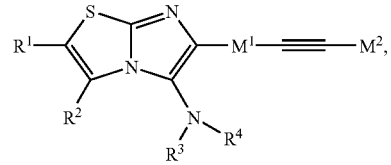

wherein

R$^1$ and R$^2$ each independently denote hydrogen; a halogen; —NO$_2$; —CN; —NH$_2$; —NHR$^5$; —NR$^6$R$^7$; —NH—C(=O)—R$^8$; —C(=O)—R$^9$, —C(=O)—NH$_2$; —C(=O)—NHR$^{10}$; —C(=O)—NR$^{11}$R$^{12}$; —C(=O)—OR$^{13}$; —(CH$_2$)$_m$—C(=O)—OR$^{14}$ with m=1, 2, 3, 4 or 5; —O—C(=O)—R$^{15}$; —(CH$_2$)$_n$—O—C(=O)—R$^{16}$ with n=1, 2, 3, 4 or 5; —OR$^{17}$; —(CH$_2$)$_o$—O—R$^{18}$ with o=1, 2, 3; 4 or 5; —SR$^{19}$; —(CH$_2$)$_p$—S(=O)$_t$—R$^{20}$ with p=1, 2, 3, 4 or 5 and t=0, 1 or 2; —NH—S(=O)$_2$—NR$^{27}$R$^{28}$; —S(=O)$_2$—NR$^{29}$R$^{30}$; —SF$_5$; —(CH$_2$)$_u$—O—S(=O)$_2$—R$^{31}$ with u=1, 2, 3, 4 or 5; —(CH$_2$)$_v$—O—S(=O)$_2$—O—R$^{32}$ with v=1, 2, 3, 4 or 5; —(CH$_2$)$_w$—O—P(=O)(OR$^{33}$)(OR$^{34}$) with w=1, 2, 3, 4 or 5; a linear or branched, saturated or unsaturated, unsubstituted or mono- or poly-substituted aliphatic group; a saturated or unsaturated, unsubstituted or mono- or poly-substituted cycloaliphatic group optionally having at least one heteroatom as a ring member, which cycloaliphatic group is bound via a linear or branched, unsubstituted or mono- or poly-substituted alkylene group and/or optionally may be condensed with an unsubstituted or mono- or poly-substituted mono- or polycyclic ring system; or an unsubstituted or mono- or poly-substituted aryl or heteroaryl group, which optionally may be bound via a linear or branched, unsubstituted or mono- or poly-substituted alkylene group and/or optionally may be condensed with an unsubstituted or mono- or poly-substituted mono- or polycyclic ring system;

R$^3$ and R$^4$ each independently denote hydrogen; —C(=O)—R$^{21}$; —(CH$_2$)$_q$—C(=O)—R$^{22}$ with q=1, 2, 3, 4 or 5; —C(=O)—O—R$^{23}$; —(CH$_2$)$_r$—C(=O)—O—R$^{24}$ with r=1, 2, 3, 4 or 5; —C(=O)—NHR$^{25}$; —(CH$_2$)$_s$—C(=O)—NHR$^{26}$ with s=1, 2, 3, 4 or 5; a linear or branched, saturated or unsaturated, unsubstituted or mono- or poly-substituted aliphatic group; a saturated or unsaturated, unsubstituted or mono- or poly-substituted cycloaliphatic group optionally having at least one heteroatom as a ring member, which cycloaliphatic group optionally may be bound via a linear or branched, unsubstituted or mono- or poly-substituted alkylene group and/or optionally may be condensed with an unsubstituted or mono- or poly-substituted mono- or polycyclic ring system; or an unsubstituted or mono- or poly-substituted aryl or heteroaryl group, which optionally may be bound via a linear or branched, unsubstituted or mono- or poly-substituted alkylene group and/or optionally may be condensed with an unsubstituted or mono- or poly-substituted mono- or polycyclic ring system, or R$^3$ and R$^4$ together with the nitrogen atom to which they are bound form a saturated or unsaturated, unsubstituted or mono- or poly-substituted heterocycloaliphatic group optionally having at least one further heteroatom as a ring member, which heterocycloaliphatic group optionally may be condensed with an unsubstituted or mono- or poly-substituted mono- or polycyclic ring system;

$R^5$, $R^6$, $R^7$, $R^8$, $R^{10}$, $R^{11}$, $R^{12}$, $R^{15}$ and $R^{16}$ each independently denote a linear or branched, saturated or unsaturated, unsubstituted or mono- or poly-substituted aliphatic group or an unsubstituted or mono- or poly-substituted aryl or heteroaryl group, which optionally may be bound via a linear or branched, unsubstituted or mono- or poly-substituted alkylene group and/or optionally may be condensed with an unsubstituted or mono- or poly-substituted mono- or polycyclic ring system;

$R^9$, $R^{13}$, $R^{14}$, $R^{17}$, $R^{13}$, $R^{19}$, $R^{20}$, $R^{21}$, $R^{22}$, $R^{23}$, $R^{24}$, $R^{25}$, $R^{26}$, $R^{27}$, $R^{23}$, $R^{29}$, $R^{30}$, $R^{31}$, $R^{32}$, $R^{33}$ and $R^{34}$ each independently denote hydrogen; a linear or branched, saturated or unsaturated, unsubstituted or mono- or poly-substituted aliphatic group or an unsubstituted or mono- or poly-substituted aryl or heteroaryl group, which optionally may be bound via a linear or branched, unsubstituted or mono- or poly-substituted alkylene group and/or optionally may be condensed with an unsubstituted or mono- or poly-substituted mono- or polycyclic ring system;

$M^1$ denotes an aryl or heteroaryl group, which optionally may be substituted with at least one further substituent and/or optionally may be condensed with an unsubstituted or mono- or poly-substituted mono- or polycyclic ring system; and $M^2$ denotes an aryl or heteroaryl group, which may be unsubstituted or mono- or poly-substituted and optionally may be condensed with an unsubstituted or mono- or poly-substituted mono- or polycyclic ring system;

or a salt thereof.

2. A compound as claimed in claim 1, wherein said compound is present in the form of an isolated stereoisomer.

3. A compound as claimed in claim 1, wherein said compound is present in the form of a mixture of stereoisomers in any mixing ratio.

4. A compound as claimed in claim 3, wherein said compound is present in the form of a racemic mixture.

5. A compound as claimed in claim 1, wherein $R^1$ and $R^2$ each independently denote hydrogen; a halogen; —$NO_2$; —CN; —$NH_2$; —$NHR^5$; —$NR^6R^7$; —NH—C(=O)—$R^8$; —C(=O)—$R^9$; —C(=O)—$NH_2$; —C(=O)—$NHR^{10}$; —C(=O)—$NR^{11}R^{12}$; —C(=O)—$OR^{13}$; —$(CH_2)_m$—C(=O)—$OR^{14}$ with m=1, 2, 3, 4 or 5; —O—C(=O)—$R^{15}$; —$(CH_2)_n$—O—C(=O)—$R^{16}$ with n=1, 2, 3, 4 or 5; —$OR^{17}$; —$(CH_2)_o$—O—$R^{18}$ with o=1, 2, 3; 4 or 5; —$SR^{19}$; —$(CH_2)_p$—S(=O)$_t$—$R^{20}$ with p=1, 2, 3, 4 or 5 and t=0, 1 or 2; —NH—S(=O)$_2$—$NR^{27}R^{28}$; —S(=O)$_2$—$NR^{29}R^{30}$; —$SF_5$; —$(CH_2)_u$—O—S(=O)$_2$—$R^{31}$ with u=1, 2, 3, 4 or 5; —$(CH_2)_v$—O—S(=O)$_2$—O—$R^{32}$ with v=1, 2, 3, 4 or 5; —$(CH_2)_w$—O—P(=O)($OR^{33}$)($OR^{34}$) with w=1, 2, 3, 4 or 5; a linear or branched, unsubstituted or mono- or poly-substituted $C_{1-10}$-alkyl group, $C_{2-6}$-alkenyl group or $C_{2-6}$-alkynyl group; a saturated or unsaturated, unsubstituted or mono- or poly-substituted cycloaliphatic $C_{3-8}$ group optionally having at least one heteroatom as a ring member, which group optionally may be bound via a linear or branched, unsubstituted or mono- or poly-substituted $C_{1-5}$-alkylene group;

or an unsubstituted or mono- or poly-substituted 5- or 6-membered aryl or heteroaryl group, which optionally may be bound via a linear or branched, unsubstituted or mono- or poly-substituted $C_{1-5}$-alkylene group and/or optionally may be condensed with an unsubstituted or mono- or poly-substituted mono- or polycyclic ring system, whereby the rings of the ring system are in each case 5-, 6- or 7-membered;

$R^3$ and $R^4$ each independently denote hydrogen; —C(=O)—$R^{21}$; —$(CH_2)_q$—C(=O)—$R^{22}$ with q=1, 2, 3, 4 or 5; —C(=O)—O—$R^{23}$; —$(CH_2)_r$—C(=O)—O—$R^{24}$ with r=1, 2, 3, 4 or 5; —C(=O)—$NHR^{25}$; —$(CH_2)_s$—C(=O)—$NHR^{26}$ with s=1, 2, 3, 4 or 5; a linear or branched, unsubstituted or mono- or poly-substituted $C_{1-10}$-alkyl group, $C_{2-6}$-alkenyl group or $C_{2-6}$-alkynyl group; a saturated or unsaturated, unsubstituted or mono- or poly-substituted cycloaliphatic $C_{3-8}$ group optionally having at least one heteroatom as a ring member, which group optionally may be bound via a linear or branched, unsubstituted or mono- or poly-substituted $C_{1-5}$-alkylene group; or an unsubstituted or mono- or poly-substituted 5- or 6-membered aryl or heteroaryl group, which optionally may be bound via a linear or branched, unsubstituted or mono- or poly-substituted $C_{1-5}$-alkylene group and/or optionally may be condensed with an unsubstituted or mono- or poly-substituted mono- or polycyclic ring system, whereby the rings of the ring system are in each case 5-, 6- or 7-membered, or $R^3$ and $R^4$ together with the nitrogen atom to which they are bound form a saturated or unsaturated, unsubstituted or mono- or poly-substituted heterocycloaliphatic $C_{4-10}$ group optionally having at least one further heteroatom as a ring member, which group optionally may be condensed with an unsubstituted or mono- or poly-substituted mono- or polycyclic ring system, whereby the rings of the ring system are in each case 5-, 6- or 7-membered;

$R^5$, $R^6$, $R^7$, $R^8$, $R^{10}$, $R^{11}$, $R^{12}$, $R^{15}$ and $R^{16}$ each independently denote a linear or branched, unsubstituted or mono- or poly-substituted $C_{1-10}$-alkyl group, $C_{2-6}$-alkenyl group or $C_{2-6}$-alkynyl group; or an unsubstituted or mono- or poly-substituted 5- to 14-membered aryl or heteroaryl group, which optionally may be bound via a linear or branched, unsubstituted or mono- or poly-substituted $C_{1-5}$-alkylene group and/or optionally may be condensed with an unsubstituted or mono- or poly-substituted mono- or polycyclic ring system, whereby the rings of the ring system are in each case 5-, 6- or 7-membered;

$R^9$, $R^{13}$, $R^{14}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ each independently denote hydrogen; a linear or branched, unsubstituted or mono- or poly-substituted $C_{1-10}$-alkyl group, $C_{2-6}$-alkenyl group or $C_{2-6}$-alkynyl group; or an unsubstituted or mono- or poly-substituted 5- to 14-membered aryl or heteroaryl group, which optionally may be bound via a linear or branched, unsubstituted or mono- or poly-substituted $C_{1-5}$-alkylene group and/or optionally may be condensed with an unsubstituted or mono- or poly-substituted mono- or polycyclic ring system, whereby the rings of the ring system are in each case 5-, 6- or 7-membered;

$M^1$ denotes a 5- or 6-membered aryl or heteroaryl group, which optionally may be substituted with at least one further substituent and optionally may be condensed with an unsubstituted or mono- or poly-substituted mono- or bicyclic ring system, whereby the rings of the ring system are in each case 5-, 6- or 7-membered, and $M^2$ denotes a 5- or 6-membered aryl or heteroaryl group, which can be unsubstituted or mono- or poly-substituted and optionally may be condensed with an unsubstituted or mono- or poly-substituted mono- or bicyclic ring system, whereby the rings of the ring system are in each case 5-, 6- or 7-membered;

wherein said cycloaliphatic groups optionally may contain 1, 2, 3, 4 or 5 heteroatoms each independently selected from the group consisting of nitrogen, oxygen and sulfur as ring members, said heterocycloaliphatic groups optionally may contain 1, 2, 3, 4 or 5 heteroatoms each independently selected from the group consisting of nitrogen, oxygen and sulfur as ring members, said mono- or polycyclic ring systems optionally may contain 0, 1, 2 or 3 heteroatoms each independently selected from the group consisting of oxygen, nitrogen and sulfur as ring members; and said heteroaryl groups optionally may contain 1, 2, 3, 4 or 5 heteroatoms each independently selected from the group consisting of oxygen, sulfur and nitrogen as ring members.

6. A compound as claimed in claim 1, wherein $R^1$ and $R^2$ each independently denote hydrogen; a halogen; —$NO_2$; —CN; —$NH_2$; —$NHR^5$; —$NR^6R^7$; —NH—C(=O)—$R^8$; —C(=O)—$R^9$; —C(=O)—$NH_2$; —C(=O)—$NHR^{10}$; —C(=O)—$NR^{11}R^{12}$; —C(=O)—$OR^{13}$; —$(CH_2)_m$—C(=O)—$OR^{14}$ with m=1, 2 or 3; —O—C(=O)—$R^{15}$; —$(CH_2)_n$—O—C(=O)—$R^{16}$ with n=1, 2 or 3; —$OR^{17}$; —$(CH_2)_o$—O—$R^{18}$ with o=1, 2 or 3; —$SR^{19}$; —$(CH_2)_p$—S(=O)$_t$—$R^{20}$ with p=1, 2 or 3 and t=0, 1 or 2; —NH—S(=O)$_2$—$NR^{27}R^{28}$; —S(=O)$_2$—$NR^{29}R^{30}$; —$SF_5$; —$(CH_2)_u$—O—S(=O)$_2$—$R^{31}$ with u=1, 2 or 3; —$(CH_2)_v$—O—S(=O)$_2$—O—$R^{32}$ with v=1, 2 or 3; —$(CH_2)_w$—O—P(=O)($OR^{33}$)($OR^{34}$) with w=1, 2 or 3; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —$CF_3$, —$CF_2H$, —$CFH_2$, —($CH_2$)—OH, —($CH_2$)—$NH_2$, —($CH_2$)—CN, —($CH_2$)—($CF_3$), —($CH_2$)—($CHF_2$), —($CH_2$)—($CH_2F$), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CH_2$)—($CF_3$) and —($CH_2$)—($CH_2$)—($CH_2$)—OH; a group selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl, which optionally may be unsubstituted or substituted with 1, 2, 3 or 4 substituents independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si($CH_3$)$_3$, —C≡C—Si($C_2H_5$)$_3$, —C≡C—Si($CH_3$)$_3$, —C≡Si($C_2H_5$)$_3$, —$CH_2$—O—$CH_3$, —$CH_2$—O—$C_2H_5$, —OH, —SH, —$SF_5$, —$NH_2$, oxo (=O), thioxo (=S), —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —N($CH_3$)$_2$, —N($C_2H_5$)$_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—C($CH_3$)$_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—N($CH_3$)$_2$, phenyl, furyl (furanyl), thiadiazolyl, thiophenyl (thienyl) and benzyl; or a group selected from the group consisting of phenyl, benzyl, phenethyl, (3-phenyl)-prop-1-yl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which optionally may be unsubstituted or substituted with 1, 2, 3, 4 or 5 substituents independently selected from the group consisting of F, Cl, Br, I, —CN, —$NO_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si($CH_3$)$_3$, —C≡C—Si($C_2H_5$)$_3$, —$CH_2$—O—$CH_3$, —$CH_2$—O—$C_2H_5$, —OH, —SH, —$SF_5$, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, —N($CH_3$)$_2$, —N($C_2H_5$)$_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—C($CH_3$)$_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—N($CH_3$)$_2$, —Si(phenyl)$_2$[C($CH_3$)$_3$], (1,3)-dioxolanyl, cyclopropyl, cyclobutyl, cyclopentyl, cyclohexyl, phenyl, furyl (furanyl), thiadiazolyl, thiophenyl (thienyl) and benzyl.

7. A compound as claimed in claim 1, wherein $R^3$ and $R^4$ each independently denote hydrogen; —C(=O)—$R^{21}$; —$(CH_2)_q$—C(=O)—$R^{22}$ with q=1, 2 or 3; —C(=O)—O—$R^{23}$; —$(CH_2)_r$—C(=O)—O—$R^{24}$ with r=1, 2 or 3; —C(=O)—$NHR^{25}$; —$(CH_2)_s$—C(=O)—$NHR^{26}$ with s=1, 2 or 3; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —$CF_3$, —$CF_2H$, —$CFH_2$, —($CH_2$)—OH, —($CH_2$)—$NH_2$, —($CH_2$)—CN, —($CH_2$)—($CF_3$), —($CH_2$)—($CHF_2$), —($CH_2$)—($CH_2F$), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CH_2$)—($CF_3$) and —($CH_2$)—($CH_2$)—($CH_2$)—OH; a group selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl, which optionally may be unsubstituted or substituted with 1, 2, 3 or 4 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, oxo (=O), thioxo (=S), —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl and/or optionally may be bound via a linear or branched C$_{1-3}$-alkylene group; or a group selected from the group consisting of phenyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], (1,3)-dioxolanyl, cyclopropyl, cyclobutyl, cyclopentyl, cyclohexyl, phenyl, furyl (furanyl), thiadiazolyl, thiophenyl (thienyl) and benzyl and/or optionally may be bound via a linear or branched C$_{1-3}$-alkylene group; or R$^3$ and R$^4$ together with the nitrogen atom to which they are bound form a group selected from the group consisting of imidazolidinyl, piperidinyl, piperazinyl, morpholinyl, pyrrolidinyl, thiomorpholinyl, azepanyl, diazepanyl and azocanyl, which optionally may be unsubstituted or substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —OH, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —SF$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH—S(=O)$_2$—CH$_3$, —C(=O)—OH, —C(=O)—H; —C(=O)—CH$_3$, —C(=O)—C$_2$H$_5$, —C(=O)—N(CH$_3$)$_2$, —C(=O)—NH—CH$_3$, —C(=O)—NH$_2$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl.

8. A compound as claimed in claim 1, wherein R$^5$, R$^6$, R$^7$, R$^8$, R$^{10}$, R$^{11}$, R$^{12}$, R$^{15}$ and R$^{16}$ each independently denote a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—NH—CH$_3$, —(CH$_2$)—N(CH$_3$)$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$), —(CH$_2$)—(CH$_2$)—(CH$_2$)—OH, —(CH$_2$)—C(=O)—OH, —(CH$_2$)—C(=O)—O—CH$_3$, —(CH$_2$)—C(=O)—O—C$_2$H$_5$, —(CH$_2$)—(CH$_2$)—C(=O)—OH, —(CH$_2$)—(CH$_2$)—C(=O)—O—CH$_3$ and —(CH$_2$)—(CH$_2$)—C(=O)—O—C$_2$H$_5$; or a group selected from the group consisting of phenyl, benzyl, phenethyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

9. A compound as claimed in claim 1, wherein R$^9$, R$^{13}$, R$^{14}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$, R$^{33}$ and R$^{34}$ each independently denote hydrogen; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—OH, —(CH$_2$)—NH$_2$, —(CH$_2$)—NH—CH$_3$, —(CH$_2$)—N(CH$_3$)$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—

NH₂, —(CH₂)—(CH₂)—CN, —(CF₂)—(CF₃), —(CH₂)—(CH₂)—(CF₃), —(CH₂)—(CH₂)—(CH₂)—OH, —(CH₂)—C(=O)—OH, —(CH₂)—C(=O)—O—CH₃, —(CH₂)—C(=O)—O—C₂H₅, —(CH₂)—(CH₂)—C(=O)—OH, —(CH₂)—(CH₂)—C(=O)—O—CH₃ and —(CH₂)—(CH₂)—C(=O)—O—C₂H₅;

or a group selected from the group consisting of phenyl, benzyl, phenethyl, furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl, pentazolyl, indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl, which optionally may be unsubstituted or substituted with 1, 2, 3, 4 or 5 substituents independently selected from the group consisting of F, Cl, Br, I, —CN, —NO₂, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF₅, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂ and —S—CH₂F.

10. A compound as claimed in claim 1, wherein $M^1$ denotes a group selected from the group consisting of phenyl, furanyl, thiophenyl (thienyl), pyrazolyl, pyrazinyl, pyridazinyl, pyrimidinyl, pyridinyl, pyrrolyl, oxazolyl, isoxazolyl, thiazolyl, thiadiazolyl, imidazolyl, oxadiazolyl, triazolyl, diazinyl, triazinyl, tetrazinyl and tetrazolyl, which optionally may be unsubstituted or substituted with 1, 2, 3 or 4 substituents independently selected from the group consisting of F, Cl, Br, I, —CN, —CH₂—CN, —NO₂, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF₅, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂ and —S—CH₂F.

11. A compound as claimed in claim 10, wherein $M^1$ denotes a group selected from the group consisting of groups 1 to 38

1

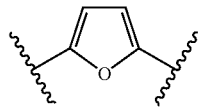

2

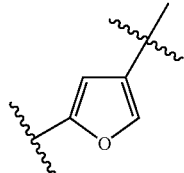

-continued

3

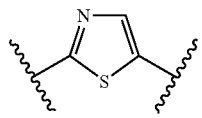

4

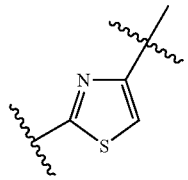

5

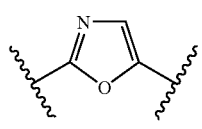

6

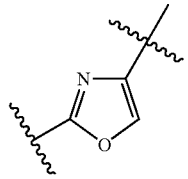

7

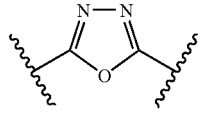

8

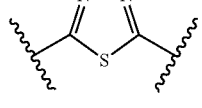

9

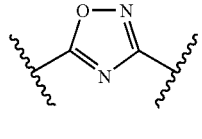

10

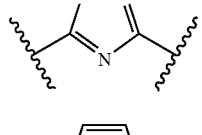

11

12

13

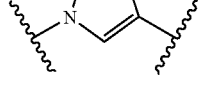

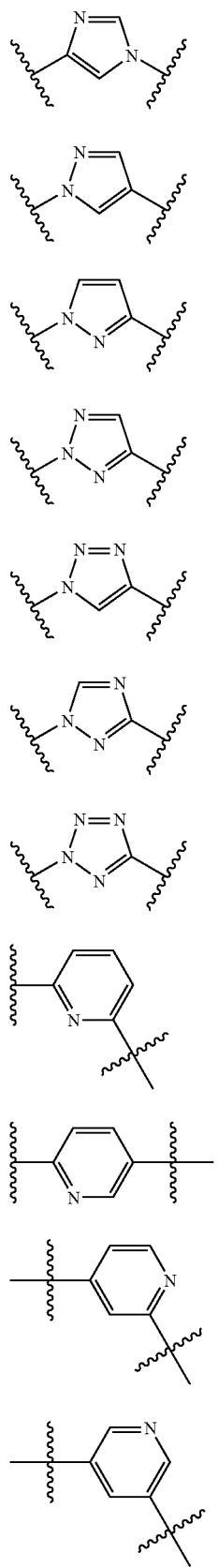
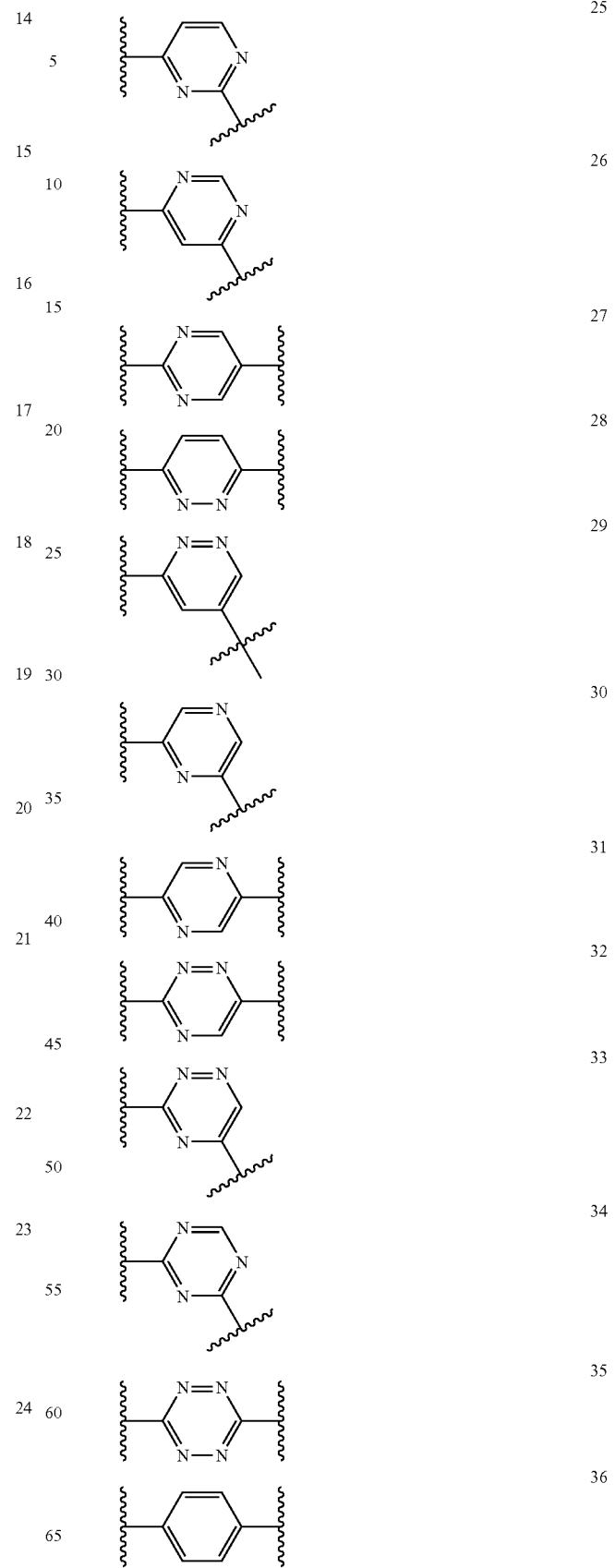

-continued

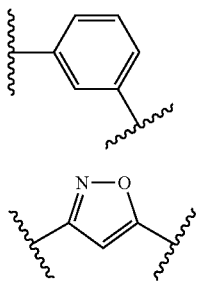

37

38 which optionally may be unsubstituted or substituted with 1, 2, 3 or 4 substituents independently selected from the group consisting of F, Cl, Br, I, —CN, —CH$_2$—CN, —NO$_2$, methyl, ethyl, n-propyl, isopropyl, n-butyl, isobutyl, 2-butyl, tert-butyl, n-pentyl, neopentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F, and which in each case can be linked in any direction via the positions marked by a wavy line with the bicyclic ring system and the carbon atom of the triple bond.

12. A compound as claimed in claim 1, wherein
M$^2$ denotes a group selected from the group consisting of phenyl, furanyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —Si(phenyl)$_2$[C(CH$_3$)$_3$], —CH$_2$—NH$_2$, pyrrolyl, —NH—S(=O)$_2$—C$_2$H$_5$, —S(=O)$_2$—NH$_2$, —S(=O)$_2$—NH—CH$_3$, —CH$_2$—OH, —NH—C(=NH)—NH$_2$, —NH—S(=O)$_2$—OH, —S(=O)$_2$—N(CH$_3$)$_2$, (1,3)-dioxolanyl, cyclopropyl, cyclobutyl, cyclopentyl, cyclohexyl, phenyl, furyl (furanyl), thiadiazolyl, thiophenyl (thienyl) and benzyl.

13. A compound as claimed in claim 12, wherein
M$^2$ denotes a group selected from the group consisting of groups 1 to 36,

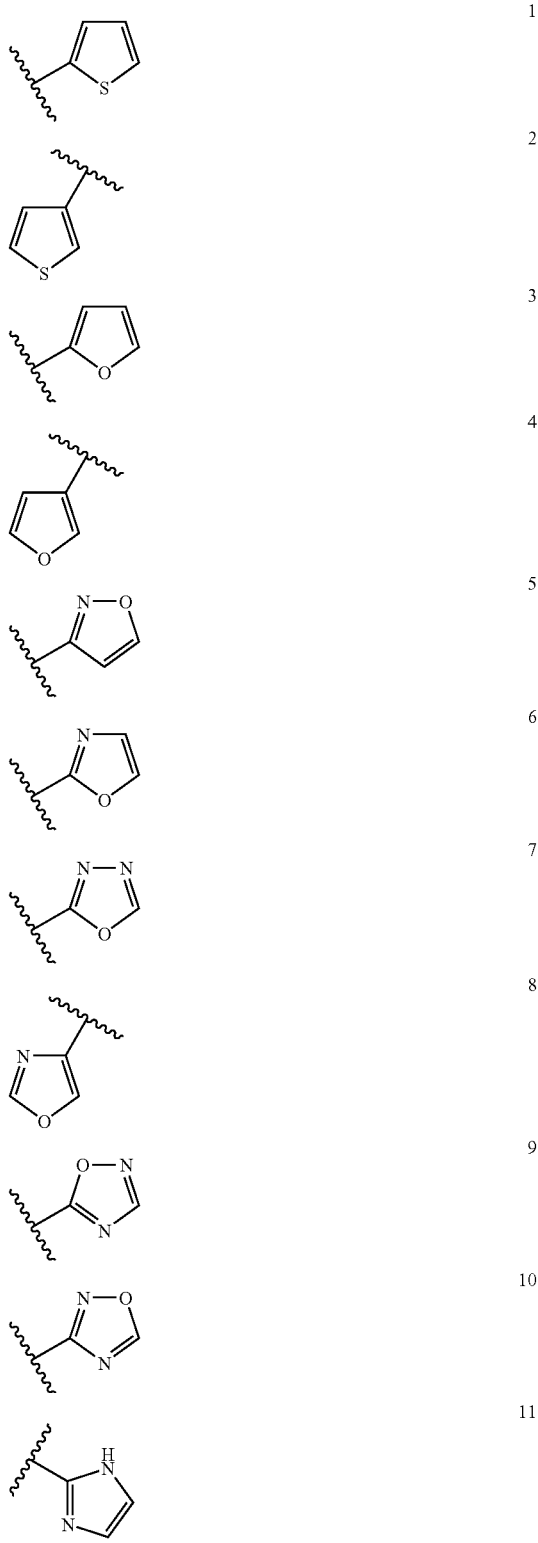

-continued
| | |
|---|---|
| 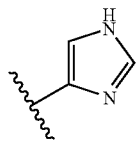 12 | 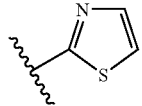 5 |
| 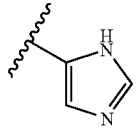 13 | 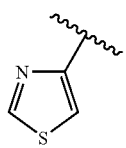 10 |
| 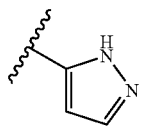 14 | 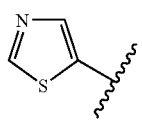 15 |
| 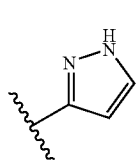 15 | 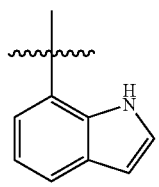 20 25 |
| 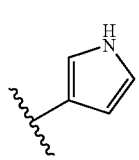 16 | 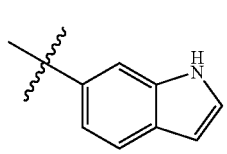 30 |
| 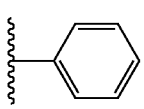 17 | 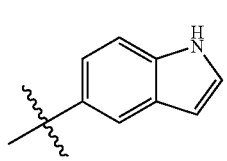 35 |
| 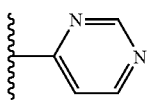 18 | 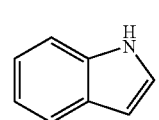 40 |
| 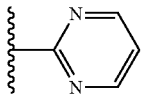 19 | 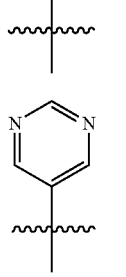 45 50 |
| 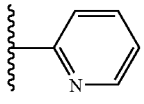 20 | |
| 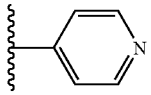 21 | 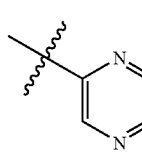 55 |
| 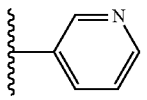 22 | 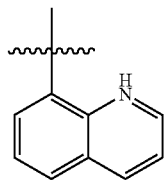 60 65 |
| 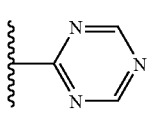 23 | |

-continued

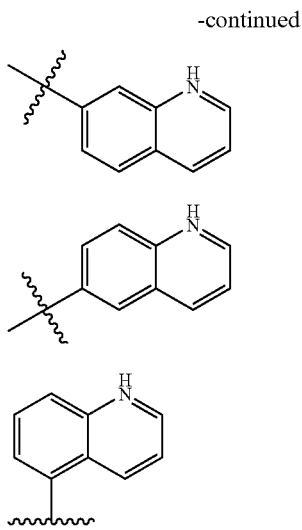

34

35

36 which in each case can be linked via the position marked by a wavy line with the carbon atom of the triple bond and optionally may be unsubstituted or substituted with 1, 2, 3, 4 or 5 substituents independently selected from the group consisting of F, Cl, Br, —CN, —CF$_3$, —SF$_5$, —S—CH$_3$, —S—C$_2$H$_5$, methyl, ethyl, n-propyl, isopropyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

14. A compound as claimed in claim 1, wherein

R$^1$ and R$^2$ each independently denote hydrogen; —F; —Cl; —Br; —I; —NO$_2$; —CN; —NH$_2$; —NHR$^5$; —NR$^6$R$^7$; —C(=O)—R$^9$, —C(=O)—NH$_2$; —C(=O)—NHR$^{10}$; —C(=O)—NR$^{11}$R$^{12}$; —C(=O)—OR$^{13}$; —(CH$_2$)$_m$—C(=O)—OR$^{14}$ with m=1, 2 or 3; —O—C(=O)—R$^{15}$; —OR$^{17}$; —(CH$_2$)$_o$—O—R$^{18}$ with o=1, 2 or 3; —S(=O)$_2$—NH$_2$; —SF$_5$; —(CH$_2$)$_u$—O—S(=O)$_2$—R$^{31}$ with u=1, 2 or 3; —(CH$_2$)$_v$—O—S(=O)$_2$—O—R$^{32}$ with v=1, 2 or 3; —(CH$_2$)$_w$—O—P(=O)(OR$^{33}$)(OR$^{34}$) with w=1, 2 or 3; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); a group selected from the group consisting of cyclopropyl, cyclobutyl, cyclopentyl, cyclohexyl, cycloheptyl and cyclooctyl, which optionally may be unsubstituted or substituted with 1, 2, 3 or 4 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, —OH, oxo (=O), thioxo (=S), —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F; or a group selected from the group consisting of phenyl, benzyl, phenethyl, (3-phenyl)-prop-1-yl, furyl (furanyl), thienyl (thiophenyl), pyrazolyl, imidazolyl, thiazolyl, thiadiazolyl, pyridinyl, pyridazinyl, pyrimidinyl and pyrazinyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —C(=O)—O—CH$_3$, —C(=O)—O—C$_2$H$_5$, —C(=O)—O—C(CH$_3$)$_3$, cyclopropyl, cyclobutyl, cyclopentyl, cyclohexyl and phenyl;

R$^3$ and R$^4$ each independently denote hydrogen; —C(=O)—R$^{21}$; —(CH$_2$)$_q$—C(=O)—R$^{22}$ with q=1, 2 or 3; —C(=O)—O—R$^{23}$; —(CH$_2$)$_r$—C(=O)—O—R$^{24}$ with r=1, 2 or 3; —C(=O)—NHR$^{25}$; —(CH$_2$)$_3$—C(=O)—NHR$^{26}$ with s=1, 2 or 3; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; a group selected from the group consisting of cyclopropyl, cyclobutyl, cyclopentyl, cyclohexyl, cycloheptyl and cyclooctyl, which optionally may be unsubstituted or substituted with 1, 2, 3 or 4 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, —OH, oxo (=O), thioxo (=S), —O—CH$_3$, —O—C$_2$H$_5$, —O—C$_3$H$_7$ and —O—C(CH$_3$)$_3$ and/or optionally may be bound via a linear or branched C$_{1-3}$-alkylene group; or a group selected from the group consisting of phenyl, furyl (furanyl), thienyl (thiophenyl), pyrazolyl, imidazolyl, thiazolyl, thiadiazolyl, pyridinyl, pyridazinyl, pyrimidinyl and pyrazinyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, —OH, —SH, —SF$_5$, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —N(CH$_3$)$_2$, —N(C$_2$H$_5$)$_2$, —NH—CH$_3$, —NH—C$_2$H$_5$, cyclopropyl, cyclobutyl and cyclopentyl and/or optionally may be bound via a linear or branched C$_{1-3}$-alkylene group; or R$^3$ and R$^4$ together with the nitrogen atom to which they are bound form a group selected from the group consisting of imidazolidinyl, piperidinyl, piperazinyl, morpholinyl, pyrrolidinyl, thiomorpholinyl, azepanyl, diazepanyl and azocanyl, which optionally may be unsubstituted or substituted with 1, 2, 3, 4 or 5 substituents independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —SF$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —C(=O)—CH$_3$, —C(=O)—C$_2$H$_5$, —C(=O)—N(CH$_3$)$_2$, —C(=O)—NH—CH$_3$, —C(=O)—NH$_2$, —C(=O)—O—CH$_3$, —C(=O)—O—C$_2$H$_5$, —C(=O)—O—C(CH$_3$)$_3$ and phenyl;

R$^5$, R$^6$, R$^7$, R$^{10}$, R$^{11}$, R$^{12}$ and R$^{15}$ each independently denote a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CHF$_2$), —(CH$_2$)—(CH$_2$F), —(CF$_2$)—(CF$_3$), —(CH$_2$)—(CH$_2$)—C(=O)—OH, —(CH$_2$)—(CH$_2$)—C(=O)—O—CH$_3$ and —(CH$_2$)—(CH$_2$)—C(=O)—O—C$_2$H$_5$; or a group selected from the group consisting of phenyl, benzyl, phenethyl, furyl (furanyl), thienyl (thiophenyl), pyrazolyl, imidazolyl, thiazolyl, thiadiazolyl, pyridinyl, pyridazinyl, pyrimidinyl and pyrazinyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, —OH, —SH, —SF$_5$, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F and —C(=O)—CF$_3$;

R$^9$, R$^{13}$, R$^{14}$, R$^{17}$, R$^{18}$, R$^{21}$, R$^{22}$, R$^{23}$, R$^{24}$, R$^{25}$, R$^{26}$, R$^{31}$, R$^{32}$, R$^{33}$ and R$^{34}$ each independently denote hydrogen; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); or a group selected from the group consisting of phenyl, benzyl, phenethyl, furyl (furanyl), thienyl (thiophenyl), pyrazolyl, imidazolyl, thiazolyl, thiadiazolyl, pyridinyl, pyridazinyl, pyrimidinyl and pyrazinyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, —OH, —SH, —SF$_5$, —NH$_2$, —C(=O)—OH, —S—CH$_3$, —S—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F and —C(=O)—CF$_3$;

M$^1$ denotes a group selected from the group consisting of groups 1 to 9, 11, 21, 22 and 36 to 38,

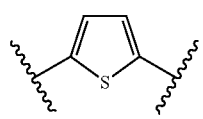

1

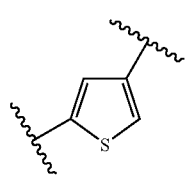

2

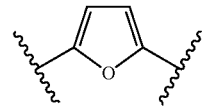

3

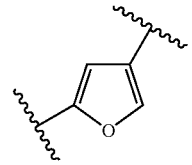

4

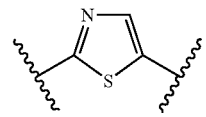

5

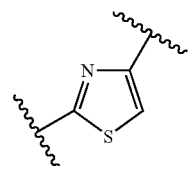

6

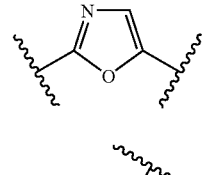

7

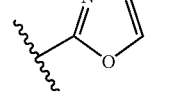

8

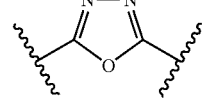

9

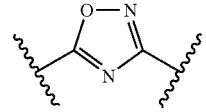

11

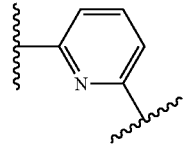

21

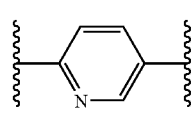

22

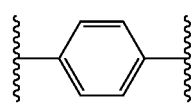

36

-continued

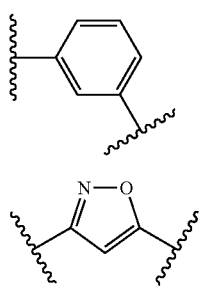
37

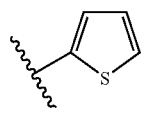
38 which optionally may be unsubstituted or substituted with 1 or 2 substituents independently selected from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —OH, —SH, —SF$_5$, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F, and which in each case can be linked in any direction via the positions marked by a wavy line with the bicyclic ring system and the carbon atom of the triple bond; and M$^2$ denotes a group selected from the group consisting of groups 1 to 36

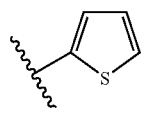
1

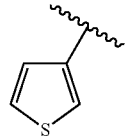
2

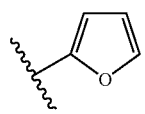
3

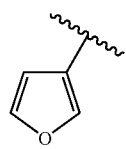
4

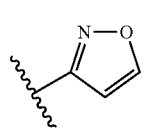
5

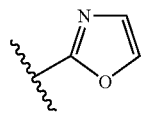
6

-continued

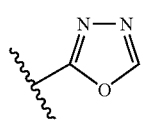
7

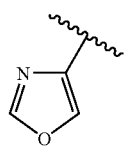
8

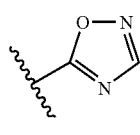
9

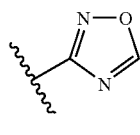
10

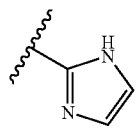
11

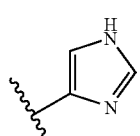
12

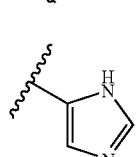
13

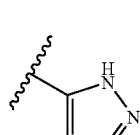
14

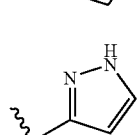
15

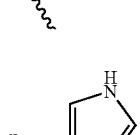
16

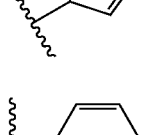
17

-continued

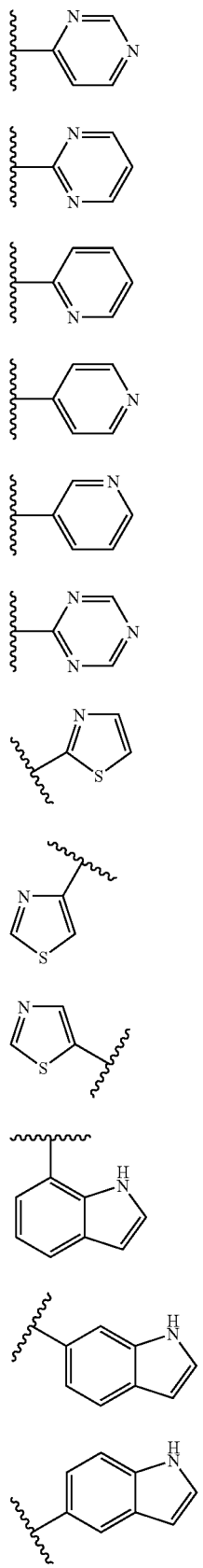

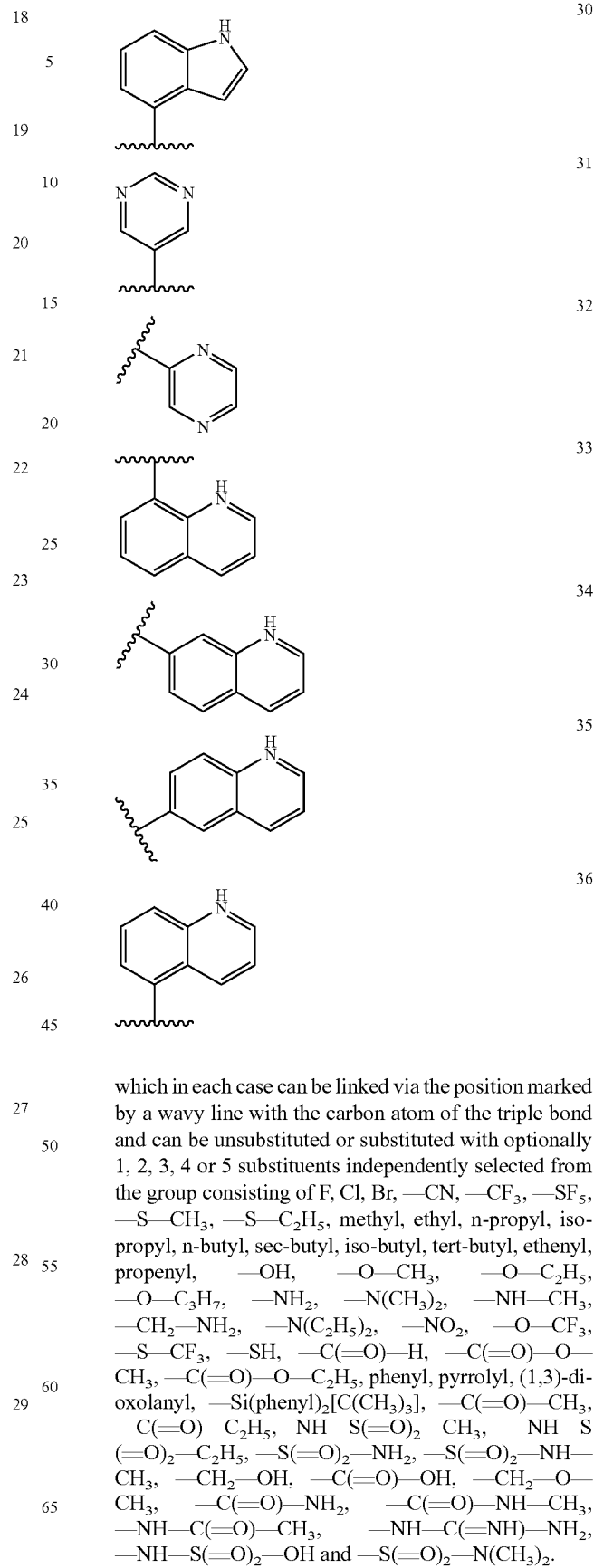

which in each case can be linked via the position marked by a wavy line with the carbon atom of the triple bond and can be unsubstituted or substituted with optionally 1, 2, 3, 4 or 5 substituents independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

15. A compound as claimed in claim 1, wherein $R^1$ and $R^2$ each independently denote hydrogen; —F; —Cl; —Br; —I; —NO$_2$; —CN; —NHR$^5$; —NR$^6$R$^7$; —C(=O)—R$^9$, —C(=O)—OR$^{13}$; —(CH$_2$)—O—C(=O)—R$^{16}$; OR$^{17}$; —(CH$_2$)—O—S(=O)$_2$—R$^{31}$; —(CH$_2$)—O—S(=O)$_2$—O—R$^{32}$; —(CH$_2$)—O—P(=O)(OR$^{33}$)(OR$^{34}$); —SF$_5$; a group selected from the group consisting of methyl, ethyl, n-propyl, isopropyl, n-butyl, isobutyl, 2-butyl, tert-butyl, n-pentyl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); a group selected from the group consisting of cyclopropyl, cyclobutyl, cyclopentyl, cyclohexyl, cycloheptyl and cyclooctyl; or a group selected from the group consisting of phenyl, benzyl, phenethyl and (3-phenyl)-prop-1-yl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F;

$R^3$ and $R^4$ each independently denote hydrogen; —C(=O)—R$^{21}$; —(CH$_2$)$_q$—C(=O)—R$^{22}$ with q=1, 2 or 3; —(CH$_2$)$_r$—C(=O)—O—R$^{24}$ with r=1, 2 or 3; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; a group selected from the group consisting of cyclopropyl, cyclobutyl, cyclopentyl, cyclohexyl, cycloheptyl and cyclooctyl, which optionally may be bound via a —(CH$_2$)—, —(CH$_2$)$_2$—, —(CH(CH$_3$))— or —(CH$_2$)$_3$ group; or a group selected from the group consisting of phenyl, furyl (furanyl), thienyl (thiophenyl), pyridinyl, pyridazinyl, pyrimidinyl and pyrazinyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$ and —O—CH$_2$F and/or optionally may be bound via a —(CH$_2$)—, —(CH$_2$)$_2$—, —(CH(CH$_3$))— or —(CH$_2$)$_3$ group; or $R^3$ and $R^4$ together with the nitrogen atom to which they are bound form a group selected from the group consisting of piperidinyl, piperazinyl, morpholinyl and pyrrolidinyl, which optionally may be unsubstituted or substituted with 1, 2, 3, 4 or 5 substituents independently selected from the group consisting of methyl, ethyl, n-propyl, isopropyl, n-butyl, 2-butyl, isobutyl, tert-butyl, —S(=O)—CH$_3$, —S(=O)$_2$—CH$_3$, —S(=O)—C$_2$H$_5$, —S(=O)$_2$—C$_2$H$_5$, —C(=O)—CH$_3$, —C(=O)—C$_2$H$_5$, —C(=O)—N(CH$_3$)$_2$, —C(=O)—NH—CH$_3$, —C(=O)—NH$_2$, —C(=O)—O—CH$_3$, —C(=O)—O—C$_2$H$_5$ and —C(=O)—O—C(CH$_3$)$_3$;

$R^5$, $R^6$, $R^7$ and $R^{16}$ each independently denote a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CHF$_2$), —(CH$_2$)—(CH$_2$F), —(CF$_2$)—(CF$_3$), —(CH$_2$)—(CH$_2$)—C(=O)—OH; —(CH$_2$)—(CH$_2$)—C(=O)—O—CH$_3$ and —(CH$_2$)—(CH$_2$)—C(=O)—O—C$_2$H$_5$; or a group selected from the group consisting of phenyl, benzyl and phenethyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$ and —O—C$_2$H$_5$;

$R^9$, $R^{13}$, $R^{17}$, $R^{21}$, $R^{22}$, $R^{24}$, $R^{31}$, $R^{32}$, $R^{33}$ and $R^{34}$ each independently denote hydrogen; a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF$_3$, —CF$_2$H, —CFH$_2$, —(CH$_2$)—(CF$_3$), —(CH$_2$)—(CHF$_2$), —(CH$_2$)—(CH$_2$F) and —(CF$_2$)—(CF$_3$); or a group selected from the group consisting of phenyl, benzyl and phenethyl, which optionally may be unsubstituted or substituted with 1, 2, 3, 4 or 5 substituents independently selected from the group consisting of F, Cl, Br, I, —CN, —NO$_2$, methyl, ethyl, n-propyl, isopropyl, n-butyl, isobutyl, 2-butyl, tert-butyl, —O—CH$_3$ and —O—C$_2$H$_5$;

$M^1$ denotes a group selected from the group consisting of groups 1 to 6, 21, 22, 36 and 37,

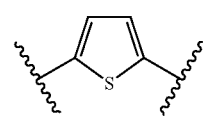

1

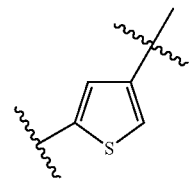

2

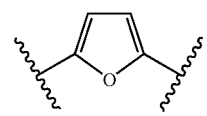

3

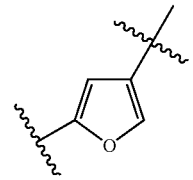

4

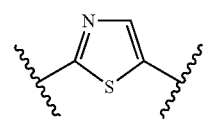

5

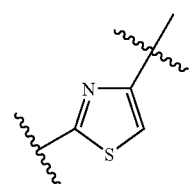

6

-continued

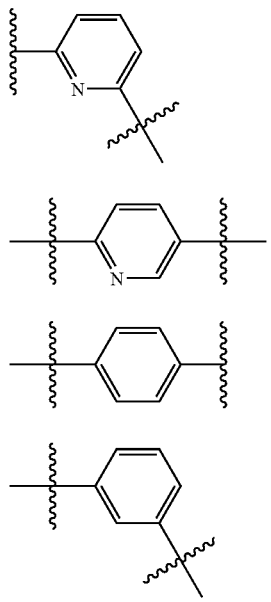

which optionally may be unsubstituted or substituted with 1 or 2 substituents independently selected from the group consisting of F, Cl, Br, I, —CN, —CH₂—CN, —NO₂, methyl, ethyl, n-propyl, isopropyl, n-butyl, isobutyl, 2-butyl, tert-butyl, n-pentyl, neo-pentyl, —SF₅, —O—CH₃, —O—C₂H₅, —O—C₃H₇, —O—C(CH₃)₃, —CF₃, —CHF₂, —CH₂F, —O—CF₃, —O—CHF₂ and —O—CH₂F, and which in each case can be linked in any direction via the positions marked by a wavy line with the bicyclic ring system and the carbon atom of the triple bond; and M² denotes a group selected from the group consisting of phenyl, 2-pyridinyl, 3-pyridinyl, 4-pyridinyl, 2-thiazolyl, 4-thiazolyl, 5-thiazolyl, 4-indolyl, 5-indolyl, 6-indolyl, 7-indolyl, 2-thiophenyl (2-thienyl), 3-thiophenyl (3-thienyl), 2-imidazolyl, 4-imidazolyl, 5-imidazolyl, 2-pyrimidinyl, 4-pyrimidinyl, 5-pyrimidinyl, 2-pyrazinyl, 5-quinolinyl, 6-quinolinyl, 7-quinolinyl and 8-quinolinyl, which optionally may be unsubstituted or substituted with 1, 2, 3, 4 or 5 substituents independently selected from the group consisting of F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂.

16. A compound as claimed in claim 15, corresponding to formula Ia

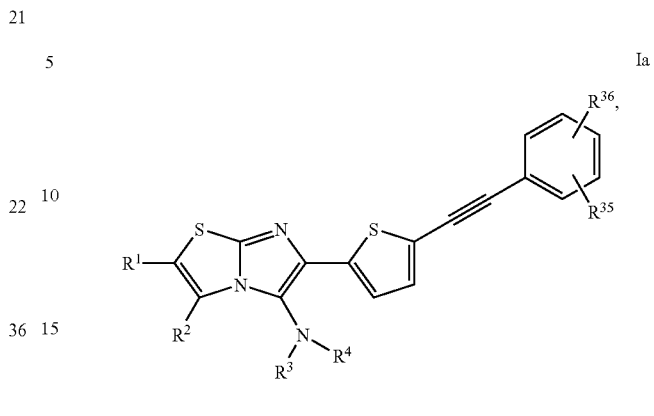

wherein
R¹, R², R³ and R⁴ have the meanings given in claim 15, and R³⁵ and R³⁶ each independently denote a group selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂.

17. A compound as claimed in claim 15, corresponding to formula Ib

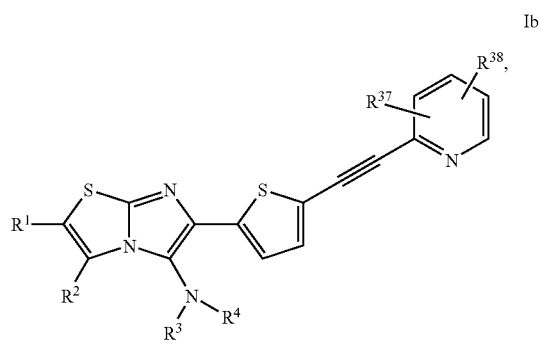

wherein
R¹, R², R³ and R⁴ have the meanings given in claim 15, and R³⁷ and R³⁸ each independently denote a group selected from the group consisting of H, F, Cl, Br, —CN, —CF₃, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S (=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

18. A compound as claimed in claim 15, corresponding to formula Ic

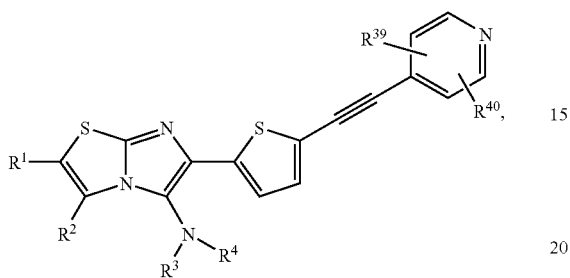

wherein

R$^1$, R$^2$, R$^3$ and R$^4$ have the meanings given in claim 15, and R$^{39}$ and R$^{40}$ each independently denote a group selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

19. A compound as claimed in claim 15, corresponding to formula Id

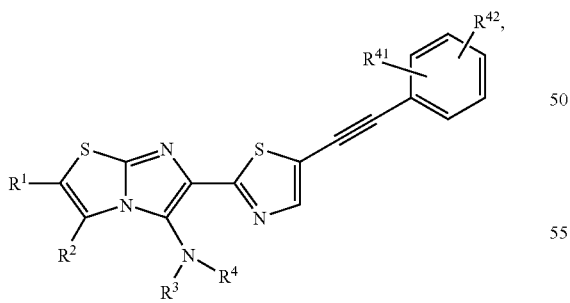

wherein

R$^1$, R$^2$, R$^3$ and R$^4$ have the meanings given in claim 15, and R$^{41}$ and R$^{42}$ each independently denote a group selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

20. A compound as claimed in claim 15, corresponding to formula Ie

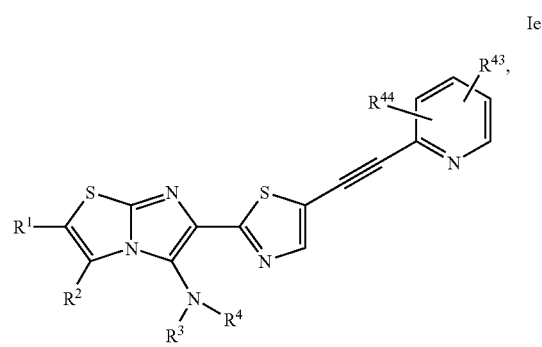

wherein

R$^1$, R$^2$, R$^3$ and R$^4$ have the meanings given in claim 15, and R$^{43}$ and R$^{44}$ each independently denote a group selected from the group consisting of H, F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

21. A compound as claimed in claim 15, corresponding to formula If

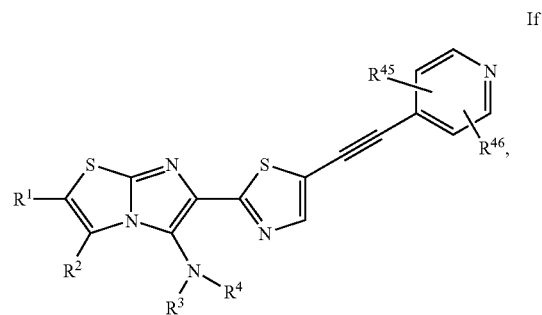

wherein

R$^1$, R$^2$, R$^3$ and R$^4$ have the meanings given in claim 15, and R$^{45}$ and R$^{46}$ each independently denote a group selected from the group consisting of H, F, Cl, Br, —CN, —CF$_3$, —SF₅, —S—CH₃, —S—C₂H₅, methyl, ethyl, n-propyl, iso-propyl, n-butyl, sec-butyl, iso-butyl, tert-butyl, ethenyl, propenyl, —OH, —O—CH₃, —O—C₂H₅, —O—C₃H₇, —NH₂, —N(CH₃)₂, —NH—CH₃, —CH₂—NH₂, —N(C₂H₅)₂, —NO₂, —O—CF₃, —S—CF₃, —SH, —C(=O)—H, —C(=O)—O—CH₃, —C(=O)—O—C₂H₅, phenyl, pyrrolyl, (1,3)-dioxolanyl, —Si(phenyl)₂[C(CH₃)₃], —C(=O)—CH₃, —C(=O)—C₂H₅, NH—S(=O)₂—CH₃, —NH—S(=O)₂—C₂H₅, —S(=O)₂—NH₂, —S(=O)₂—NH—CH₃, —CH₂—OH, —C(=O)—OH, —CH₂—O—CH₃, —C(=O)—NH₂, —C(=O)—NH—CH₃, —NH—C(=O)—CH₃, —NH—C(=NH)—NH₂, —NH—S(=O)₂—OH and —S(=O)₂—N(CH₃)₂.

22. A compound as claimed in claim 1, wherein

R¹ denotes hydrogen; —F; —Cl; —Br; —CN; —O—CH₃; —C(=O)—R⁹, —C(=O)—OR¹³; —(CH₂)—O—C(=O)—R¹⁶; —(CH₂)—O—S(=O)₂—R³¹; —(CH₂)—O—S(=O)₂—O—R³²; —(CH₂)—O—P(=O)(OR³³)(OR³⁴); or a group selected from the group consisting of methyl, ethyl, n-propyl, isopropyl, n-butyl, isobutyl, 2-butyl, tert-butyl, n-pentyl, —CF₃, —CF₂H, —CFH₂, —(CH₂)—(CF₃), —(CH₂)—(CHF₂), —(CH₂)—(CH₂F), and —(CF₂)—(CF₃);

R² denotes hydrogen; —F; —Cl; —Br; —CN; —O—CH₃; —C(=O)—R⁹, —C(=O)—OR¹³; —(CH₂)—O—C(=O)—R¹⁶; —(CH₂)—O—S(=O)₂—R³¹; —(CH₂)—O—S(=O)₂—O—R³²; —(CH₂)—O—P(=O)(OR³³)(OR³⁴); or a group selected from the group consisting of methyl, ethyl, n-propyl, isopropyl, n-butyl, isobutyl, 2-butyl, tert-butyl, n-pentyl, —CF₃, —CF₂H, —CFH₂, —(CH₂)—(CF₃), —(CH₂)—(CHF₂), —(CH₂)—(CH₂F), and —(CF₂)—(CF₃);

R³ denotes hydrogen or a group selected from the group consisting of methyl, ethyl and isopropyl;

R⁴ denotes hydrogen; —C(=O)—R²¹ or a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl and (2,4,4)-trimethyl-pent-2-yl; or R³ and R⁴ together with the nitrogen atom to which they are bound form a group selected from the group consisting of pyrrolidinyl, piperidinyl and morpholinyl;

R¹⁶ denotes a group selected from the group consisting of —(CH₂)—(CH₂)—C(=O)—OH; —(CH₂)—(CH₂)—C(=O)—O—CH₃ and —(CH₂)—(CH₂)—C(=O)—O—C₂H₅;

R⁹, R¹³, R³¹, R³², R³³ and R³⁴ each independently denote hydrogen; or a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF₃, —CF₂H, —CFH₂, —(CH₂)—(CF₃), —(CH₂)—(CHF₂), —(CH₂)—(CH₂F) and —(CF₂)—(CF₃);

R²¹ denotes a group selected from the group consisting of methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, n-heptyl, n-octyl, (2,4,4)-trimethyl-pent-2-yl, —CF₃, —CF₂H, —CFH₂, —(CH₂)—(CF₃), —(CH₂)—(CHF₂), —(CH₂)—(CH₂F) and —(CF₂)—(CF₃) or a phenyl group, which optionally may be unsubstituted or substituted with 1, 2, 3, 4 or 5 substituents independently selected from the group consisting of F, Cl, Br, I, —CN, —NO₂, methyl, ethyl, n-propyl, isopropyl, n-butyl, isobutyl, 2-butyl, tert-butyl, —O—CH₃ and —O—C₂H₅;

M¹ denotes a group selected from the group consisting of groups 1, 3, 5, 22, 36 and

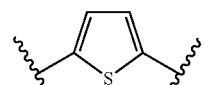
1

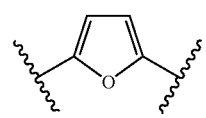
3

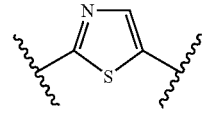
5

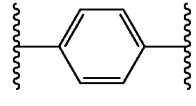
36

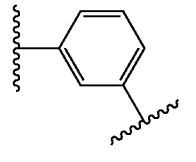
37

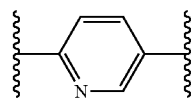
22 which in each case is unsubstituted, and which in each case can be linked in any direction via the positions marked by a wavy line with the bicyclic ring system and the carbon atom of the triple bond; and M² denotes a group selected from the group consisting of phenyl, 2-pyrimidinyl, 5-pyrimidinyl, 2-thiophenyl (2-thienyl), 3-thiophenyl (3-thienyl), 2-pyridinyl, 3-pyridinyl, 4-pyridinyl, 2-thiazolyl and 4-thiazolyl, which optionally may be unsubstituted or substituted with 1, 2, 3, 4 or 5 substituents independently selected from the group consisting of F, Cl, Br, —CN, —O—CH₃, —OH, —CF₃, methyl, ethyl, n-propyl, iso-propyl, n-butyl, sec-butyl, iso-butyl and tert-butyl.

23. A compound as claimed in claim 1, wherein

R¹ denotes hydrogen; —F; —Cl; —Br; —CN; —C(=O)—OR¹³; or a group selected from the group consisting of methyl, ethyl, n-propyl, isopropyl, n-butyl, isobutyl, 2-butyl, tert-butyl and n-pentyl;

R² denotes hydrogen; —F; —Cl; —Br; —CN; —C(=O)—OR¹³; or a group selected from the group consisting of methyl, ethyl, n-propyl, isopropyl, n-butyl, isobutyl, 2-butyl, tert-butyl and n-pentyl;

R³ denotes hydrogen;

R⁴ denotes hydrogen; —C(=O)—R²¹ or a group selected from the group consisting of methyl, ethyl, n-propyl, isopropyl, n-butyl, isobutyl, 2-butyl, tert-butyl, n-pentyl and (2,4,4)-trimethyl-pent-2-yl;

R¹³ denotes a group selected from the group consisting of methyl, ethyl, n-propyl, isopropyl, n-butyl, isobutyl, 2-butyl, tert-butyl, n-pentyl, 2-pentyl, 3-pentyl and (2,4,4)-trimethyl-pent-2-yl;

R²¹ denotes a group selected from the group consisting of methyl, ethyl, n-propyl, isopropyl, n-butyl, isobutyl, 2-butyl, tert-butyl, n-pentyl and (2,4,4)-trimethyl-pent-2-yl or a phenyl group which in each case is unsubstituted;

M¹ denotes a group selected from the group consisting of groups 1, 3, 5, 22 and 36,

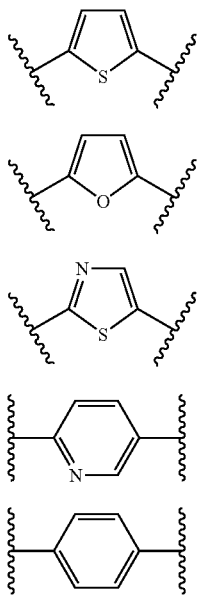

which in each case is unsubstituted, and which in each case can be linked in any direction via the positions marked by a wavy line with the bicyclic ring system and the carbon atom of the triple bond; and M² denotes a group selected from the group consisting of phenyl, 2-pyrimidinyl, 5-pyrimidinyl, 2-thiophenyl (2-thienyl), 3-thiophenyl (3-thienyl), 2-pyridinyl, 3-pyridinyl, 4-pyridinyl, 2-thiazolyl and 4-thiazolyl, which optionally may be unsubstituted or substituted with 1, 2, 3, 4 or 5 substituents independently selected from the group consisting of F, Cl, Br, —CN, —OH, —O—CH₃, —OH, —CF₃, methyl, ethyl, n-propyl, iso-propyl, n-butyl, sec-butyl, iso-butyl and tert-butyl.

24. A compound as claimed in claim 1, selected from the group consisting of:

[1]  6-(5-(phenylethynyl)thiophene-2-yl)-N-(2,4,4-trimethylpentane-2-yl)-imidazo[2,1-b]thiazole-5-amine,
[2]  N-tert-butyl-6-(5-(pyridine-2-ylethynyl)thiophene-2-yl)-imidazo[2,1-b]thiazole-5-amine,
[3]  N-tert-butyl-3-methyl-6-(5-(pyridine-2-ylethynyl)thiophene-2-yl)-imidazo[2,1-b]thiazole-5-amine,
[4]  N-tert-butyl-2-methyl-6-(5-(pyridine-2-ylethynyl)thiophene-2-yl)-imidazo[2,1-b]thiazole-5-amine,
[5]  N-tert-butyl-2,3-dimethyl-6-(5-(pyridine-2-ylethynyl)thiophene-2-yl)-imidazo[2,1-b]thiazole-5-amine,
[6]  N-tert-butyl-2-chloro-6-(5-(pyridine-2-ylethynyl)thiophene-2-yl)-imidazo[2,1-b]thiazole-5-amine,
[7]  N-tert-butyl-6-(5-(pyridine-4-ylethynyl)thiophene-2-yl)imidazo[2,1-b]thiazole-5-amine,
[8]  5-(tert-butylamino)-6-(5-(pyridine-2-ylethynyl)thiophene-2-yl)-imidazo[2,1-b]thiazole-2-carboxylic acid methylester,
[9] N-tert-butyl-6-(5-(pyridine-2-ylethynyl)thiazole-2-yl)imidazo[2,1-b]thiazole-5-amine;
[10] 6-(5-pyridine-2-ylethynyl)thiophene-2-yl)-N-(2,4,4-trimethylpentane-2-yl)imidazo[2,1-b]thiazole-5-amine,
[11] N-tert-butyl-2-methyl-6-(4-(pyridine-2-ylethynyl)phenyl)imidazo[2,1-b]thiazole-5-amine,
[12] N-tert-butyl-6-(5-(pyridine-2-ylethynyl)furan-2-yl)imidazo[2,1-b]thiazole-5-amine,
[13]  N-tert-butyl-3-methyl-6-(5-(phenylethynyl)thiophene-2-yl)imidazo[2,1-b]thiazole-5-amine,
[14]  6-(5-(pyridine-2-ylethynyl)thiophene-2-yl)imidazo[2,1-b]thiazole-5-amine,
[15]  N-tert-butyl-6-(5-(pyrimidine-2-ylethynyl)thiophene-2-yl)imidazo[2,1-b]thiazole-5-amine,
[16]  N-tert-butyl-6-(5-((3-fluoropyridine-2-yl)ethynyl)thiophene-2-yl)imidazo[2,1-b]thiazole-5-amine,
[17]  N-tert-butyl-6-(5-((2-fluoropyridine-4-yl)ethynyl)thiophene-2-yl)imidazo[2,1-b]thiazole-5-amine,
[18] N-tert-butyl-6-(5-(thiophene-2-ylethynyl)thiophene-2-yl)imidazo[2,1-b]thiazole-5-amine,
[19] N-tert-butyl-6-(5-(thiazole-2-ylethynyl)thiophene-2-yl)imidazo[2,1-b]thiazole-5-amine,
[20]  3-((5-(5-(tert-butylamino)imidazo[2,1-b]thiazole-6-yl)thiophene-2-yl)ethynyl)phenol,
[21]  3-((5-(5-(tert-butylamino)imidazo[2,1-b]thiazole-6-yl)thiophene-2-yl)ethynyl)benzonitrile,
[22]  N-ethyl-6-(6-(phenylethynyl)pyridine-3-yl)imidazo[2,1-b]thiazole-5-amine,
[23]  N-tert-butyl-6-(5-((3-methylpyridine-2-yl)ethynyl)thiophene-2-yl)imidazo[2,1-b]thiazole-5-amine,
[24]  N-(6-(5-(pyridine-2-ylethynyl)thiophene-2-yl)imidazo[2,1-b]thiazole-5-yl)acetamide and
[25]  N-(6-(5-(pyridine-2-ylethynyl)thiophene-2-yl)imidazo[2,1-b]thiazole-5-yl)benzamide;

or a salt thereof.

25. A compound as claimed in claim 1, wherein after 60 minutes incubation in 450 µg protein from pig brain homogenate at a temperature between 20° C. and 25° C., said compound in a concentration of less than 2500 nM induces a 50-percent displacement of [³H]-2-methyl-6-(3-methoxyphenyl)-ethynylpyridine which is present in a concentration of 5 nM.

26. A compound as claimed in claim 25, wherein after 60 minutes incubation in 450 µg protein from pig brain homogenate at a temperature between 20° C. and 25° C., said compound in a concentration of less than 100 nM induces a 50-percent displacement of [³H]-2-methyl-6-(3-methoxyphenyl)-ethynylpyridine which is present in a concentration of 5 nM.

27. A method of producing a substituted imidazo[2,1-b]thiazole compound as claimed in claim 1, said method comprising:

reacting a compound corresponding to formula II

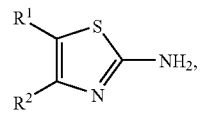

wherein R¹ and R² have the meanings given in claim 1,
in a reaction medium, optionally in the presence of at least one organic or inorganic acid or at least one transition metal salt, with an isocyanide of formula III,

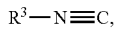
III wherein $R^3$ has the meaning given in claim 1, and with an aldehyde of formula IV,

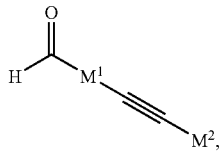
IV wherein $M^1$ and $M^2$ have the meanings given in claim 1, to yield a compound corresponding to formula V

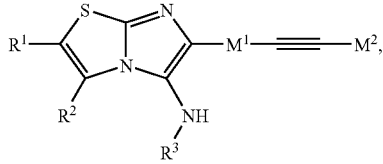
V wherein $R^1$, $R^2$, $R^3$, $M^1$ and $M^2$ have the meanings given above, and
optionally transforming the compound into a salt, and
optionally purifying or isolating the compound or salt,
or
reacting a compound of formula II

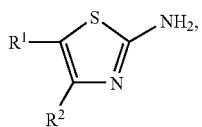
II wherein $R^1$ and $R^2$ have the meanings given in claim 1,
in a reaction medium, optionally in the presence of at least one organic or inorganic acid or at least one transition metal salt,
with an isocyanide of formula III

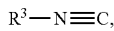
III wherein $R^3$ has the meaning given in claim 1, and with an aldehyde of formula VI

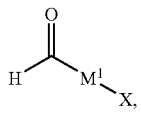
VI wherein $M^1$ has the meaning given in claim 1 and X denotes a leaving group, to yield a compound corresponding to formula VII

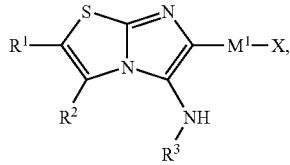
VII wherein $R^1$, $R^2$, $R^3$, $M^1$ and X have the meanings given above, and
optionally transforming the compound into a salt, and
optionally purifying or isolating the compound or salt,
and reacting the compound of formula VII
with an acetylene compound corresponding to formula XI

XI wherein each R independently denotes a linear or branched alkyl group or an unsubstituted phenyl group,
in a reaction medium, optionally in the presence of a catalyst and optionally in the presence of an inorganic or organic base,
to yield a compound corresponding to formula XII

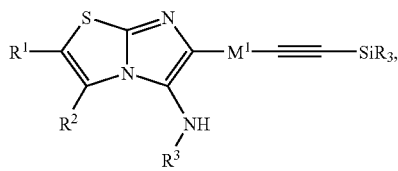
XII wherein $R^1$, $R^2$, $R^3$, $M^1$ and each R have the meanings given above, and
optionally transforming the compound into a salt, and
optionally purifying or isolating the compound or salt, and
optionally transforming the compound of formula XII
in a reaction medium, optionally in the presence of an inorganic or organic base,
optionally in the presence of an inorganic salt, and optionally in the presence of an ammonium salt,
into a compound of formula XIII

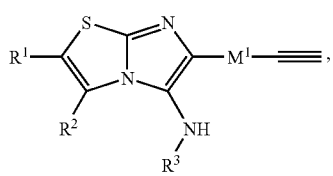
XIII wherein $R^1$, $R^2$, $R^3$ and $M^1$ have the meanings given above, and
optionally transforming the compound into a salt, and
optionally purifying or isolating the compound or salt, and reacting a compound of formula XIII or a compound of formula XII with a compound corresponding to the formula

M²-X wherein M² has the meaning given in claim 1, and X denotes a leaving group,
in a reaction medium, optionally in the presence of a catalyst, optionally in the presence of an inorganic or organic base, optionally in the presence of an inorganic salt, and optionally in the presence of an ammonium salt
to yield a compound corresponding to formula V

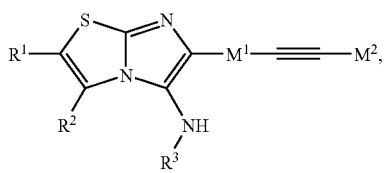

V wherein R¹, R², R³, M¹ and M² have the meanings given above, and
optionally transforming the compound into a salt, and
optionally purifying or isolating the compound or salt,
or
reacting the compound of formula VII
with an acetylene compound corresponding to formula VIII

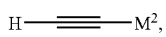

VIII wherein M² has the meaning given in claim 1,
in a reaction medium, optionally in the presence of a catalyst, and optionally in the presence of an inorganic or organic base,
to yield a compound corresponding to the foregoing formula V
wherein R¹, R², R³, M¹ and M² have the meanings given above, and
optionally transforming the compound into a salt, and
optionally purifying or isolating the compound or salt, and
optionally reacting the compound of formula V
with a compound corresponding to the formula

R⁴—X wherein R⁴ has the meaning given in claim 1, and X denotes a leaving group,
in a reaction medium, in the presence of an organic or inorganic base,
or with a compound corresponding to the formula

R²¹—C(=O)—OH wherein R²¹ has the meaning given in claim 1,
in a reaction medium, optionally in the presence of an organic or inorganic base and
optionally in the presence of a coupling agent,
or with a compound corresponding to the formula

R²¹—C(=O)—X wherein R²¹ has the meaning given in claim 1, and X denotes a leaving group, in a reaction medium, optionally in the presence of an organic or inorganic base, or with a compound corresponding to the formula

R²¹—C(=O)—H wherein R²¹ has the meaning given in claim 1,
in a reaction medium, optionally in the presence of at least one reducing agent, to yield a compound corresponding to formula I

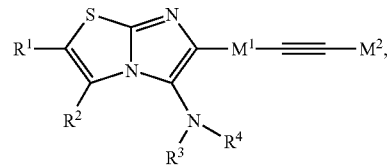

I or a salt thereof,
wherein R¹, R², R³, R⁴, M¹ and M² have the meanings given above, and
optionally purifying or isolating the compound or salt thereof.

28. A method for producing a substituted imidazo[2,1-b]thiazole compound according to claim 1, said method comprising:
reacting a compound of formula V

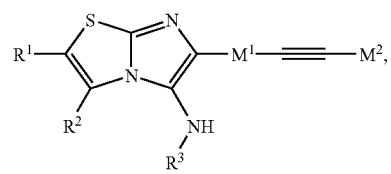

V wherein R¹, R², R³, M¹ and M² have the meanings given in claim 1,
optionally in a reaction medium in the presence of an organic or inorganic acid, to yield a compound corresponding to formula IX

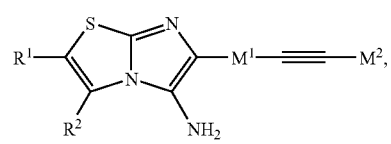

IX wherein R¹, R², M¹ and M² have the meanings given above, and
optionally transforming the compound into a salt, and
optionally reacting the compound of formula IX or salt thereof
in a reaction medium, in the presence of at least one inorganic or organic base, with a compound corresponding to the formula

R³—X wherein R³ has the meaning given in claim 1, and X denotes a leaving group, in a reaction medium, optionally in the presence of an organic or inorganic base and optionally in the presence of a coupling agent,
or with a compound corresponding to the formula

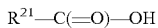

wherein $R^{21}$ has the meaning given in claim 1,
in a reaction medium, optionally in the presence of an organic or inorganic base,
with a compound corresponding to the formula

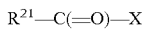

wherein $R^{21}$ has the meaning given in claim 1, and X denotes a leaving group,
or in a reaction medium, optionally in the presence of a reducing agent,
with a compound corresponding to the formula

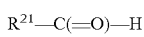

wherein $R^{21}$ has the meaning given in claim 1,
to yield a compound corresponding to formula X

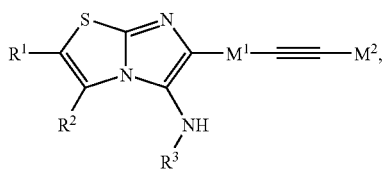

or a salt thereof,
wherein $R^1$, $R^2$, $R^3$, $M^1$ and $M^2$ have the meanings given above, and
optionally purifying or isolating the compound of formula X or salt thereof, and
optionally reacting the compound of formula X or salt thereof
with a compound corresponding to the formula

wherein $R^4$ has the meaning given in claim 1, and X denotes a leaving group,
in a reaction medium, in the presence of an organic or inorganic base,
or with a compound corresponding to the formula

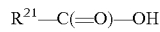

wherein $R^{21}$ has the meaning given above,
in a reaction medium, optionally in the presence of an organic or inorganic base and optionally in the presence of a coupling agent,
or with a compound corresponding to the formula

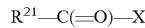

wherein $R^{21}$ has the meaning given above, and X denotes a leaving group,
in a reaction medium, optionally in the presence of an organic or inorganic base,
or with a compound corresponding to the formula

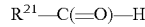

wherein $R^{21}$ has the meaning given above,
in a reaction medium, optionally in the presence of a reducing agent,
to yield a compound corresponding to formula I

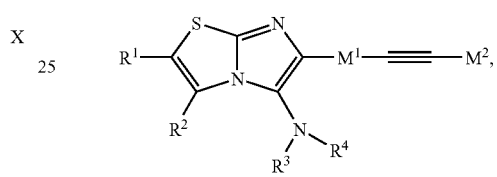

or a salt thereof,
wherein $R^1$, $R^2$, $R^3$, $R^4$, $M^1$ and $M^2$ have the meanings given above, and
optionally purifying or isolating the compound of formula I or salt thereof.

29. A pharmaceutical composition comprising a compound as claimed in claim 1, and at least one physiologically acceptable auxiliary substance.

30. A method of treating or inhibiting pain in a subject, wherein said pain is selected from the group consisting of acute pain, chronic pain, neuropathic pain and visceral pain, said method comprising administering to said subject a pharmacologically effective amount of a compound as claimed in claim 1.

* * * * *